US012674196B2

(12) United States Patent
Kühnemund

(10) Patent No.: US 12,674,196 B2
(45) Date of Patent: Jul. 7, 2026

(54) METHODS AND COMPOSITIONS FOR IMPROVED PROBE SPECIFICITY

(71) Applicant: 10x Genomics, Inc., Pleasanton, CA (US)

(72) Inventor: Malte Kühnemund, Stockholm (SE)

(73) Assignee: 10X GENOMICS, INC., Pleasanton, CA (US)

( * ) Notice: Subject to any disclaimer, the term of this patent is extended or adjusted under 35 U.S.C. 154(b) by 605 days.

(21) Appl. No.: 18/097,990

(22) Filed: Jan. 17, 2023

(65) Prior Publication Data

US 2023/0279480 A1 Sep. 7, 2023

Related U.S. Application Data

(60) Provisional application No. 63/300,562, filed on Jan. 18, 2022.

(51) Int. Cl.
*C12Q 1/6855* (2018.01)
*C12Q 1/6806* (2018.01)

(52) U.S. Cl.
CPC ......... *C12Q 1/6855* (2013.01); *C12Q 1/6806* (2013.01); *C12Q 2600/16* (2013.01)

(58) Field of Classification Search
CPC ........................... C12Q 1/6855; C12Q 1/6806; C12Q 2600/16; C12Q 1/6844
See application file for complete search history.

(56) References Cited

U.S. PATENT DOCUMENTS

| | | | |
|---|---|---|---|
| 4,318,846 A | 3/1982 | Khanna et al. | |
| 4,683,195 A | 7/1987 | Mullis et al. | |
| 4,683,202 A | 7/1987 | Mullis | |
| 4,757,141 A | 7/1988 | Fung et al. | |
| 4,800,159 A | 1/1989 | Mullis et al. | |
| 4,849,336 A | 7/1989 | Miyoshi et al. | |
| 4,965,188 A | 10/1990 | Mullis et al. | |
| 5,066,580 A | 11/1991 | Lee | |
| 5,091,519 A | 2/1992 | Cruickshank | |
| 5,151,507 A | 9/1992 | Hobbs et al. | |
| 5,188,934 A | 2/1993 | Menchen | |
| 5,198,537 A | 3/1993 | Huber et al. | |
| 5,344,757 A | 9/1994 | Holtke et al. | |
| 5,354,657 A | 10/1994 | Boehringer et al. | |
| 5,366,860 A | 11/1994 | Bergot et al. | |
| 5,512,462 A | 4/1996 | Cheng | |
| 5,599,675 A | 2/1997 | Brenner | |
| 5,635,352 A | 6/1997 | Urdea et al. | |
| 5,688,648 A | 11/1997 | Mathies | |
| 5,695,940 A | 12/1997 | Drmanac et al. | |
| 5,702,888 A | 12/1997 | Holtke et al. | |
| 5,750,341 A | 5/1998 | Macevicz | |
| 5,800,996 A | 9/1998 | Lee et al. | |
| 5,847,162 A | 12/1998 | Lee et al. | |
| 5,990,479 A | 11/1999 | Weiss et al. | |
| 6,054,274 A | 4/2000 | Sampson et al. | |
| 6,172,218 B1 | 1/2001 | Brenner | |
| 6,207,392 B1 | 3/2001 | Weiss et al. | |
| 6,251,303 B1 | 6/2001 | Bawendi et al. | |
| 6,265,552 B1 | 7/2001 | Schatz | |
| 6,291,187 B1 | 9/2001 | Kingsmore et al. | |
| 6,306,597 B1 | 10/2001 | Macevicz | |
| 6,319,426 B1 | 11/2001 | Bawendi et al. | |
| 6,322,901 B1 | 11/2001 | Bawendi et al. | |
| 6,323,009 B1 | 11/2001 | Lasken et al. | |
| 6,344,329 B1 | 2/2002 | Lizardi et al. | |
| 6,368,801 B1 | 4/2002 | Faruqi | |
| 6,391,937 B1 | 5/2002 | Beuhler et al. | |
| 6,423,551 B1 | 7/2002 | Weiss et al. | |
| 6,426,513 B1 | 7/2002 | Bawendi et al. | |
| 6,444,143 B2 | 9/2002 | Bawendi et al. | |
| 6,534,266 B1 | 3/2003 | Singer | |
| 6,576,291 B2 | 6/2003 | Bawendi et al. | |
| 6,969,488 B2 | 11/2005 | Bridgham et al. | |
| 7,057,026 B2 | 6/2006 | Barnes et al. | |

(Continued)

FOREIGN PATENT DOCUMENTS

| | | |
|---|---|---|
| WO | WO 1991/017160 | 11/1991 |
| WO | WO 2017/143155 | 8/2017 |

(Continued)

OTHER PUBLICATIONS

Ali et al. "Rolling circle amplification: a versatile tool for chemical biology, materials science and medicine." *Chemical Society Reviews* 43.10 (2014): 3324-3341.

Archer et al., "Selective and flexible depletion of problematic sequences from RNA-seq libraries at the cDNA stage," BMC Genomics. (2014) 15(1):401.

Baner et al., "Signal amplification of padlock probes by rolling circle replication," Nucleic Acids Res. (1998) 26(22):5073-5078.

Bibikova et al., "Quantitative gene expression profiling in formalin-fixed, paraffin-embedded tissues using universal bead arrays," Am J Pathol. Nov. 2004;165(5):1799-807.

Bolognesi et al., "Multiplex Staining by Sequential Immunostaining and Antibody Removal on Routine Tissue Sections," J. Histochem. Cytochem. (2017); 65(8): 431-444.

Capodieci et al., "Gene expression profiling in single cells within tissue," Nat Methods. (2005) 2(9): 663-5.

(Continued)

*Primary Examiner* — Cynthia B Wilder

(74) *Attorney, Agent, or Firm* — MORRISON & FOERSTER LLP

(57) ABSTRACT

The present disclosure relates in some aspects to methods and compositions for analysis of a target nucleic acid, such as in situ detection of a region of interest in a polynucleotide in a tissue sample. In some aspects, provided herein are methods and compositions for detecting a region of interest in a target nucleic acid. In some aspects, provided herein are circularizable probes and oligonucleotide probes for analyzing a target nucleic acid, in which corresponding hybridization regions between the circularizable probe and the oligonucleotide probe comprise a barcode region comprising one or more barcodes. In some aspects, the oligonucleotide probe and/or the circularizable probe comprise one or more modifications.

20 Claims, 10 Drawing Sheets

(56)　　　　　References Cited

U.S. PATENT DOCUMENTS

| | | |
|---|---|---|
| 7,255,994 B2 | 8/2007 | Lao |
| 7,264,929 B2 | 9/2007 | Rothberg et al. |
| 7,345,159 B2 | 3/2008 | Ju et al. |
| 7,473,767 B2 | 1/2009 | Dimitrov |
| 7,534,991 B2 | 5/2009 | Miller et al. |
| 7,544,794 B1 | 6/2009 | Benner |
| 7,555,155 B2 | 6/2009 | Levenson et al. |
| 7,566,537 B2 | 7/2009 | Balasubramanian et al. |
| 7,655,898 B2 | 2/2010 | Miller |
| 7,893,227 B2 | 2/2011 | Wu et al. |
| 7,910,304 B2 | 3/2011 | Drmanac |
| 7,941,279 B2 | 5/2011 | Hwang et al. |
| 7,989,166 B2 | 8/2011 | Koch et al. |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,632,975 B2 | 1/2014 | Vander Horn et al. |
| 8,658,361 B2 | 2/2014 | Wu et al. |
| 8,771,950 B2 | 7/2014 | Church et al. |
| 8,986,926 B2 | 3/2015 | Ferree et al. |
| 9,201,063 B2 | 12/2015 | Sood et al. |
| 9,217,178 B2 | 12/2015 | Fedurco et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,512,422 B2 | 12/2016 | Barnard et al. |
| 9,541,504 B2 | 1/2017 | Hoyt |
| 9,551,032 B2 | 1/2017 | Landegren et al. |
| 9,624,538 B2 | 4/2017 | Church et al. |
| 9,650,406 B2 | 5/2017 | Zhou et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,889,422 B2 | 2/2018 | Smith et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,138,509 B2 | 11/2018 | Church et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,550,429 B2 | 2/2020 | Harada et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,174,281 B1 | 11/2021 | Graham et al. |
| 11,287,422 B2 | 3/2022 | Previte et al. |
| 11,434,525 B2 | 9/2022 | Glezer |
| 11,459,603 B2 | 10/2022 | Tyagi et al. |
| 11,499,185 B2 | 11/2022 | Vijayan et al. |
| 11,643,679 B2 | 5/2023 | Glezer et al. |
| 11,999,999 B2 | 6/2024 | Ju et al. |
| 2002/0045045 A1 | 4/2002 | Adams et al. |
| 2003/0013091 A1 | 1/2003 | Dimitrov |
| 2003/0017264 A1 | 1/2003 | Treadway et al. |
| 2005/0100900 A1 | 5/2005 | Kawashima et al. |
| 2006/0188901 A1 | 8/2006 | Barnes et al. |
| 2006/0240439 A1 | 10/2006 | Smith et al. |
| 2006/0281109 A1 | 12/2006 | Barr et al. |
| 2007/0166705 A1 | 7/2007 | Milton et al. |
| 2007/0166708 A1 | 7/2007 | Dimitrov et al. |
| 2009/0118128 A1 | 5/2009 | Liu et al. |
| 2010/0015607 A1 | 1/2010 | Geiss et al. |
| 2010/0047924 A1 | 2/2010 | Webster et al. |
| 2010/0055733 A1 | 3/2010 | Lutolf et al. |
| 2010/0112710 A1 | 5/2010 | Geiss et al. |
| 2010/0261026 A1 | 10/2010 | Ferree et al. |
| 2010/0262374 A1 | 10/2010 | Hwang et al. |
| 2011/0059865 A1 | 3/2011 | Smith et al. |
| 2011/0223585 A1 | 9/2011 | Gullberg et al. |
| 2012/0270305 A1 | 10/2012 | Reed et al. |
| 2013/0079232 A1 | 3/2013 | Kain et al. |
| 2013/0260372 A1 | 10/2013 | Buermann et al. |
| 2013/0288249 A1 | 10/2013 | Gullbert |
| 2013/0323729 A1 | 12/2013 | Landegren et al. |
| 2014/0371088 A1 | 12/2014 | Webster |
| 2016/0024555 A1 | 1/2016 | Church et al. |
| 2016/0108458 A1 | 4/2016 | Frei et al. |
| 2016/0305856 A1 | 10/2016 | Boyden et al. |
| 2016/0376642 A1 | 12/2016 | Landegren et al. |
| 2017/0009278 A1 | 1/2017 | Söderberg et al. |
| 2017/0081489 A1 | 3/2017 | Rodriques et al. |
| 2017/0101672 A1 | 4/2017 | Luo et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0320226 A1 | 11/2018 | Church et al. |
| 2019/0017106 A1 | 1/2019 | Frisen et al. |
| 2019/0032121 A1 | 1/2019 | Daugharthy et al. |
| 2019/0032128 A1 | 1/2019 | Chen et al. |
| 2019/0055594 A1 | 2/2019 | Samusik et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0177800 A1 | 6/2019 | Boutet et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2019/0367969 A1 | 12/2019 | Belhocine |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |

(56) References Cited

U.S. PATENT DOCUMENTS

| | | |
|---|---|---|
| 2020/0239946 A1 | 7/2020 | Dewal |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2021/0017587 A1 | 1/2021 | Cai et al. |
| 2021/0115504 A1 | 4/2021 | Cai et al. |
| 2021/0164039 A1 | 6/2021 | Wang et al. |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340621 A1 | 11/2021 | Daugharthy et al. |
| 2021/0388423 A1 | 12/2021 | Bava et al. |
| 2021/0388424 A1 | 12/2021 | Bava |
| 2022/0049302 A1 | 2/2022 | Daugharthy et al. |
| 2022/0049303 A1 | 2/2022 | Busby et al. |
| 2022/0083832 A1 | 3/2022 | Shah |
| 2022/0084628 A1 | 3/2022 | Shah |
| 2022/0084629 A1 | 3/2022 | Shah |
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |
| 2022/0235403 A1 | 7/2022 | Costa |
| 2022/0282306 A1 | 9/2022 | Bava et al. |
| 2022/0282316 A1 | 9/2022 | Bava |
| 2022/0282319 A1 | 9/2022 | Verheyen |
| 2022/0372570 A1 | 11/2022 | Costa |
| 2022/0380838 A1 * | 12/2022 | Kühnemund .......... C12Q 1/682 |
| 2022/0403458 A1 | 12/2022 | Bava |
| 2023/0002808 A1 | 1/2023 | Mignardi |
| 2023/0012607 A1 | 1/2023 | Kuhnemund et al. |
| 2023/0013775 A1 | 1/2023 | Chen et al. |
| 2023/0015226 A1 | 1/2023 | Chen et al. |
| 2023/0026886 A1 | 1/2023 | Chen |
| 2023/0031305 A1 | 2/2023 | Hernandez Neuta et al. |
| 2023/0031996 A1 | 2/2023 | Hernandez Neuta et al. |
| 2023/0035685 A1 | 2/2023 | Hernandez Neuta et al. |
| 2023/0037182 A1 | 2/2023 | Bava et al. |
| 2023/0039148 A1 | 2/2023 | Verheyen |
| 2023/0041485 A1 | 2/2023 | Hernandez Neuta et al. |
| 2023/0044650 A1 | 2/2023 | Dockter |
| 2023/0057571 A1 | 2/2023 | Costa et al. |
| 2023/0061542 A1 | 3/2023 | Kuhnemund |
| 2023/0084407 A1 | 3/2023 | Hernandez Neuta et al. |
| 2023/0159997 A1 | 5/2023 | Belhocine et al. |
| 2023/0160794 A1 | 5/2023 | Dockter et al. |
| 2023/0183787 A1 | 6/2023 | Bava et al. |
| 2023/0242974 A1 | 8/2023 | Costa et al. |
| 2023/0279465 A1 | 9/2023 | He et al. |
| 2023/0279475 A1 | 9/2023 | Kuhnemund et al. |
| 2023/0279480 A1 | 9/2023 | Kuhnemund |
| 2023/0287478 A1 | 9/2023 | Bava |
| 2023/0314327 A1 | 10/2023 | Hoffman |
| 2023/0314328 A1 | 10/2023 | Costa |
| 2023/0323427 A1 | 10/2023 | Schnall-Levin |
| 2023/0323430 A1 | 10/2023 | Shastry |
| 2023/0323437 A1 | 10/2023 | Chen et al. |
| 2023/0374573 A1 | 11/2023 | Qian et al. |
| 2023/0374580 A1 | 11/2023 | Costa |
| 2023/0416821 A1 | 12/2023 | Bava et al. |
| 2024/0002902 A1 | 1/2024 | Jakobsen et al. |
| 2024/0026426 A1 | 1/2024 | Bava |
| 2024/0026427 A1 | 1/2024 | Kuhnemund et al. |
| 2024/0026439 A1 | 1/2024 | Sasaki |
| 2024/0026448 A1 | 1/2024 | Costa |
| 2024/0035070 A1 | 2/2024 | Christopherson |
| 2024/0035071 A1 | 2/2024 | Delaney et al. |
| 2024/0035072 A1 | 2/2024 | Christopherson |
| 2024/0043910 A1 | 2/2024 | Shastry |
| 2024/0043914 A1 | 2/2024 | Chen et al. |
| 2024/0060119 A1 | 2/2024 | Bava |
| 2024/0084373 A1 | 3/2024 | Shastry |
| 2024/0084378 A1 | 3/2024 | Marks et al. |
| 2024/0101978 A1 | 3/2024 | Boghospor et al. |
| 2024/0132938 A1 | 4/2024 | Kuhnemund |
| 2024/0141418 A1 | 5/2024 | Mielinis |
| 2024/0150816 A1 | 5/2024 | Feng et al. |
| 2024/0158852 A1 | 5/2024 | Belhocine et al. |
| 2024/0167081 A1 | 5/2024 | Bava et al. |
| 2024/0175082 A1 | 5/2024 | Costa |
| 2024/0175083 A1 | 5/2024 | Bava et al. |
| 2024/0191297 A1 | 6/2024 | Christopherson et al. |
| 2024/0209330 A1 | 6/2024 | Shastry et al. |
| 2024/0218424 A1 | 7/2024 | Costa et al. |
| 2024/0218437 A1 | 7/2024 | Belhocine et al. |
| 2024/0263219 A1 | 8/2024 | Kuhnemund |
| 2024/0263220 A1 | 8/2024 | Olofsson |
| 2024/0264155 A1 | 8/2024 | Costa |

FOREIGN PATENT DOCUMENTS

| | | | | |
|---|---|---|---|---|
| WO | WO-2019068880 A1 * | 4/2019 | .......... | C12Q 1/6841 |
| WO | WO 2019/199579 | 10/2019 | | |
| WO | WO 2020/076976 | 4/2020 | | |
| WO | WO 2020/076979 | 4/2020 | | |
| WO | WO 2020/096687 | 5/2020 | | |
| WO | WO 2020/099640 | 5/2020 | | |
| WO | WO 2020/117914 | 6/2020 | | |
| WO | WO 2020/123316 | 6/2020 | | |
| WO | WO 2020/123742 | 6/2020 | | |
| WO | WO 2020/142490 | 7/2020 | | |
| WO | WO 2020/240025 | 12/2020 | | |
| WO | WO 2020/254519 | 12/2020 | | |
| WO | WO 2021/123282 | 6/2021 | | |
| WO | WO 2021/123286 | 6/2021 | | |
| WO | WO 2021/138676 | 7/2021 | | |
| WO | WO 2021/155063 | 8/2021 | | |
| WO | WO 2021/168326 | 8/2021 | | |
| WO | WO 2023/018756 | 8/2022 | | |
| WO | WO 2022/236011 | 11/2022 | | |
| WO | WO 2023/278409 | 1/2023 | | |
| WO | WO 2023/108139 | 6/2023 | | |
| WO | WO 2023/141476 | 7/2023 | | |
| WO | WO 2023/172915 | 9/2023 | | |
| WO | WO 2023/192302 | 10/2023 | | |
| WO | WO 2024/148300 | 7/2024 | | |

OTHER PUBLICATIONS

Chen et al., "Nanoscale imaging of RNA with expansion microscopy," Nat Methods. (2016) 13:679-684.

Chen et al., "Expansion Microscopy," Science (2015) 347(6221):543-548.

Conze et al., "Single molecule analysis of combinatorial splicing," Nucleic Acids Res. (2010) 38(16): e163.

Dean et al., "Rapid Amplification of Plasmid and Phage DNA Using Phi29 DNA Polymerase and Multiply-Primed Rolling Circle Amplification," Genome Research (2001) 11:1095-1099.

Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.

Faruqi et al., "High-throughput genotyping of single nucleotide polymorphisms with rolling circle amplification," BMC Genomics. (2001) 2:4.

Femino et al., "Visualization of single RNA transcripts in situ," Science. (1998) 280(5363): 585-90.

Forcucci et al., "All-plastic miniature fluorescence microscope for point-of-care readout of bead-based bioassays," J Biomed Opt. (2015) 20(10): 105010.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Glass et al., "SIMPLE: a sequential immunoperoxidase labeling and erasing method," J Histochem Cytochem. (2009) 57(10); 899-905.

(56) References Cited

OTHER PUBLICATIONS

Goh, J.J.L. et al. (Jul. 2020, e-pub. Jun. 15, 2020). "Highly Specific Multiplexed RNA Imaging in Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

Gunderson et al. "Decoding randomly ordered DNA arrays." Genome research 14.5 (2004): 870-877.

Gyllborg et al., "Hybridization-based in situ sequencing (HybISS) for spatially resolved transcriptomics in human and mouse brain tissue," Nucleic Acids Res. (2020) 48(19): e112.

Han et al., "Quantum-dot-tagged microbeads for multiplexed optical coding of biomolecules," Nat Biotechnol. (2001) 19(7): 631-5.

Henegariu et al., "Custom fluorescent-nucleotide synthesis as an alternative method for nucleic acid labeling," Nature Biotechnol. (2000) 18:345.

Itzkovitz et al., "Single-molecule transcript counting of stem-cell markers in the mouse intestine," Nat Cell Biol. (2011) 14(1): 106-14.

Itzkovitz et al., "Validating Transcripts with Probes and Imaging Technology," Nat Methods. (2011) 8(4 Suppl): S12-S19.

Jamur et al., "Permeabilization of cell membranes," Method Mol. Biol. (2010) 588: 63-66 (abstract only).

Korlach et al. "Selective aluminum passivation for targeted Immobilization of single DNA polymerase molecules in zero-mode waveguide nanostructures." Proceedings of the National Academy of Sciences 105.4 (2008): 1176-1181.

Krzywkowski et al., "Chimeric padlock and iLock probes for increased efficiency of targeted RNA detection," RNA. (2019) 25(1):82-89.

Krzywkowski et al., "Fidelity of RNA templated end-joining by chlorella virus DNA ligase and a novel iLock assay with improved direct RNA detection accuracy," Nucleic Acids Res. (2017) 45(18): e161.

Lagunavicius et al., "Novel application of Phi29 DNA polymerase: RNA detection and analysis in vitro and in situ by target RNA-primed RCA," RNA. (2009) 15(5):765-71.

Lakowicz et al., "Silver particles enhance emission of fluorescent DNA oligomers," Bio Techniques (2003) 34(1); 62-66.

Larsson et al. "In situ detection and genotyping of individual mRNA molecules," Nat Methods. (2010) 7(5):395-397.

Lee et al. "Highly Multiplexed Subcellular RNA Sequencing In Situ", Science (2014) 343(6177):1360-1363.

Levene et al. "Zero-mode waveguides for single-molecule analysis at high concentrations." science 299.5607 (2003): 682-686.

Levsky et al., "Fluorescence in situ hybridization: past, present and future," J Cell Sci. (2003) 116(Pt 14): 2833-8.

Levsky et al., "Single-cell gene expression profiling," Science. (2002) 297(5582): 836-40.

Lin et al., "Highly multiplexed imaging of single cells using a high-throughput cyclic immunofluorescence method," Nat Commun. (2015) 6:8390.

Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.

Lizardi et al., "Mutation detection and single-molecule counting using isothermal rolling-circle amplification," Nat Genet. (1998) 19(3): 225-232.

Lundquist et al. "Parallel confocal detection of single molecules in real time." Optics letters 33.9 (2008): 1026-1028.

Lyamichev et al., "Comparison of the 5′ nuclease activities of taq DNA polymerase and its isolated nuclease domain," Proc Natl Acad Sci USA. (1999) 96(11): 6143-6148.

Ma et al., "RNA template-dependent 5′ nuclease activity of Thermus aquaticus and Thermus thermophilus DNA polymerases," J Biol Chem. (2000) 275(32): 24693-700.

Maierhorfer et al., "Multicolor deconvolution microscopy of thick biological specimens," Am J Pathol. (2003) 162(2): 373-9.

McGinn et al., "New technologies for DNA analysis—a review of the READNA Project," N Biotechnol. (2016) 33(3): 311-30. doi: 10.1016/j.nbt.2015.10.003.

Meade et al. "Multiplexed DNA detection using spectrally encoded porous SiO2 photonic crystal particles," Anal Chem. (2009) 81(7): 2618-25.

Mitra et al., "Fluorescent in situ sequencing on polymerase colonies," Anal. Biochem. (2003) 320, 55-65.

Moffitt et al., "RNA Imaging with Multiplexed Error-Robust Fluorescence In Situ Hybridization (MERFISH)," Methods in Enzymology, (2016) 572; 1-49.

Mohsen et al., "The Discovery of Rolling Circle Amplification and Rolling Circle Transcription," Acc Chem Res. (2016) 49(11): 2540-2550.

Nallur et al., "Signal amplification by rolling circle amplification on DNA microarrays," Nucleic Acids Res. (2001) 29(23): e118.

Payne et al. "In situ genome sequencing resolves DNA sequence and structure in intact biological samples," Science. (2021) 371(6532): eaay3446. doi: 10.1126/science.aay3446. Epub Dec. 31, 2020.

Pirici et al., "Antibody elution method for multiple immunohistochemistry on primary antibodies raised in the same species and of the same subtype," J Histochem Cytochem. (2009) 57(6); 567-75.

Raj et al., "Imaging individual mRNA molecules using multiple singly labeled probes," Nat Methods. (2008) 5(10): 877-879.

Rajeswari et al., "Multiple pathogen biomarker detection using an encoded bead array in droplet PCR," J Microbiol Methods. (2017) 139: 22-28.

Rouhanifard et al. "ClampFISH detects individual nucleic acid molecules using click chemistry-based amplification," Nat Biotechnol. (2018) 17 pages. doi: 10.1038/nbt.4286.

Schweitzer et al. "Immunoassays with rolling circle DNA amplification: a versatile platform for ultrasensitive antigen detection," Proc. Natl Acad. Sci. USA (2000) 97:10113-119.

Schweitzer et al., "Multiplexed protein profiling on microarrays by rolling-circle amplification," Nature Biotech. (2002) 20:359-365.

Shendure et al, "Accurate multiplex polony sequencing of an evolved bacterial genome," Science (2005) 309(5741); 1728-1732.

Sun et al., "Composite organic-inorganic nanoparticles as Raman labels for tissue analysis," Nano Lett. (2007) 7(2): 351-6.

Takei et al., (Feb. 2021, e-pub Jan. 27, 2021). "Integrated Spatial Genomics Reveals Global Architecture of Single Nuclei," Nature 590(7845):344-350, 53 pages. doi: 10.1038/s41586-020-03126-2.

Vandernoot et al., "cDNA normalization by hydroxyapatite chromatography to enrich transcriptome diversity in RNA-seq applications," Biotechniques, (2012) 53(6) 373-80.

Wählby et al., "Sequential immunofluorescence staining and image analysis for detection of large numbers of antigens in individual cell nuclei," Cytometry. (2002) 47(1): 32-41.

Wang et al., "Three-dimensional intact-tissue sequencing of single-cell transcriptional states," Science. (2018) 361(6400): eaat5691.

Weibrecht et al., "Simultaneous visualization of both signaling cascade activity and end-point gene expression in single cells," PLoS One. (2011) 6(5): e20148.

Wetmur, "DNA Probes: Applications of the Principles of Nucleic Acid Hybridization," Critical Reviews in Biochemistry and Molecular Biology, (1991) 26(91); 227-259.

Wilson et al., "Encoded microcarriers for high-throughput multiplexed detection," Angew Chem Int Ed Engl. (2006) 18;45(37): 6104-17.

Wu, C. et al. "RollFISh Achieves Robust Quantification of Single-Molecule RNA Biomarkers in Paraffin-Embedded Tumor Tissue Samples," Commun Biol. (2018) 1:(209):1-8. doi: 10.1038/s42003-018-0218-0.

Zeng et al., "Integrative in situ mapping of single-cell transcriptional states and tissue histopathology in an Alzheimer's disease model," Preprint from bioRxiv, Jan. 16, 2022; DOI: 10.1101/2022.01.14.476072.

Zhao et al., "Rolling circle amplification: applications in nanotechnology and biodetection with functional nucleic acids," Angew Chem Int Ed Engl. (2008) 47(34): 6330-7. (Abstract and Supporting Information only).

(56)          References Cited

OTHER PUBLICATIONS

Zhao et al., "Advances of multiplex and high throughput biomolecular detection technologies based on encoding microparticles," Sci China Chem. (2011) 54(8):1185.

Chen et al., "Efficient in situ barcode sequencing using padlock probe-based BaristaSeq," Nucleic Acids Res. (2018) 46(4): e22.

Sun et al., "Integrating barcoded neuroanatomy with spatial transcriptional profiling enables identification of gene correlates of projections," Nat Neurosci. (2021) 24(6):873-885.

* cited by examiner

METHODS AND COMPOSITIONS FOR IMPROVED PROBE SPECIFICITY

CROSS-REFERENCE TO RELATED APPLICATIONS

This application claims priority to U.S. Provisional Patent Application No. 63/300,562, filed Jan. 18, 2022, entitled "Methods and Compositions for Improved Probe Specificity," which is herein incorporated by reference in its entirety for all purposes.

FIELD

The present disclosure relates in some aspects to methods and compositions for analysis of a target analyte, such as in situ detection of a region of interest in a nucleic acid in a tissue sample.

BACKGROUND

Methods are available for analyzing nucleic acids present in a biological sample, such as a cell or a tissue. Current methods of oligonucleotide probe-based assay methods for in situ analysis may suffer from low sensitivity, specificity, and/or detection efficiency and may require careful and laborious optimization. Thus, improved methods for analyzing nucleic acids present in a biological sample are needed. Provided herein are methods, compositions, and kits that meet such and other needs.

SUMMARY

In some aspects, disclosed herein is a method for analyzing a biological sample, the method comprising: a) contacting the biological sample comprising a target nucleic acid comprising hybridization region HR1' and hybridization region HR2', with: (i) a circularizable probe comprising hybridization region HR1 and hybridization region HRb, wherein HR1 hybridizes to HR1', and wherein HRb comprises a barcode region. In some embodiments, HRb comprises a barcode region which corresponds to the target nucleic acid or a sequence thereof, and (ii) an oligonucleotide probe comprising hybridization region HR2 and hybridization region HRb', wherein HR2 hybridizes to HR2'; b) when HRb hybridizes to HRb', ligating the ends of the circularizable probe using the oligonucleotide probe as a splint to generate a circularized probe; c) using HRb' or a portion thereof or a primer to prime rolling circle amplification (RCA) of the circularized probe to generate an RCA product; and d) detecting the RCA product, thereby detecting the target nucleic acid in the biological sample. In some embodiments, the circularizable probe further comprises hybridization region HRa, and the oligonucleotide probe further comprises hybridization region HRa' which hybridizes to HRa. In any of the embodiments herein, the RCA of the circularized probe is performed using a primer that is not the oligonucleotide probe. In some embodiments, HRa' is complementary to HRa and HRb' is complementary to HRb. In some embodiments, HRa' and HRa each comprises a barcode region, and the barcode regions are complementary. In some embodiments, HRb' and HRb each comprises a barcode region, and the barcode regions are complementary. In some embodiments, provided in HRa' and HRb' is a barcode region that is complementary to a split barcode region in HRa and HRb.

In some aspects, disclosed herein is a method comprising: a) contacting the biological sample comprising a target nucleic acid comprising hybridization region HR1' and hybridization region HR2', with: i) a circularizable probe comprising hybridization region HR1 and hybridization region HRb, wherein HR1 hybridizes to HR1', and wherein HRb comprises a barcode region and ii) an oligonucleotide probe comprising hybridization region HR2 and hybridization region HRb', wherein HR2 hybridizes to HR2' and wherein HRb' hybridizes to HRb; b) ligating the ends of the circularizable probe using the oligonucleotide probe as a splint to generate a circularized probe; c) using HRb' or a portion thereof or a primer to prime rolling circle amplification (RCA) of the circularized probe to generate an RCA product; and d) detecting the RCA product, thereby detecting the target nucleic acid in the biological sample. In any of the embodiments herein, the RCA of the circularized probe is performed using a primer that is not the oligonucleotide probe.

In some embodiments, disclosed herein is a method for analyzing a biological sample, the method comprising: a) contacting the biological sample comprising a target nucleic acid comprising in the 5' to 3' direction, hybridization region HR1' and hybridization region HR2', with: i) a plurality of circularizable probes, wherein a circularizable probe comprises in the 5' to 3' direction: hybridization region HRa, hybridization region HR1, and hybridization region HRb, wherein HRb comprises a 3' splint hybridization region and a barcode region, and ii) a plurality of oligonucleotide probes, wherein an oligonucleotide probe comprises in the 5' to 3' direction: hybridization region HR2, hybridization region HRa', and hybridization region HRb', wherein HRb' comprises a region complementary to the 3' splint hybridization region of HRb, wherein a sequence of HRb' is complementary to the barcode region of HRb; and wherein HRa hybridizes to HRa', HR1 hybridizes to HR1', HRb hybridizes to its complementary region in HRb', and HR2 hybridizes to HR2'; b) ligating the 5' end of HRa and the 3' end of HRb using the oligonucleotide probe as a splint, wherein the circularizable probe is circularized to generate a circularized probe; c) using HRb' or a portion thereof to prime rolling circle amplification (RCA) of the circularized probe to generate an RCA product; and d) detecting the RCA product, thereby detecting the target nucleic acid in the biological sample. In any of the embodiments herein, HRb' can comprise a barcode region complementary to the barcode region of HRb. In any of the embodiments herein, the biological sample can be contacted with another oligonucleotide probe comprising HRa' and HRb", wherein HRb" comprises a barcode region that is not complementary to the barcode region of HRb, and while the ends of the circularizable probe may be ligated using the another oligonucleotide probe as a splint to generate a circularized probe, HRb" or a portion thereof is not configured to prime RCA of the circularized probe generated by ligation splinted on the another oligonucleotide probe.

In some embodiments, disclosed herein is a method for analyzing a biological sample, the method comprising: a) contacting the biological sample comprising a target nucleic acid comprising in the 5' to 3' direction, hybridization region HR1' and hybridization region HR2', with: (i) a plurality of circularizable probes, wherein a circularizable probe comprises in the 5' to 3' direction: hybridization region HRa, hybridization region HR1, and hybridization region HRb, wherein HRb comprises a 3' splint hybridization region and a barcode region. In some embodiments, the barcode region corresponds to the target nucleic acid or a sequence thereof, and (ii) a plurality of oligonucleotide probes, wherein an oligonucleotide probe comprises in the 5' to 3' direction: hybridization region HR2, hybridization region HRa', and hybridization region HRb', wherein HRb' comprises a region complementary to the 3' splint hybridization region of HRb; and wherein: HRa hybridizes to HRa', HR1 hybridizes to HR1', the 3' splint hybridization region of HRb hybridizes to its complementary region in HRb', and HR2 hybridizes to HR2'; b) ligating the 5' end of HRa and the 3' end of HRb using the oligonucleotide probe as a splint, wherein the circularizable probe is circularized to generate a circularized probe; in some embodiments, the 5' end of HRa is the 5' splint hybridization region and in some embodiments the 3' end of HRb is the 3' splint hybridization region; c) when a sequence of HRb' is complementary to the barcode region of HRb, using HRb' or a portion thereof to prime rolling circle amplification (RCA) of the circularized probe to generate an RCA product; in some embodiments, the barcode of HRb' is 3' to the region complementary to the 3' splint hybridization region of HRb; and d) detecting the RCA product, thereby detecting the target nucleic acid in the biological sample. In any of the embodiments herein, HRa can function as a 5' splint hybridization region which, together with the 3' splint hybridization region of HRb, hybridizes to the oligonucleotide probe.

In any of the embodiments herein, the barcode region of HRb can be at the 3' end of the circularizable probe, or the 3' terminal nucleotide of the barcode region can be 1, 2, 3, 4, 5, 6, 7, 8, 9, 10, 11, 12, 13, 14, 15, or more nucleotides from the 3' terminal nucleotide of the circularizable probe. In any of the embodiments herein, the barcode region of HRb can be at the 3' end of HRb, or the 3' terminal nucleotide of the barcode region can be 1, 2, 3, 4, 5, 6, 7, 8, 9, 10, 11, 12, 13, 14, 15, or more nucleotides from the 3' terminal nucleotide of HRb. In any of the embodiments herein, the barcode region of HRb can be at the 5' end of HRb, or the 5' terminal nucleotide of the barcode region can be 1, 2, 3, 4, 5, 6, 7, 8, 9, 10, 11, 12, 13, 14, 15, or more nucleotides from the 5' terminal nucleotide of HRb. In any of the embodiments herein, the barcode region of HRb can be between the 3' end of HRb and the 5' end of HRb, the 3' terminal nucleotide of the barcode region can be 1, 2, 3, 4, 5, 6, 7, 8, 9, 10, 11, 12, 13, 14, 15, or more nucleotides from the 3' terminal nucleotide of HRb, and the 5' terminal nucleotide of the barcode region can be 1, 2, 3, 4, 5, 6, 7, 8, 9, 10, 11, 12, 13, 14, 15, or more nucleotides from the 5' terminal nucleotide of HRb.

In any of the embodiments herein, the oligonucleotide probe can comprise one or more modifications that protect the oligonucleotide probe from 3'→5' exonuclease degradation. In some embodiments, the oligonucleotide probe can be HRb'. In any of the embodiments herein, the one or more modifications may allow primer extension by a polymerase, and the method does not need to comprise contacting the biological sample with an enzyme capable of removing the one or more modifications. In any of the embodiments herein, the one or more modifications may block primer extension by a polymerase, and the method may further comprise contacting the biological sample with an agent capable of removing the one or more modifications. In some embodiments, the agent is an enzyme capable of cleaving the oligonucleotide probe to remove one or more 3' terminal nucleotides. In some embodiments, cleaving the oligonucleotide probe can be within HRb' or in a 3' overhang. In some embodiments, the enzyme cleaves within a barcode region in HRb'.

In any of the embodiments herein, the sequence of HRb' can comprise a complementary barcode region that is complementary to the barcode region of HRb or portion thereof. In some embodiments, the complementary barcode region is cleaved by a uracil-DNA glycosylase (UDG) and/or an endonuclease. In some embodiments, the endonuclease can be Endonuclease VIII. In some embodiments, the complementary barcode region or a portion thereof is hybridized to the barcode region and primes RCA of the circularized probe.

In any of the embodiments herein, the one or more modifications can comprise a terminal modification and/or an internal modification. In some embodiments, the one or more modifications can comprise a terminal nucleotide base modification and/or an internal nucleotide base modification.

In any of the embodiments herein, HRb' can comprise one or more modifications that protect the sequence of HRb' from 3'→5' exonuclease degradation by a polymerase while allowing priming by the polymerase. In some embodiments, the one or more modifications can comprise a terminal nucleotide modification and/or an internal nucleotide modification. In some embodiments, the one or more modifications comprise a 3' thiophosphate-protection, a phosphorothioate bond, a 2'-modified nucleoside, an inverted deoxythymidine base, and/or a 2'-O-methyl ribonucleotide. In some embodiments, the one or more modifications can comprise a 2'-O-methyl ribonucleotide that is a 3' terminal nucleotide of HRb'.

In any of the embodiments herein, the plurality of oligonucleotide probes may comprise another oligonucleotide probe comprising HRa' and hybridization region HRb" in the 5' to 3' direction, wherein HRb" comprises (i) a region complementary to the 3' splint hybridization region of HRb and (ii) a barcode region that is not complementary to the barcode region of HRb. In some embodiments, HRb" or a portion thereof is not configured to prime RCA of a circularized probe generated by ligation using the another oligonucleotide probe as a splint.

In any of the embodiments herein, HRa' may be common or universal among oligonucleotide probes targeting different target nucleic acids. In any of the embodiments herein, HRa may be common or universal among circularizable probes targeting different target nucleic acids.

In any of the embodiments herein, the another oligonucleotide probe comprising HRa' and hybridization region HRb" may comprise a hybridization region that is not complementary to a sequence in the target nucleic acid. In some embodiments, the another oligonucleotide probe nonspecifically binds to the target nucleic acid and/or the circularizable probe (which may be specifically hybridized to the target nucleic acid). In some embodiments, the another oligonucleotide probe nonspecifically binds to the biological sample at or near the target nucleic acid and/or the circularizable probe (which may be specifically hybridized to the target nucleic acid).

In any of the embodiments herein, HRb' can comprise one or more modifications that block priming by a polymerase, and when the sequence of HRb' hybridizes to the barcode region, the oligonucleotide probe may be cleaved to remove the one or more modifications, and the portion of the oligonucleotide probe that remains hybridized to the circularized probe can prime RCA of the circularized probe. In some embodiments, HRb' is cleaved, and a portion of HRb' remains hybridized to the barcode region and primes RCA of the circularized probe. In some embodiments, the one or more modifications is removed whiled the barcode region of HRb' is not cleaved. In some embodiments, a portion of the barcode region in HRb' is cleaved off together with the one or more modifications. In some embodiments, the portion of the barcode region can be about 2, about 5, about 10, or more nucleotides of the barcode region.

In some embodiments, provided herein is a method for analyzing a biological sample, the method comprising: a) contacting the biological sample comprising a target nucleic acid comprising in the 5' to 3' direction, hybridization region HR1' and hybridization region HR2', with: (i) a plurality of circularizable probes, wherein a circularizable probe comprises in the 5' to 3' direction: hybridization region HRa, hybridization region HR1, and hybridization region HRb, wherein HRb comprises a 3' splint hybridization region and a barcode region. In some embodiments, the barcode region corresponds to the target nucleic acid or a sequence thereof, and (ii) a plurality of oligonucleotide probes, wherein an oligonucleotide probe comprises one or more modifications that block priming by a polymerase and, in the 5' to 3' direction: hybridization region HR2, hybridization region HRa', and hybridization region HRb', wherein HRb' comprises a region complementary to the 3' splint hybridization region of HRb; and wherein: HRa hybridizes to HRa', HR1 hybridizes to HR1', the 3' splint hybridization region of HRb hybridizes to its complementary region in HRb', and HR2 hybridizes to HR2'; b) ligating the 5' end of HRa and the 3' end of HRb using the oligonucleotide probe as a splint, wherein the circularizable probe is circularized to generate a circularized probe; c) contacting the biological sample with an enzyme capable of removing the one or more modifications, wherein when a sequence of HRb' is complementary to the barcode region of HRb, HRb' is cleaved to remove the one or more modifications, and a portion of HRb' remains hybridized to the barcode region; d) using the portion of HRb' that remains hybridized to the circularized probe to prime rolling circle amplification (RCA) of the circularized probe to generate an RCA product; and e) detecting the RCA product, thereby detecting the target nucleic acid in the biological sample. In any of the embodiments herein, the ligation in step b) and the contacting in step c) can occur in either order.

In some embodiments, provided herein is a method for analyzing a biological sample, the method comprising: a) contacting the biological sample comprising a target nucleic acid comprising in the 5' to 3' direction, hybridization region HR1' and hybridization region HR2', with: i) a plurality of circularizable probes, wherein a circularizable probe comprises in the 5' to 3' direction: hybridization region HRa, hybridization region HR1, and hybridization region HRb, wherein HRb comprises a 3' splint hybridization region and a barcode region, and ii) a plurality of oligonucleotide probes, wherein a first oligonucleotide probe of the plurality of oligonucleotide probes comprises one or more modifications that block priming by a polymerase and, in the 5' to 3' direction: hybridization region HR2, hybridization region HRa', and hybridization region HRb', wherein HRb' comprises a region complementary to the 3' splint hybridization region of HRb and a sequence complementary to the barcode region of HRb; and wherein: HRa hybridizes to HRa', HR1 hybridizes to HR1', HRb hybridizes to its complementary region in HRb', and HR2 hybridizes to HR2'; b) ligating the 5' end of HRa and the 3' end of HRb using the oligonucleotide probe as a splint, wherein the circularizable probe is circularized to generate a circularized probe; c) contacting the biological sample with an enzyme capable of removing the one or more modifications, wherein when a sequence of HRb' is complementary to the barcode region of HRb, HRb' is cleaved to remove the one or more modifications, and a portion of HRb' remains hybridized to the barcode region; d) using the portion of HRb' that remains hybridized to the circularized probe to prime rolling circle amplification (RCA) of the circularized probe to generate an RCA product; and; e) detecting the RCA product, thereby detecting the target nucleic acid in the biological sample.

In some embodiments, the plurality of oligonucleotide probes comprises another oligonucleotide probe comprising one or more modifications that block priming by a polymerase and HR2, HRa', and hybridization region HRb" in the 5' to 3' direction, wherein HRb" comprises (i) a region complementary to the 3' splint hybridization region of HRb and (ii) a barcode region that is not complementary to the barcode region of HRb. In some embodiments, the barcode region in HRb" is not hybridized to the barcode region of HRb. In some embodiments, HRb" is not cleaved by the enzyme to remove the one or more modifications that block priming by the polymerase.

In any of the embodiments herein, HRb" can be blocked from generating an RCA product of a circularized probe generated by ligation using the another oligonucleotide probe as a splint.

In any of the embodiments herein, HRb' and/or HRb" may comprise one or more uracil-containing residues and/or nuclease cleavage sites cleavable by an enzyme. In any of the embodiments herein, HRb' and/or HRb" may be cleavable by a uracil-specific excision reagent and/or an endonuclease. In some embodiments, the uracil-specific excision reagent can be a uracil-DNA glycosylase (UDG), and in some embodiments, the endonuclease can be Endonuclease VIII.

In any of the embodiments herein, the portion of HRb' that is cleaved off may be no more than 16, no more than 14, no more than 12, no more than 10, no more than 8, no more than 6, no more than 4 nucleotides, or no more than 2 nucleotides in length. In some embodiments, the portion of HRb' that is cleaved off does not remain hybridized to the circularizable or circularized probe. In some embodiments, the portion of HRb' that is cleaved off does not prime RCA templated on the circularized probe.

In some embodiments, provide herein is a method for analyzing a biological sample, the method comprising: a) contacting the biological sample comprising a target nucleic acid comprising in the 5' to 3' direction, hybridization region HR1' and hybridization region HR2', with: (i) a plurality of circularizable probes, wherein a circularizable probe comprises in the 5' to 3' direction: hybridization region HRa, hybridization region HR1 and hybridization region HRb, wherein HRb comprises a 3' splint hybridization region and a barcode region. In some embodiments, the barcode region can correspond to the target nucleic acid or a sequence thereof, and (ii) a plurality of oligonucleotide probes, wherein an oligonucleotide probe comprises in the 5' to 3' direction: hybridization region HR2, hybridization region HRa', and hybridization region HRb', wherein HRb' comprises a region complementary to the 3' splint hybridization region of HRb; and wherein: HRa hybridizes to HRa', HR1 hybridizes to HR1', the 3' splint hybridization region of HRb hybridizes to its complementary region in HRb', and HR2 hybridizes to HR2'; b) ligating the 5' end of HRa and the 3' end of HRb using the oligonucleotide probe as a splint, wherein the circularizable probe is circularized to generate a circularized probe; c) contacting the biological sample with an enzyme capable of cleaving a single-stranded portion of HRb' of the oligonucleotide probe and/or a single-stranded portion of HRb of the circularizable probe, wherein when a sequence of HRb' is complementary to the barcode region of HRb, the HRb/HRb' duplex is not cleaved by the enzyme and HRb' or a portion remains hybridized to the barcode region; d) using HRb' or the portion thereof to prime rolling circle amplification (RCA) of the circularized probe to generate an RCA product; and e) detecting the RCA product, thereby detecting the target nucleic acid in the biological sample. In some embodiments, the portion of HRb' in step d) can be generated by cleaving HRb', for instance, using one or more enzymes disclosed herein. In some embodiments, the one or more embodiments disclosed herein can be an enzyme that nicks or cleaves HRb' in a duplex such as a uracil-DNA glycosylase (UDG) and/or an endonuclease. In some embodiments, the endonuclease can be Endonuclease VIII.

In any of the embodiments herein, the plurality of oligo-nucleotide probes may comprise another oligonucleotide probe comprising HRa' and hybridization region HRb" in the 5' to 3' direction. In any of the embodiments herein, HRb" may comprise (i) a region complementary to the 3' splint hybridization region of HRb and (ii) a barcode region that is not complementary to the barcode region of HRb. In some embodiments, the barcode region in HRb" is not hybridized to the barcode region of HRb to form a duplex. In some embodiments, the barcode region in HRb" remains single-stranded and is cleaved by the enzyme. In some embodiments, the barcode region of HRb remains single-stranded and is cleaved by the enzyme. In some embodiments, the cleaving by the enzyme can linearize a circular-ized probe generated by ligation using the another oligonucleotide probe as a splint such that an RCA product is not generated.

In any of the embodiments herein, the barcode region in HRb" can correspond to another target nucleic acid distinct from the target nucleic acid. In any of the embodiments herein, the barcode region in HRb" can correspond to a distinct sequence of the target nucleic acid.

In any of the embodiments herein, the enzyme can be a single-strand-specific nuclease that acts on single-stranded nucleic acids or single-stranded regions in double-stranded nucleic acids. In any of the embodiments herein, the enzyme can be a restriction endonuclease. In some embodiments, the restriction endonuclease can be a Type II restriction enzyme. In any of the embodiments herein, the enzyme can be selected from the group consisting of AvaII, HaeII, DdeI, AluI, Sau3 AI, AccII, TthHB8I, and HapII.

In some aspects, provided herein is a method for analyz-ing a biological sample, the method comprising: a) contact-ing the biological sample comprising a target nucleic acid comprising in the 5' to 3' direction: hybridization region HR1' and hybridization region HR2', with: (i) a plurality of circularizable probes, wherein a circularizable probe com-prises hybridization region HRa, hybridization region HR1, and hybridization region HRb, wherein HRb comprises a barcode region. In some embodiments, the barcode region corresponds to the target nucleic acid or a sequence thereof, and (ii) a plurality of oligonucleotide probes, wherein an oligonucleotide probe comprises hybridization region HR2, hybridization region HRa', and hybridization region HRb'; and wherein: HRa hybridizes to HRa', HR1 hybridizes to HR1', and HR2 hybridizes to HR2'; b) when the barcode region is complementary to HRb' or a portion thereof, ligating HRa and HRb using the oligonucleotide probe as a splint, wherein the circularizable probe is circularized to generate a circularized probe; c) using the oligonucleotide probe or a portion thereof or a primer to prime rolling circle amplification (RCA) of the circularized probe to generate an RCA product; and d) detecting the RCA product, thereby detecting the target nucleic acid in the biological sample. In some embodiments, the circularizable probe comprises HRa, HR1, and HRb in the 5' to 3' direction. In some embodiments, the oligonucleotide probe comprises HR2, HRa', and HRb' in the 5' to 3' direction. In some embodi-ments, the target nucleic acid comprises HR1' and HR2' in the 5' to 3' direction.

In any of the embodiments herein, the barcode region can be (i) at the 3' end of HRb, (ii) at the 5' end of HRb, or (iii) between the 3' end of HRb and the 5' end of HRb. In any of the embodiments herein, the barcode region can be at the 3' end of the circularizable probe. In any of the embodiments herein, the circularizable probe can comprise a sequence 3' to the barcode region. In any of the embodiments herein, the sequence 3' to the barcode region can hybridize to the oligonucleotide probe. In some embodiments, the sequence 3' to the barcode region can be no more than 5 nucleotides in length. In some embodiments, the sequence 3' to the barcode region that hybridizes to the oligonucleotide probe can be a common or universal region. In some embodiments, the common or universal region can be among circularizable probes targeting different target nucleic acids, which can be used to provide a common or universal ligation site. In some embodiments, the universal ligation site can be a generic ligation site for probes targeting different target nucleic acids. In any of the embodiments herein, the sequence 3' to the barcode region can form a 3' flap that does not hybridize to the oligonucleotide probe. In some embodiments, the barcode region is complementary to a barcode region in the oligonucleotide probe, the 3' flap of the circularizable probe may be cleaved by an enzyme. In some embodiments, the enzyme can be an endonuclease or a polymerase to remove the 3' flap or a portion thereof.

In any of the embodiments herein, the circularizable probe may comprise a sequence 5' to the barcode region. In some embodiments, the sequence 5' to the barcode region can hybridize to the oligonucleotide probe. In any of the embodi-ments herein, when the barcode region is not complemen-tary to a barcode region in the oligonucleotide probe, hybridization between the circularizable probe and the oli-gonucleotide probe may be insufficiently stable to allow circularization of the circularizable probe. In some embodi-ments, the barcode region in the oligonucleotide probe can correspond to a nucleic acid different from the target nucleic acid or sequence thereof. In some embodiments, HRb does not hybridize to the oligonucleotide probe. In some embodi-ments, hybridization between the circularizable probe and the oligonucleotide probe may be insufficiently stable to allow ligation of HRa and HRb.

In any of the embodiments herein, the plurality of oligo-nucleotide probes comprises another oligonucleotide probe comprising HRa' and hybridization region HRb", wherein HRb" comprises i) a region complementary to the 3' splint hybridization region of HRb and ii) a barcode region that is not complementary to the barcode region of HRb. In some embodiments, the barcode region in HRb" is not hybridized to the barcode region of HRb. In any of the embodiments herein, hybridization between HRb" and the circularizable probe is not sufficiently stable to allow circularization of the circularizable probe. In any of the embodiments herein, the circularizable probe can comprise a sequence 5' to HRa, and the sequence 5' to HRa may form a 5' flap that does not hybridize to the oligonucleotide probe. In any of the embodi-ments herein, the method can further comprise when the barcode region is complementary to a barcode region in the oligonucleotide probe, cleaving the 5' flap of the circularizable probe by an enzyme. In some embodiments, the enzyme can be an endonuclease or a polymerase to remove the 5' flap or a portion thereof. In any of the embodiments herein, the circularizable probe comprises a sequence 5' to HRa, wherein when HRa of the circularizable probe hybridizes to HRa' of the another oligonucleotide probe, the sequence 5' to the HRa forms a 5' flap that does not hybridize to the another oligonucleotide probe, and the 5' flap is not cleaved using the enzyme.

In some embodiments, disclosed herein is a method for analyzing a biological sample, the method comprising: a) contacting the biological sample comprising a target nucleic acid comprising in the 5' to 3' direction: hybridization region HR1' and hybridization region HR2', with: i) a plurality of circularizable probes, wherein a circularizable probe comprises, in the 5' to 3' direction: a 5' flap, hybridization region HRa, hybridization region HR1, and hybridization region HRb, wherein HRb comprises a barcode region, and ii) a plurality of oligonucleotide probes, wherein an oligonucleotide probe comprises in the 5' to 3' direction: hybridization region HR2, hybridization region HRa', and hybridization region HRb', wherein HRb' or a portion thereof is complementary to the barcode region of HRb; and wherein: HRa hybridizes to HRa', HR1 hybridizes to HR1', and HR2 hybridizes to HR2'; b) cleaving the 5' flap of the circularizable probe by an enzyme; c) ligating HRa and HRb using the oligonucleotide probe as a splint, wherein the circularizable probe is circularized to generate a circularized probe; d) using the oligonucleotide probe or a portion thereof to prime rolling circle amplification (RCA) of the circularized probe to generate an RCA product; and e) detecting the RCA product, thereby detecting the target nucleic acid in the biological sample.

In some embodiments, disclosed herein is a method for analyzing a biological sample, the method comprising: a) contacting the biological sample comprising a target nucleic acid comprising in the 5' to 3' direction: hybridization region HR1' and hybridization region HR2', with: (i) a plurality of circularizable probes, wherein a circularizable probe comprises, in the 5' to 3' direction: a 5' flap, hybridization region HRa, hybridization region HR1, and hybridization region HRb, wherein HRb comprises a barcode region. In some embodiments, the barcode region can correspond to the target nucleic acid or a sequence thereof, and (ii) a plurality of oligonucleotide probes, wherein an oligonucleotide probe comprises in the 5' to 3' direction: hybridization region HR2, hybridization region HRa', and hybridization region HRb'; and wherein: HRa hybridizes to HRa', HR1 hybridizes to HR1', and HR2 hybridizes to HR2'; b) when the barcode region is complementary to HRb' or a portion thereof, cleaving the 5' flap of the circularizable probe by an enzyme. In some embodiments, the enzyme can be an endonuclease or a polymerase; c) ligating HRa and HRb using the oligonucleotide probe as a splint, wherein the circularizable probe is circularized to generate a circularized probe; d) using the oligonucleotide probe or a portion thereof to prime rolling circle amplification (RCA) of the circularized probe to generate an RCA product; and e) detecting the RCA product, thereby detecting the target nucleic acid in the biological sample. In any of the embodiments herein, the endonuclease can be a flap endonuclease 1 (FEN1) and the polymerase can be a *Thermus thermophilus* (Tth) polymerase.

In some embodiments, when the barcode region is not complementary to a barcode region in the oligonucleotide probe, the 5' flap of the circularizable probe is not cleaved, thereby preventing ligation of HRa and HRb and/or circularization of the circularizable probe. In some embodiments, the barcode region in the oligonucleotide probe can correspond to a nucleic acid different from the target nucleic acid or sequence thereof. In some embodiments, the barcode region in HRb'' is not hybridized to the barcode region of HRb. In some embodiments, the 5' flap of the circularizable probe hybridized to HRa' of the another oligonucleotide probe is not cleaved, thereby preventing circularization of the circularizable probe. In any of the embodiments herein, the barcode region in HRb'' of the another oligonucleotide probe corresponds to a nucleic acid different from the target nucleic acid or sequence thereof.

In any of the embodiments herein, the oligonucleotide probe or portion thereof may be used to prime RCA of the circularized probe.

In some embodiments, the circularizable probe comprises HRa, HR1, and HRb in the 3' to 5' direction. In some embodiments, the oligonucleotide probe comprises HR2, HRa', and HRb' in the 3' to 5' direction. In some embodiments, the target nucleic acid comprises HR1' and HR2' in the 3' to 5' direction. In some embodiments, the primer is used to prime RCA of the circularized probe, and the primer is a separate molecule from the oligonucleotide probe.

In any of the embodiments herein, the oligonucleotide probe can be DNA and the circularizable probe may not comprise a ribonucleotide at the 3' end.

In any of the embodiments herein, HRa may not be specific to the target nucleic acid or sequence thereof. In any of the embodiments herein, HRa may be common among circularizable probes for two or more different target nucleic acids or common among circularizable probes for two or more different sequences of a target nucleic acid.

In any of the embodiments herein, the barcode region in HRb can be a first barcode region and HRa may comprise a second barcode region, wherein the first and second barcode regions each independently may comprise one or more barcodes. In any of the embodiments herein, the first barcode region may correspond to the target nucleic acid or sequence thereof. In any of the embodiments herein, the second barcode region may correspond to the target nucleic acid or sequence thereof. In any of the embodiments herein, the combination of the first and second barcode regions may correspond to the target nucleic acid or sequence. In some embodiments, either the first barcode region or the second barcode region may not uniquely correspond to the target nucleic acid or sequence thereof.

In any of the embodiments herein, the plurality of oligonucleotide probes may comprise one or more oligonucleotide probes comprising a first complementary barcode region that hybridizes to the barcode region in HRb, and one or more oligonucleotide probes comprising a second complementary barcode region that is not complementary to the barcode region in HRb. In some embodiments, the second complementary barcode region can be complementary to a barcode region distinct from the barcode region in HRb. In some embodiments, the second complementary barcode region corresponds to a nucleic acid that is different from the target nucleic acid or sequence thereof.

In any of the embodiments herein, the RCA product can be generated and detected in situ in the biological sample.

In any of the embodiments herein, the biological sample may be non-homogenized. In some embodiments, the biological sample can be selected from the group consisting of a formalin-fixed, paraffin-embedded (FFPE) sample, a frozen tissue sample, and a fresh tissue sample. In any of the embodiments herein, the biological sample may be fixed. In any of the embodiments herein, the biological sample may not need to be fixed.

In any of the embodiments herein, the biological sample may be permeabilized. In any of the embodiments herein, the biological sample may be embedded in a matrix. In some embodiments, the matrix may comprise a hydrogel. In any of the embodiments herein, the biological sample may be treated with a proteinase. In any of the embodiments herein, the biological sample may be crosslinked. In some embodiments, the crosslinking can be to a matrix embedding the biological sample. In any of the embodiments herein, the biological sample may be cleared. In any of the embodiments herein, the biological sample may be a tissue slice between about 1 μm and about 50 μm in thickness. In some embodiments, the tissue slice is between about 5 μm and about 35 μm in thickness.

In some embodiments, disclosed herein is a kit comprising one or more of the plurality of circularizable probes and/or one or more of the plurality of oligonucleotide probes, for use in any method disclosed herein. In any of the embodiments herein, the kit may further comprise instructions for performing any method disclosed herein.

In any of the embodiments herein, the circularizable probe comprises a single copy of the barcode region. In any of the embodiments herein, detecting the RCA product comprises detecting the complement of the barcode region of HRb in the RCA product. In any of the embodiments herein, the circularizable probe comprises a second barcode region that does not hybridize to the oligonucleotide probe. In some embodiments, the second barcode region is different from the barcode region of HRb. In any of the embodiments herein, the second barcode region corresponds to the target nucleic acid or a sequence thereof. In any of the embodiments herein, detecting the RCA product comprises detecting the complement of the second barcode region in the RCA product.

In some embodiments, disclosed herein is a kit comprising: i) a plurality of circularizable probes, and ii) a plurality of oligonucleotide probes, for use in the method of any of the embodiments herein. In some embodiments, the kit may further comprise instructions for performing the method of any of the embodiments disclosed herein.

BRIEF DESCRIPTION OF THE DRAWINGS

The drawings illustrate certain embodiments of the features and advantages of this disclosure. These embodiments are not intended to limit the scope of the appended claims in any manner.

DETAILED DESCRIPTION

Figure 1A:
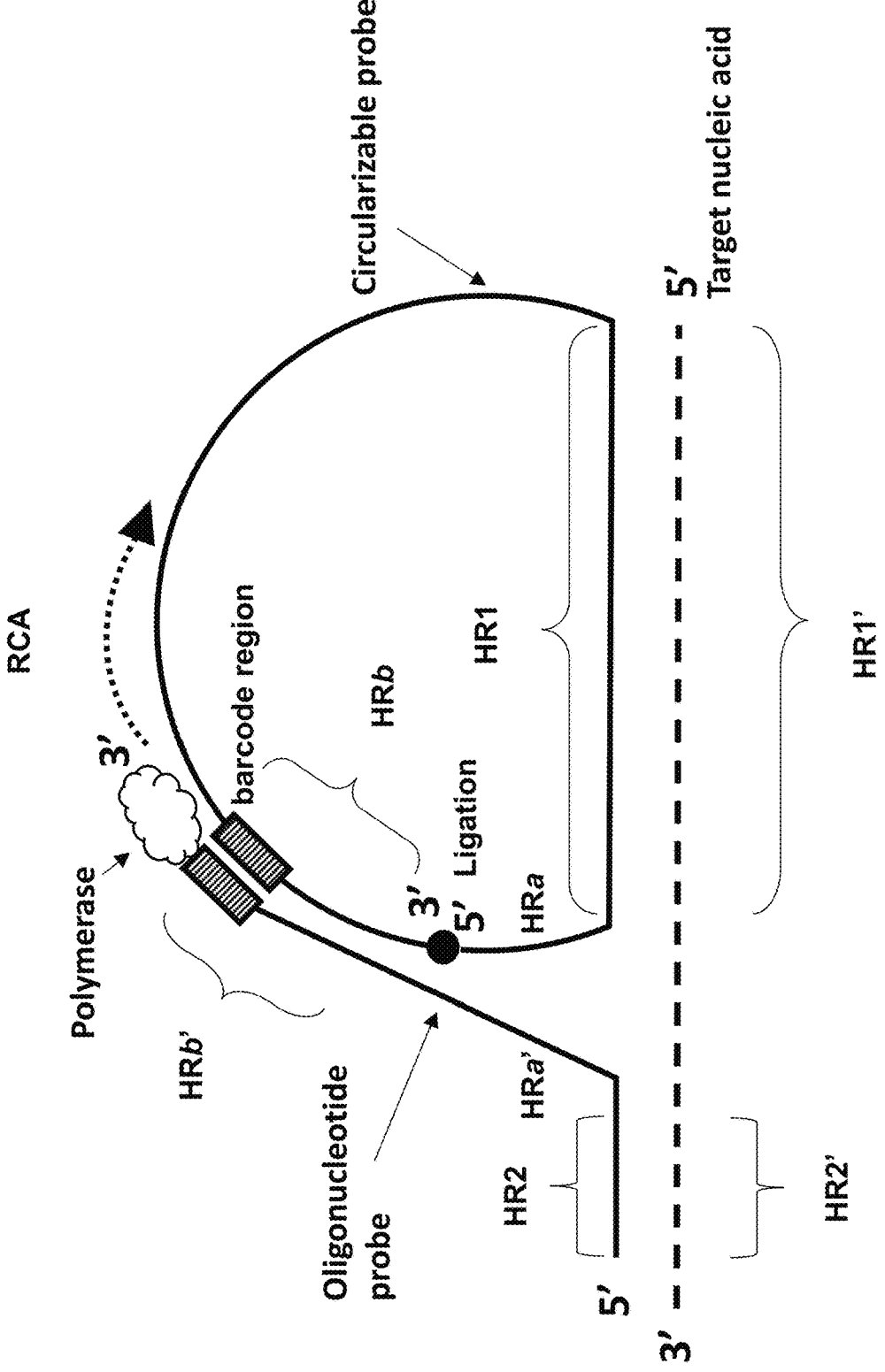
FIG. 1A and FIG. 1B depict exemplary probes and methods for analyzing a biological sample.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

Provided herein are methods for analyzing nucleic acids present in a biological sample, such as a cell or a tissue, that improve the specificity of the probes used for analysis. Also provided are polynucleotides, compositions, kits, systems and devices for use in accordance with the provided methods.

Provided herein are methods, kits, and compositions for analyzing a biological sample, such as for in situ analysis of one or more target nucleic acid(s) and/or one or more analyte(s), e.g., one or more target nucleic acids such as DNA molecules or RNA molecules, in a cell in an intact tissue sample. In some aspects, the provided methods involve the use of a circularizable probe (e.g., a padlock probe) and an oligonucleotide probe to hybridize to a target nucleic acid. In certain embodiments, the provided methods use templated ligation of circularizable probe combined with rolling circle amplification (RCA) to detect target nucleic acids in situ. In some aspects, the circularizable probe-RCA based detection can use a ligase such as T4 DNA ligase to ligate the circularizable probe or probe set (e.g. padlock probe) into a circularized molecule, which will only occur when there has been specific base-pairing between both the circularizable and oligonucleotide probe and the target nucleic acid. However, in some cases, non-specific signals due to the oligonucleotide probe templating the ligation of the circularizable probe in a generic way, and/or amplification of the circularized probe by RCA. The non-specific ligation can result in the probes nonspecifically hybridizing in the biological sample. In addition, currently available designs for circularizable probe-based nucleic acid sequence detection combined with RCA include other disadvantages, for example, that ligation-based nucleic acid detection methods in some cases exhibit poor performance on RNA, e.g., due to reduced end-joining efficiency and/or fidelity of ligases using an RNA template, or low specificity and/or sensitivity of ligation when using certain ligases. In some aspects, the present disclosure provides methods and compositions using approaches and probe designs that allow increasing the specificity and/or sensitivity of a probe-based assay involving using a circularizable probe (e.g. a padlock probe) and an oligonucleotide probe, and preventing nonspecific ligation and/or amplification in methods of.

A SNAIL (Splint Nucleotide Assisted Intramolecular Ligation) probe set may be used to form a circular construct on an RNA molecule. The circular construct is then amplified (e.g., by rolling circle amplification (RCA)) for in situ sequencing, such as sequencing by ligation (e.g., Sequencing by Dynamic Annealing and Ligation (SEDAL)). See, e.g., U.S. Pat. Pub. 20190055594 and 20210164039, which are hereby incorporated by reference in their entirety. SNAIL probes are efficient but may suffer from low specificity because the SNAIL primer templates the ligation of a circularizable probe in a generic way in that SNAIL uses a common circularizable probe ligation sequence. In SNAIL, while the RNA target-complementary sequence and the detection sequence (e.g., barcode) are modified depending on the target, the ligation sequence for probe circularization remains constant, so probe sets against large pools of genes can be designed in an automated fashion. This can generate nonspecific signals when SNAIL primers for RCA are nonspecifically hybridizing in the sample.

In some aspects, the present disclosure provides methods for detecting a target nucleic acid with improved specificity compared to conventional assays such as SNAIL, by using a circularizable probe and an oligonucleotide probe, wherein one or more hybridization regions on the circularizable probe are capable of hybridizing to one or more hybridization regions on the oligonucleotide probe.

In some embodiments, a method disclosed herein takes advantage of the fact that Phi29 may not catalyze RCA when an RCA primer is mismatched with a template and the primer is exonuclease protected. In some embodiments, the primer (e.g., an oligonucleotide probe disclosed herein) can comprise a barcode, e.g., a complement of a gene-specific barcode found in the corresponding circularizable probe or probe set. When the barcode of the primer matches that of the circularizable probe or probe set (or a circularized probe generated therefrom) when both are hybridized to a target nucleic acid (e.g., RNA), the polymerase can extend the primer to perform RCA. However, if the barcode of the primer does not match that of the circularizable probe or probe set (or a circularized probe generated therefrom) when both are hybridized to the same target nucleic acid molecule, no RCA occurs (even if a circularized probe is generated using the primer as a template), since hybridization of the primer to the circularized template is not sufficiently stable and the primer is protected from a nuclease (e.g., exonuclease) so it cannot be chewed back (e.g., a 3' end sequence of the primer may form an overhang that does not hybridize to the circularized template and the 3' end overhang cannot be cleaved or degraded). In some embodiments, the primer carries a blocker on the 3' end that prevents any activity of a polymerase (e.g., Phi29). In some embodiments, the matching primer (one binding and forming a duplex with the barcode on the circularizable probe or probe set) can be nicked at a specific location with an enzyme that cuts single-stranded (only the primer, not on the circularizable probe or probe set). The enzyme could be an endonuclease targeting a sequence, a specific base, or a specific base modification, or the like, or any combination thereof. In some embodiments, the opposite principle can be used, where the non-matching primer causes an enzyme to nick both the primer and the circularizable probe or probe set (or a circularized probe generated therefrom), or just the circularizable probe or probe set (or a circularized probe generated therefrom). In some embodiments, the barcode of the primer (e.g., a gene-specific barcode) can be at or near a ligation site used to circularize the circularizable probe or probe set. In some embodiments, this design makes the circularizable probe hybridization region (e.g., HRa' and/or HRb') of the primer non-universal but gene-specific for probe sets targeting different genes. In some embodiments, a portion of the primer can be a universal region (e.g., a universal splint region) among primers targeting different analytes. In some embodiments, a portion of the primer can be a gene-specific region (e.g., a gene-specific splint region). In some embodiments, the primer can comprise a universal splint region and a gene-specific splint region. In some embodiments, only when the primer and the circularizable probe or probe set match (e.g., being complementary to each other) in the barcode regions can the circularizable probe or probe set be ligated and amplified. In some embodiments, the circularizable probe or probe set can comprise two ligation sites, and both of which can be gene-specific (e.g., one or both ligation sites can be in a gene-specific barcode region or between two gene-specific barcode regions). In some embodiments, a flap such as a 5' flap can be introduced at or near the ligation site, e.g., at the side of the sequence that hybridizes to a universal splint region in the primer. Only when the gene-specific region in the circularizable probe or probe set matches the gene-specific region on the primer, the complex can comprise a three-way junction with a 5' flap that can be removed in an invader reaction (with Taq polymerase for example). Once the flap is removed, the circularizable probe or probe set can be circularized.

In certain embodiments, a corresponding circularizable probe and oligonucleotide probe hybridize to the target nucleic acid, and upon hybridization of the circularizable probe to the oligonucleotide probe, e.g., via complementary hybridization regions, the ends of the circularizable probe are ligated together, circularizing the circularizable probe, using the oligonucleotide probe as a splint. In some embodiments, the portion of the oligonucleotide probe hybridized to the circularized probe primes RCA of the circularized probe.

In some aspects, the present disclosure provides methods for detection of a target nucleic acid in situ. In certain embodiments, the method comprises two probes for each target nucleic acid sequence. In some aspects, the methods and compositions comprise a circularizable probe (e.g., a padlock probe) and an oligonucleotide probe, wherein both probes comprise one or more hybridization regions, wherein a first hybridization region on the circularizable probe and a first hybridization region on the oligonucleotide probe are capable of hybridizing to a first and second hybridization region on the target nucleic acid.

In some embodiments, the methods and compositions include a circularizable probe and an oligonucleotide probe, wherein both probes comprise a barcode region or a complementary sequence thereof. In some aspects, ligation of the 5' and 3' ends of the circularizable probe and/or priming of the circularized probe molecule will occur only if the barcode sequence of the circularizable probe is complementary to the complementary barcode region of the oligonucleotide probe. In some embodiments, the methods provided herein increase binding specificity of a probe-based assay.

In some aspects, specificity is increased by the oligonucleotide probe comprising one or more modifications. In certain embodiments, the modification may protect the hybridization region of the oligonucleotide primer from exonuclease degradation by a polymerase, such as 3'→5' exonuclease degradation. In certain embodiments, the modification may protect the hybridization region of the oligonucleotide primer from exonuclease degradation by a polymerase while allowing priming by the polymerase. In certain embodiments, if a sequence of the oligonucleotide probe, such as a complementary barcode region, is complementary to the barcode region of the circularizable probe, the modification can be enzymatically cleaved and allow the oligonucleotide probe to prime RCA. In some aspects, the modification of the oligonucleotide probe can comprise a modification (e.g., a block) that inhibits priming by a polymerase. In certain embodiments, only if the complementary barcode regions of the oligonucleotide probe and the barcode region of the circularizable probe are complementary to each other, will the barcode sequences hybridize, resulting in the cleavage and removal of the block. In some embodiments, if the barcode sequences of the probes are not complementary, at least a portion of the barcode region of the circularizable probe remains single-stranded and will be enzymatically cleaved.

In some aspects, the specificity of the probe-based assay is improved by the circularized probe molecule comprising one or more modifications. In some aspects, the modification of the circularized probe can comprise a 5' flap that does not hybridize to the oligonucleotide probe. The 5' flap prevents connection and subsequent ligation of the two ends of the circularizable probe and thus the circularizable probe is not circularized. In some aspects, removal or cleavage of the 5' flap by an endonuclease or polymerase will only occur if the barcode sequence of the circularizable probe is complementary to the barcode sequence of the oligonucleotide probe. In certain embodiments, the hybridization of the complementary barcode regions can generate a circularizable probe without the 5' flap and therefore, the ends of the circularizable probe may be ligated and the probe is circularized.

Provided herein are methods involving the use of two probes (a circularizable probe and an oligonucleotide probe) for analyzing one or more target nucleic acid(s), such as a target nucleic acid (for example, a messenger RNA) present in a cell or a biological sample, such as a tissue sample. Also provided are probes, sets of probes, compositions, kits, systems and devices for use in accordance with the provided methods. In some aspects, the provided methods and systems can be applied to detect, image, quantitate, or determine the presence or absence of one or more target nucleic acid(s). In some aspects, the provided embodiments can be employed for in situ detection and/or sequencing of a target nucleic acid in a cell, e.g., in cells of a biological sample or a sample derived from a biological sample.

In some aspects, provided herein are in situ assays using microscopy as a readout, e.g., nucleic acid sequencing, hybridization, or other detection or determination methods involving an optical readout. In some aspects, detection or determination of a sequence of one, two, three, four, five, or more nucleotides of a target nucleic acid in a cell in an intact tissue is performed in situ. In some aspects, detection or determination of a sequence is performed such that the localization of the target nucleic acid (or product or a derivative thereof associated with the target nucleic acid) in the originating sample is detected. In some embodiments, the assay comprises detecting the presence or absence of an amplification product or a portion thereof (e.g., RCA product). In some aspects, exemplary detection includes in situ sequencing and/or in situ sequential hybridization, including sequencing by hybridization, sequencing by ligation, sequencing by synthesis, sequencing by binding, and/or a method based on single molecule fluorescent in situ hybridization (smFISH). In some embodiments, a method for spatially profiling analytes such as the transcriptome or a subset thereof in a biological sample is provided. Methods, compositions, kits, devices, and systems for these in situ assays and in situ detection are provided, for instance, for analyzing a transcriptome or a portion thereof. In some embodiments, a provided method is quantitative and preserves the spatial information within a tissue sample without physically isolating cells or using homogenates.

II. Samples, Analytes, and Target Sequences

A. Samples

A sample disclosed herein can be or derived from any biological sample. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface.

Cell-free biological samples can include extracellular polynucleotides. Extracellular polynucleotides can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include analytes (e.g., protein, RNA, and/or DNA) embedded in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

(i) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 μm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 μm. Thicker sections can also be used if desired or convenient, e.g., at least 70, 80, 90, or 100 μm or more. Typically, the thickness of a tissue section is between 1-100 μm, 1-50 μm, 1-30 μm, 1-25 μm, 1-20 μm, 1-15 μm, 1-10 μm, 2-8 μm, 3-7 μm, or 4-6 μm, but as mentioned above, sections with thicknesses larger or smaller than these ranges can also be analyzed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analyzed successively to obtain three-dimensional information about the biological sample.

(ii) Freezing

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(iii) Fixation and Postfixation

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprises one or more post-fixing (also referred to as postfixation) steps. In some embodiments, one or more post-fixing step is performed after contacting a sample with a polynucleotide disclosed herein, e.g., one or more probes such as a circularizable probe. In some embodiments, one or more post-fixing step is performed after a hybridization complex comprising a probe and a target is formed in a sample. In some embodiments, one or more post-fixing step is performed prior to a ligation reaction disclosed herein, such as the ligation to circularize a probe.

In some embodiments, one or more post-fixing step is performed after contacting a sample with a binding or labelling agent (e.g., an antibody or antigen binding fragment thereof) for a non-nucleic acid analyte such as a protein analyte. The labelling agent can comprise a nucleic acid molecule (e.g., reporter oligonucleotide) comprising a sequence corresponding to the labelling agent and therefore corresponds to (e.g., uniquely identifies) the analyte. In some embodiments, the labelling agent can comprise a reporter oligonucleotide comprising one or more barcode sequences.

A post-fixing step may be performed using any suitable fixation reagent disclosed herein, for example, 3% (w/v) paraformaldehyde in DEPC-PBS.

(iv) Embedding

As an alternative to paraffin embedding described above, a biological sample can be embedded in any of a variety of other embedding materials to provide structural substrate to the sample prior to sectioning and other handling steps. In some cases, the embedding material can be removed e.g., prior to analysis of tissue sections obtained from the sample. Suitable embedding materials include, but are not limited to, waxes, resins (e.g., methacrylate resins), epoxies, and agar.

In some embodiments, the biological sample can be embedded in a matrix (e.g., a hydrogel matrix). Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 μm to about 2 mm.

Additional methods and aspects of hydrogel embedding of biological samples are described for example in Chen et al., Science 347 (6221): 543-548, 2015, the entire contents of which are incorporated herein by reference.

(v) Staining and Immunohistochemistry (IHC)

To facilitate visualization, biological samples can be stained using a wide variety of stains and staining techniques. In some embodiments, for example, a sample can be stained using any number of stains and/or immunohisto-chemical reagents. One or more staining steps may be performed to prepare or process a biological sample for an assay described herein or may be performed during and/or after an assay. In some embodiments, the sample can be contacted with one or more nucleic acid stains, membrane stains (e.g., cellular or nuclear membrane), cytological stains, or combinations thereof. In some examples, the stain may be specific to proteins, phospholipids, DNA (e.g., dsDNA, ssDNA), RNA, an organelle or compartment of the cell. The sample may be contacted with one or more labeled antibodies (e.g., a primary antibody specific for the analyte of interest and a labeled secondary antibody specific for the primary antibody). In some embodiments, cells in the sample can be segmented using one or more images taken of the stained sample.

In some embodiments, the stain is performed using a lipophilic dye. In some examples, the staining is performed with a lipophilic carbocyanine or aminostyryl dye, or analogs thereof (e.g., DiI, DiO, DIR, DiD). Other cell membrane stains may include FM and RH dyes or immunohistochemical reagents specific for cell membrane proteins. In some examples, the stain may include but is not limited to, acridine orange, Bismarck brown, carmine, Coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, ruthenium red, propidium iodide, rhodamine (e.g., rhodamine B), or safranine or derivatives thereof. In some embodiments, the sample may be stained with haematoxylin and eosin (H&E).

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain. In some embodiments, biological samples can be destained. Any suitable methods of destaining or discoloring a biological sample may be utilized, and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65 (8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(vi) Isometric Expansion

In some embodiments, a biological sample embedded in a matrix (e.g., a hydrogel) can be isometrically expanded. Isometric expansion methods that can be used include hydration, a preparative step in expansion microscopy, as described in Chen et al., *Science* 347 (6221): 543-548, 2015.

Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel). Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., Nat. Methods 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(vii) Crosslinking and De-Crosslinking

In some embodiments, the biological sample is reversibly cross-linked prior to or during an in situ assay. In some aspects, the analytes, polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, a modified probe comprising oligo dT may be used to bind to mRNA molecules of interest, followed by reversible crosslinking of the mRNA molecules.

In some embodiments, the biological sample is immobilized in a hydrogel via cross-linking of the polymer material that forms the hydrogel. Cross-linking can be performed chemically and/or photochemically, or alternatively by any other hydrogel-formation method. A hydrogel may include a macromolecular polymer gel including a network. Within the network, some polymer chains can optionally be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete. In some embodiments, only a portion of crosslinked molecules in the reversibly cross-linked biological sample are de-crosslinked and allowed to migrate.

(viii) Tissue Permeabilization and Treatment

In some embodiments, a biological sample can be permeabilized to facilitate transfer of species (such as probes) into the sample.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods are established. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to open up DNA in a cell for hybridization by a probe. For example, proteinase K treatment may be used to free up DNA with proteins bound thereto.

(ix) Selective Enrichment of RNA Species

In some embodiments, where RNA is the analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by an enzyme (e.g., a polymerase). For example, one or more primer sequences with sequence complementarity to one or more RNAs of interest can be used to amplify the one or more RNAs of interest, thereby selectively enriching these RNAs.

An analyte of interest (such as a protein), bound by a labelling agent or binding agent (e.g., an antibody or epitope binding fragment thereof), wherein the binding agent is conjugated or otherwise associated with a reporter oligonucleotide comprising a reporter sequence that identifies the binding agent, can be targeted for analysis. Probes may be hybridized to the reporter oligonucleotide and ligated in a templated ligation reaction to generate a product for analysis. In some embodiments, gaps between the probe oligonucleotides may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, the assay can further include amplification of templated ligation products (e.g., by multiplex PCR).

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, BMC Genomics, 15 401, (2014), the entire contents of which are incorporated herein by reference). Furthermore, hydroxyapatite chromatography can remove abundant species (e.g., rRNA) (see, e.g., Vandernoot, V. A., cDNA normalization by hydroxyapatite chromatography to enrich transcriptome diversity in RNA-seq applications, Biotechniques, 53 (6) 373-80, (2012), the entire contents of which are incorporated herein by reference).

A biological sample may comprise one or a plurality of analytes of interest. Methods for performing multiplexed assays to analyze two or more different analytes in a single biological sample are provided.

B. Analytes

The methods and compositions disclosed herein can be used to detect and analyze a wide variety of different analytes. In some aspects, an analyte can include any biological substance, structure, moiety, or component to be analyzed. In some aspects, a target disclosed herein may similarly include any analyte of interest. In some examples, a target or analyte can be directly or indirectly detected. In some aspects, the analytes include one of more target nucleic acids.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The analyte may include any biomolecule or chemical compound, including a macromolecule such as a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead directly to the generation of a RCA template (e.g. a circularizable probe). Alternatively, the specific binding partner may be coupled to a nucleic acid, which may be detected using an RCA strategy, e.g., in an assay which uses or generates a circular nucleic acid molecule which can be the RCA template.

Analytes of particular interest may include nucleic acid molecules, such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

(i) Endogenous Analytes

In some embodiments, an analyte herein is endogenous to a biological sample and can include nucleic acid analytes and non-nucleic acid analytes. Methods and compositions disclosed herein can be used to analyze nucleic acid analytes (e.g., using a nucleic acid probe or probe set that directly or indirectly hybridizes to a nucleic acid analyte) and/or non-nucleic acid analytes (e.g., using a labelling agent that comprises a reporter oligonucleotide and binds directly or indirectly to a non-nucleic acid analyte) in any suitable combination.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte is inside a cell or on a cell surface, such as a transmembrane analyte or one that is attached to the cell membrane. In some embodiments, the analyte can be an organelle (e.g., nuclei or mitochondria). In some embodiments, the analyte is an extracellular analyte, such as a secreted analyte. Exemplary analytes include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a tissue sample.

Examples of nucleic acid analytes also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaRNAs), and the long ncRNAs such as Xist and HOTAIR. The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, tRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments described herein, an analyte may be a denatured nucleic acid, wherein the resulting denatured nucleic acid is single-stranded. The nucleic acid may be denatured, for example, optionally using formamide, heat, or both formamide and heat. In some embodiments, the nucleic acid is not denatured for use in a method disclosed herein.

In certain embodiments, an analyte can be extracted from a live cell. Processing conditions can be adjusted to ensure that a biological sample remains live during analysis, and analytes are extracted from (or released from) live cells of the sample. Live cell-derived analytes can be obtained only once from the sample, or can be obtained at intervals from a sample that continues to remain in viable condition.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

In any embodiment described herein, the analyte comprises a target sequence. In some embodiments, the target sequence may be endogenous to the sample, generated in the sample, added to the sample, or associated with an analyte in the sample. In some embodiments, the target sequence is a single-stranded target sequence (e.g., a sequence in a rolling circle amplification product). In some embodiments, the analytes comprise one or more single-stranded target sequences. In one aspect, a first single-stranded target sequence is not identical to a second single-stranded target sequence. In another aspect, a first single-stranded target sequence is identical to one or more second single-stranded target sequence. In some embodiments, the one or more second single-stranded target sequence is comprised in the same analyte (e.g., nucleic acid) as the first single-stranded target sequence. Alternatively, the one or more second single-stranded target sequence is comprised in a different analyte (e.g., nucleic acid) from the first single-stranded target sequence.

(ii) Labelling Agents

In some embodiments, provided herein are methods and compositions for analyzing endogenous analytes (e.g., RNA, ssDNA, and cell surface or intracellular proteins and/or metabolites) in a sample using one or more labelling agents. In some embodiments, an analyte labelling agent may include an agent that interacts with an analyte (e.g., an endogenous analyte in a sample). In some embodiments, the labelling agents can comprise a reporter oligonucleotide that is indicative of the analyte or portion thereof interacting with the labelling agent. For example, the reporter oligonucleotide may comprise a barcode sequence that permits identification of the labelling agent. In some cases, the sample contacted by the labelling agent can be further contacted with a probe (e.g., a single-stranded probe sequence), that hybridizes to a reporter oligonucleotide of the labelling agent, in order to identify the analyte associated with the labelling agent. In some embodiments, the analyte labelling agent comprises an analyte binding moiety and a labelling agent barcode domain comprising one or more barcode sequences, e.g., a barcode sequence that corresponds to the analyte binding moiety and/or the analyte. An analyte binding moiety barcode includes to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein.

In some embodiments, the method comprises one or more post-fixing (also referred to as post-fixation) steps after contacting the sample with one or more labelling agents.

In the methods and systems described herein, one or more labelling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some embodiments, an analyte binding moiety may include any molecule or moiety capable of binding to an analyte (e.g., a biological analyte, e.g., a macromolecular constituent). A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In some embodiments, an analyte binding moiety includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte labelling agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte labelling agents are the same. In some embodiments in which the plurality of analytes includes a single species of analyte, the analyte binding moieties of the plurality of analyte labelling agents are the different (e.g., members of the plurality of analyte labelling agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using sequencing technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31 (2): 708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing.

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (e.g., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte labelling agent comprising an analyte binding moiety that binds to the cell surface protein and an analyte binding moiety barcode that identifies that analyte binding moiety. Results of protein analysis in a sample (e.g., a tissue sample or a cell) can be associated with DNA and/or RNA analysis in the sample.

(iii) Products of Endogenous Analyte and/or Labelling Agent

In some embodiments, provided herein are methods and compositions for analyzing one or more products of an endogenous analyte and/or a labelling agent in a biological sample. In some embodiments, an endogenous analyte (e.g., a viral or cellular DNA or RNA) or a product (e.g., a hybridization product, a ligation product, an extension product (e.g., by a DNA or RNA polymerase), a replication product, a transcription/reverse transcription product, and/or an amplification product such as a rolling circle amplification (RCA) product) thereof is analyzed. In some embodiments, a labelling agent that directly or indirectly binds to an analyte in the biological sample is analyzed. In some embodiments, a product (e.g., a hybridization product, a ligation product, an extension product (e.g., by a DNA or RNA polymerase), a replication product, a transcription/ reverse transcription product, and/or an amplification product such as a rolling circle amplification (RCA) product) of a labelling agent that directly or indirectly binds to an analyte in the biological sample is analyzed.

C. Target Sequences

A target sequence for a probe disclosed herein may be comprised in any analyte disclose herein, including an endogenous analyte (e.g., a viral or cellular nucleic acid), a labelling agent, or a product of an endogenous analyte and/or a labelling agent.

In some aspects, one or more of the target sequences includes one or more barcode(s), e.g., at least two, three, four, five, six, seven, eight, nine, ten, or more barcodes. Barcodes can spatially-resolve molecular components found in biological samples, for example, within a cell or a tissue sample. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI"). In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some embodiments, a barcode includes two or more sub-barcodes that together function as a single barcode. For example, a polynucleotide barcode can include two or more polynucleotide sequences (e.g., sub-barcodes) that are separated by one or more non-barcode sequences. In some embodiments, the one or more barcode(s) can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the polynucleotide.

In any of the preceding implementations, barcodes (e.g., primary and/or secondary barcode sequences) can be analyzed (e.g., detected or sequenced) using any suitable method or technique, including those described herein, such as sequencing by synthesis (SBS), sequencing by ligation (SBL), or sequencing by hybridization (SBH). In some instances, barcoding schemes and/or barcode detection schemes as described in RNA sequential probing of targets (RNA SPOTs), single-molecule fluorescent in situ hybridization (smFISH), multiplexed error-robust fluorescence in situ hybridization (MERFISH) or sequential fluorescence in situ hybridization (seqFISH+) can be used. In any of the preceding implementations, the methods provided herein can include analyzing the barcodes by sequential hybridization and detection with a plurality of labelled probes (e.g., detection probes (e.g., detection oligos) or barcode probes). In some instances, the barcode detection steps can be performed as described in hybridization-based in situ sequencing (HybISS). In some instances, probes can be detected and analyzed (e.g., detected or sequenced) as performed in fluorescent in situ sequencing (FISSEQ), or as performed in the detection steps of the spatially-resolved transcript amplicon readout mapping (STARmap) method. In some instances, signals associated with an analyte can be detected as performed in sequential fluorescent in situ hybridization (seqFISH).

In some embodiments, in a barcode sequencing method, barcode sequences are detected for identification of other molecules including nucleic acid molecules (DNA or RNA) longer than the barcode sequences themselves, as opposed to direct sequencing of the longer nucleic acid molecules. In some embodiments, a N-mer barcode sequence comprises $4^N$ complexity given a sequencing read of N bases, and a much shorter sequencing read may be required for molecular identification compared to non-barcode sequencing methods such as direct sequencing. For example, 1024 molecular species may be identified using a 5-nucleotide barcode sequence ($4^5$=1024), whereas 8 nucleotide barcodes can be used to identify up to 65,536 molecular species, a number greater than the total number of distinct genes in the human genome. In some embodiments, the barcode sequences contained in the probes or RCPs are detected, rather than endogenous sequences, which can be an efficient read-out in terms of information per cycle of sequencing. Because the barcode sequences are pre-determined, they can also be designed to feature error detection and correction mechanisms, see, e.g., U.S. Pat. Pub. 20190055594 and WO2019199579A1, which are hereby incorporated by reference in their entirety.

III. Exemplary Probes and Methods

In some of any of the embodiments, described herein are exemplary probe design, compositions and methods for analyzing a biological sample that involves using a plurality of circularizable probes and a plurality of oligonucleotide probes. Among the provided embodiments include those exemplified in the Examples or those illustrated in the drawings or those described below.

Disclosed herein in some aspects are nucleic acid probes and/or probe sets that are introduced into a cell or used to otherwise contact a biological sample such as a tissue sample. In some aspects, the nucleic acid probes and/or probe sets comprise a hybridization region comprising an interrogatory region, wherein the hybridization region on the probe is capable of hybridizing to a hybridization region on the target nucleic acid, wherein the hybridization region on the target nucleic acid comprises a region of interest. In some aspects, the probes and/or probe sets are designed such that the probes can be circularized by a ligation that is not templated by the target nucleic acid. In some aspects, the probes and/or probe sets are designed such that more than one ligation is required for circularization of the probes. In some aspects, the probes and/or probe sets are designed such that detection specificity and stringency is increased by blocking the hybridization regions in the target nucleic acid and the probe from hybridizing to each other by providing a blocking strand that prevents the hybridization region on the probe from hybridizing to the hybridization region on the target nucleic acid unless the interrogatory region is complementary to the region of interest. In some embodiments, the blocking strand is hybridized to the hybridization region in the probe. In some embodiments, the blocking strand is hybridized to the hybridization region in the target nucleic acid.

The nucleic acid probes and/or probe sets may comprise any of a variety of entities that can hybridize to a nucleic acid, typically by Watson-Crick base pairing, such as DNA, RNA, LNA, PNA, etc. The nucleic acid probes typically contain a targeting sequence that is able to directly or indirectly bind to at least a portion of a target nucleic acid. The nucleic acid probes may be able to bind to a specific target nucleic acid (e.g., an mRNA, or other nucleic acids as discussed herein). In some embodiments, the nucleic acid probes may be detected using a detectable label, and/or by using secondary nucleic acid probes able to bind to the nucleic acid probes. In some embodiments, the nucleic acid probes (e.g., circularizable probes, oligonucleotide probes and/or secondary probes) are compatible with one or more biological and/or chemical reactions. For instance, a nucleic acid probe disclosed herein can serve as a template or primer for a polymerase, a template or substrate for a ligase, a substrate for a click chemistry reaction, and/or a substrate for a nuclease (e.g., endonuclease or exonuclease for cleavage or digestion).

Provided herein are methods involving the use of one or more probes for analyzing one or more target nucleic acid(s), such as a target nucleic acid (for example, a messenger RNA) present in a cell or a biological sample, such as a tissue sample. Also provided are probes, sets of probes, compositions, kits, systems, and devices for use in accordance with the provided methods. In some aspects, the provided methods and systems can be applied to detect, image, quantitate, or determine the presence or absence of one or more target nucleic acid(s) or portions thereof (e.g., presence or absence of sequence variants such as point mutations and SNPs). In some aspects, the provided methods can be applied to detect, image, quantitate, or determine the sequence of one or more target nucleic acid(s), comprising sequence variants such as point mutations and SNPs.

In some aspects, the provided embodiments can be employed for in situ detection and/or sequencing of a target nucleic acid in a cell, e.g., in cells of a biological sample or a sample derived from a biological sample, such as a tissue section on a solid support, such as on a transparent slide.

In some aspects, the provided methods involve a step of contacting, or hybridizing, one or more polynucleotides, such as any of the probes described herein, to a cell or a sample containing a target nucleic acid with a region of interest in order to form a hybridization complex. In some aspects, the provided methods comprise one or more steps of ligating the polynucleotides, for instance of ligating the probes to form a circular probe. In some aspects, the provided methods involve a step of amplifying one of the polynucleotides (e.g., a ligated circular probe), to generate an amplification product. In some aspects, the provided methods involve a step of detecting and/or determining the sequence of all or a portion of the amplification product (for example, of one or more barcodes contained in the amplification product) and/or one or more of the polynucleotides, for instance the circular probe, with or without amplification, for instance any barcodes contained therein. In some aspects, the provided methods involve performing one or more of the steps described herein, simultaneously and/or sequentially.

In some aspects, provided herein are in situ assays using microscopy as a readout, e.g., nucleic acid sequencing, hybridization, or other detection or determination methods involving an optical readout. In some aspects, detection or determination of a sequence of one, two, three, four, five, or more nucleotides of a target nucleic acid is performed in situ in a cell in an intact tissue. In some aspects, detection or determination of a sequence is performed such that the localization of the target nucleic acid (or product or a derivative thereof associated with the target nucleic acid) in the originating sample is detected. In some embodiments, the assay comprises detecting the presence or absence of an amplification product or a portion thereof (e.g., RCA product). In some embodiments, a method for spatially profiling analytes such as the transcriptome or a subset thereof in a biological sample is provided. Methods, compositions, kits, devices, and systems for these in situ assays and in situ detection are provided. In some embodiments, a provided method is quantitative and preserves the spatial information within a tissue sample without physically isolating cells or using homogenates. In some embodiments, the present disclosure provides methods for high-throughput profiling one or more single nucleotides of interest in a large number of targets in situ, such as transcripts and/or DNA loci, for detecting and/or quantifying nucleic acids in cells, tissues, organs or organisms.

In some embodiments, a circularizable probe disclosed herein includes a barcode sequence. In some instances, the design of the circularizable probe and an oligonucleotide probe for analyzing a target nucleic acid(s) that comprises hybridization regions that can hybridize to each other (e.g., based on sequence complementarity) or to portions of the target nucleic acids provides specificity for ligation and amplification. The circularizable probe includes a barcode region corresponding to the target nucleic acid or a sequence thereof, and the oligonucleotide probe comprises sequences that can be used as a splint to ligate the circularizable probe and permit rolling circle amplification (RCA) of the circularized probe, when sequences of the oligonucleotide probe is complementary to the barcode region. If the sequences are not complementary, the ligation and/or RCA does not proceed, thereby increasing the specificity of binding and amplification, and reducing non-specific baseline ligation and amplification. Provided herein are modifications and variations of such circularizable probes and oligonucleotide probes.

The barcode sequences, if present, may be of any length. If more than one barcode sequence is used, the barcode sequences may independently have the same or different lengths, such as at least 5, at least 10, at least 15, at least 20, at least 25, at least 30, at least 35, at least 40, at least 50 nucleotides in length. In some embodiments, the barcode sequence may be no more than 120, no more than 112, no more than 104, no more than 96, no more than 88, no more than 80, no more than 72, no more than 64, no more than 56, no more than 48, no more than 40, no more than 32, no more than 24, no more than 16, or no more than 8 nucleotides in length. Combinations of any of these are also possible, e.g., the barcode sequence may be between 5 and 10 nucleotides, between 8 and 15 nucleotides, etc.

The barcode sequence may be arbitrary or random. In certain cases, the barcode sequences are chosen so as to reduce or minimize homology with other components in a sample, e.g., such that the barcode sequences do not themselves bind to or hybridize with other nucleic acids suspected of being within the cell or other sample. In some embodiments, between a particular barcode sequence and another sequence (e.g., a cellular nucleic acid sequence in a sample or other barcode sequences in probes added to the sample), the homology may be less than 10%, less than 8%, less than 7%, less than 6%, less than 5%, less than 4%, less than 3%, less than 2%, or less than 1%. In some embodiments, the homology may be less than 20, 19, 18, 17, 16, 15, 14, 13, 12, 11, 10, 9, 8, 7, 6, 5, 4, 3, or 2 bases, and in some embodiments, the bases are consecutive bases.

In some aspects, the provided methods are employed for in situ analysis of target nucleic acids, for example for in situ sequencing or multiplexed analysis in intact tissues or a sample with preserved cellular or tissue structure. In some aspects, the provided methods can be used to detect or determine the identity or amount in situ of single nucleotides of interest in target nucleic acids, for instance of single nucleotide polymorphisms of genes of interest.

Figure 1B:
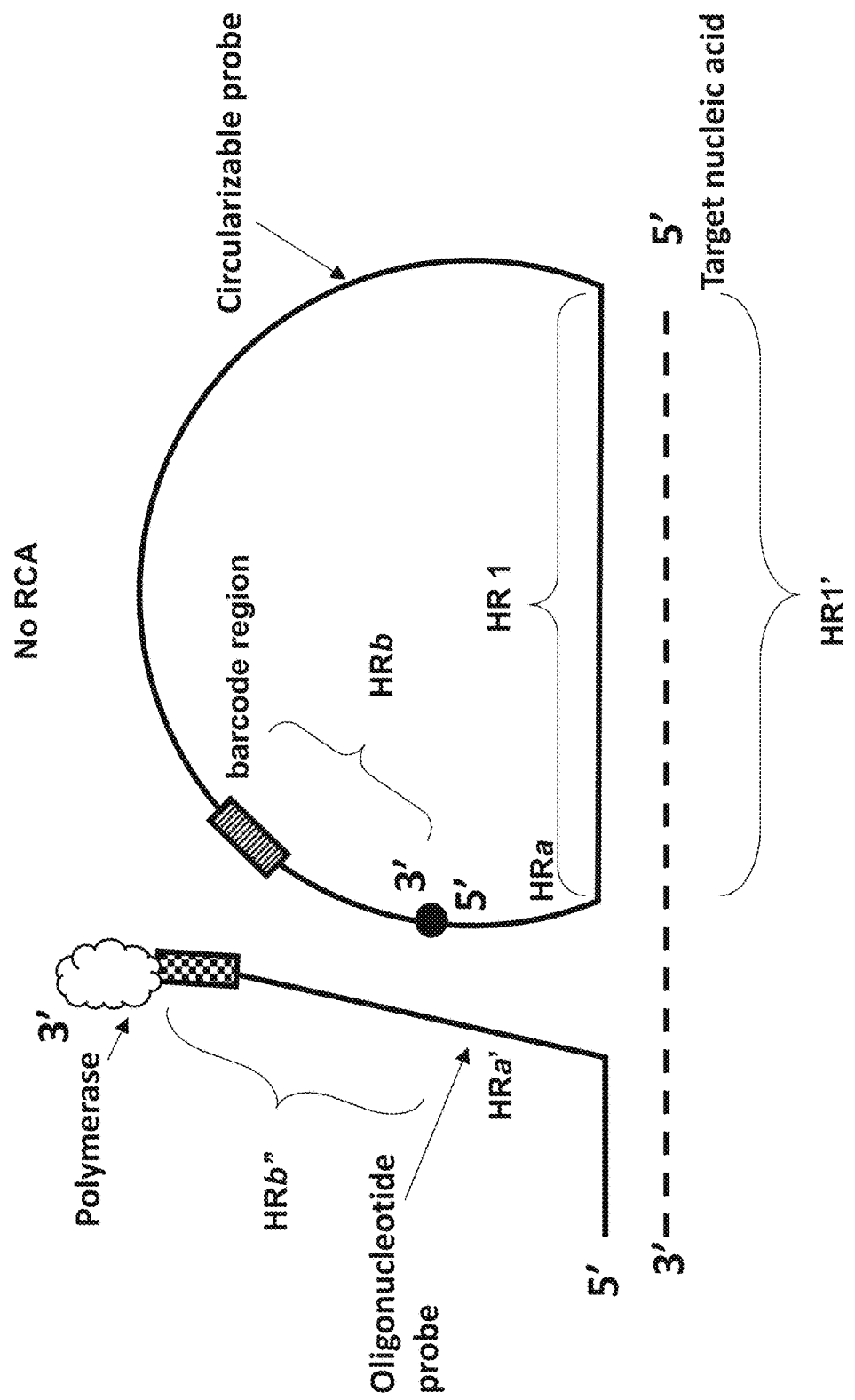

In some aspects, the provided methods are for using a circularizable probe and a oligonucleotide probe for analyzing a biological sample. For example, FIG. 1A shows: an exemplary circularizable probe comprising hybridization regions HRa, HR1, and HRb, where HRb comprises a barcode region and optionally a 3' splint hybridization region (which is 3' to the barcode region); and an exemplary oligonucleotide probe comprising hybridization regions HR2, HRa', and HRb'. HRb' may comprises a barcode region and optionally a region complementary to the 3' splint hybridization region of HRb. As shown in FIG. 1A, rolling circle amplification (RCA) can occur when the circularizable probe and oligonucleotide probe hybridize to the target nucleic acid, and a sequence of HRb' (e.g., a first complementary barcode region in HRb' that is complementary to the barcode region in HRb) is complementary to the barcode region of HRb. The 5' end of and the 3' end of the circularizable probe can be ligated using the oligonucleotide probe as a splint, and the circularizable probe is circularized. When the barcode regions in the oligonucleotide probe and the circularized probe are complementary, HRb or a portion thereof can prime RCA of the circularized probe. In some aspects, as shown in FIG. 1B, if the barcode regions or portions thereof in the oligonucleotide probe and the circularized probe are not complementary (e.g., at least a portion of the barcodes in HRb and HRb" are not complementary), RCA does not occur because hybridization of the non-complementary HRb" sequence (e.g., the barcode region in HRb") to the circularized probe is not sufficient to prime the amplification. In some aspects, the oligonucleotide probes can comprise a modification that protects HRb' and/or HRb" from 3'→5' exonuclease degradation. Optionally, the modification allows primer extension (e.g., by Phi29) of HRb' and/or HRb" or a portion thereof and does not need to be removed for RCA to take place. In some cases, the oligonucleotide probe shown in FIG. 1B in nonspecifically bound to the target nucleic acid—in other words, the oligonucleotide probe may not comprise HR2 which is complementary to HR2' in the target nucleic acid. Such nonspecific hybridization may generate a false positive signal using conventional SNAIL, and a method disclosed herein can be used to eliminate the false positive signal since the oligonucleotide probe shown in FIG. 1B does not match the circularized probe and does not prime RCA.

In some of any of the provided embodiments, the oligonucleotide probe and/or the circularizable probe contains one or more modifications. In some aspects, the oligonucleotide probe comprises one or more modifications, for example in HRb'. In some aspects, the oligonucleotide probe comprises one or more modifications that protect HRb' from 3'→5' exonuclease degradation. In some aspects, the one or more modification prevents non-specific ligation and/or priming, and can increase the specificity of the provided methods and probes.

Figure 2A:
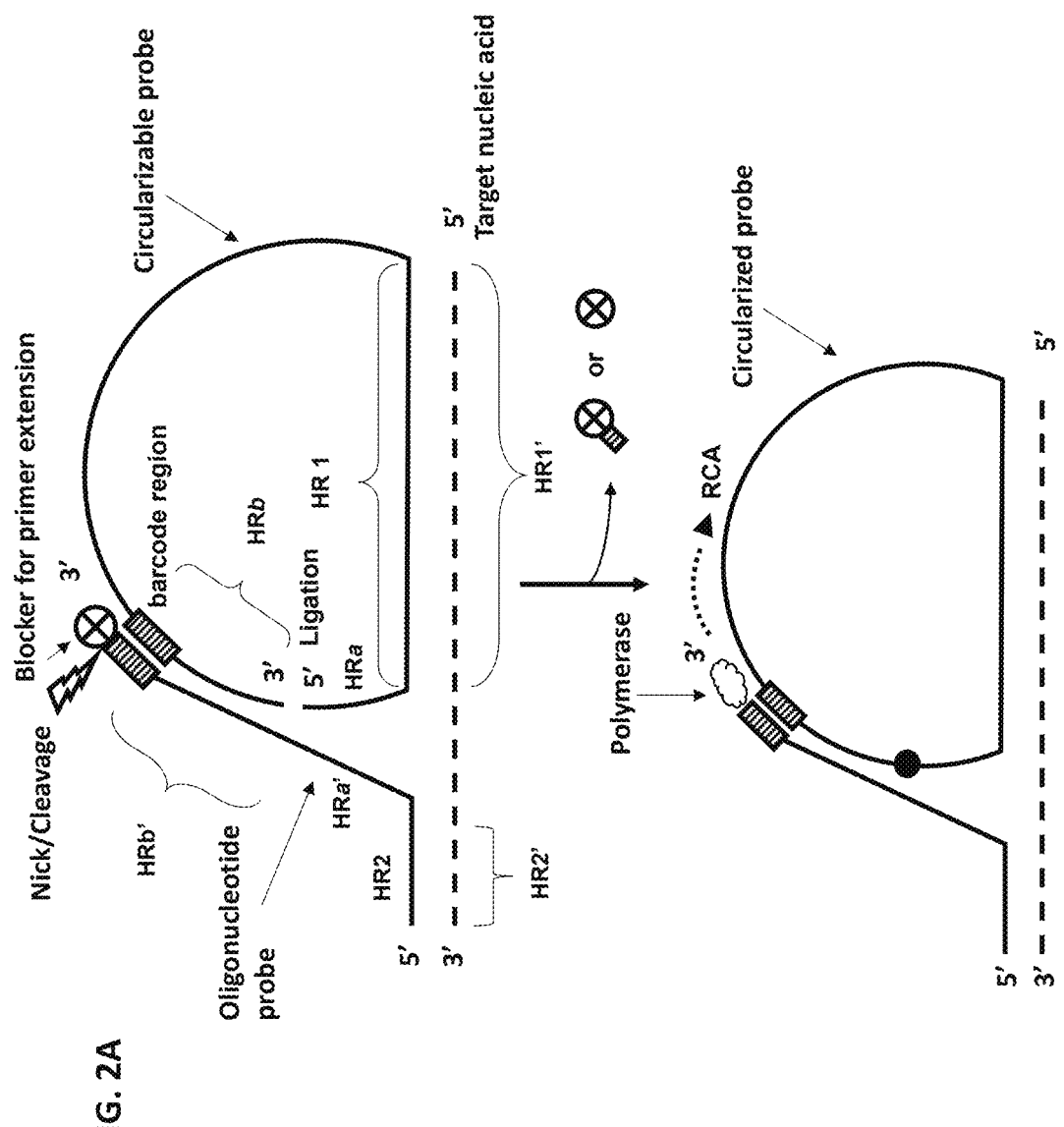
FIG. 2A and FIG. 2B depict exemplary design and methods for oligonucleotide probes with exemplary modifications that protect HRb' and/or HRb" from 3→5' exonuclease degradation.
Figure 2B:
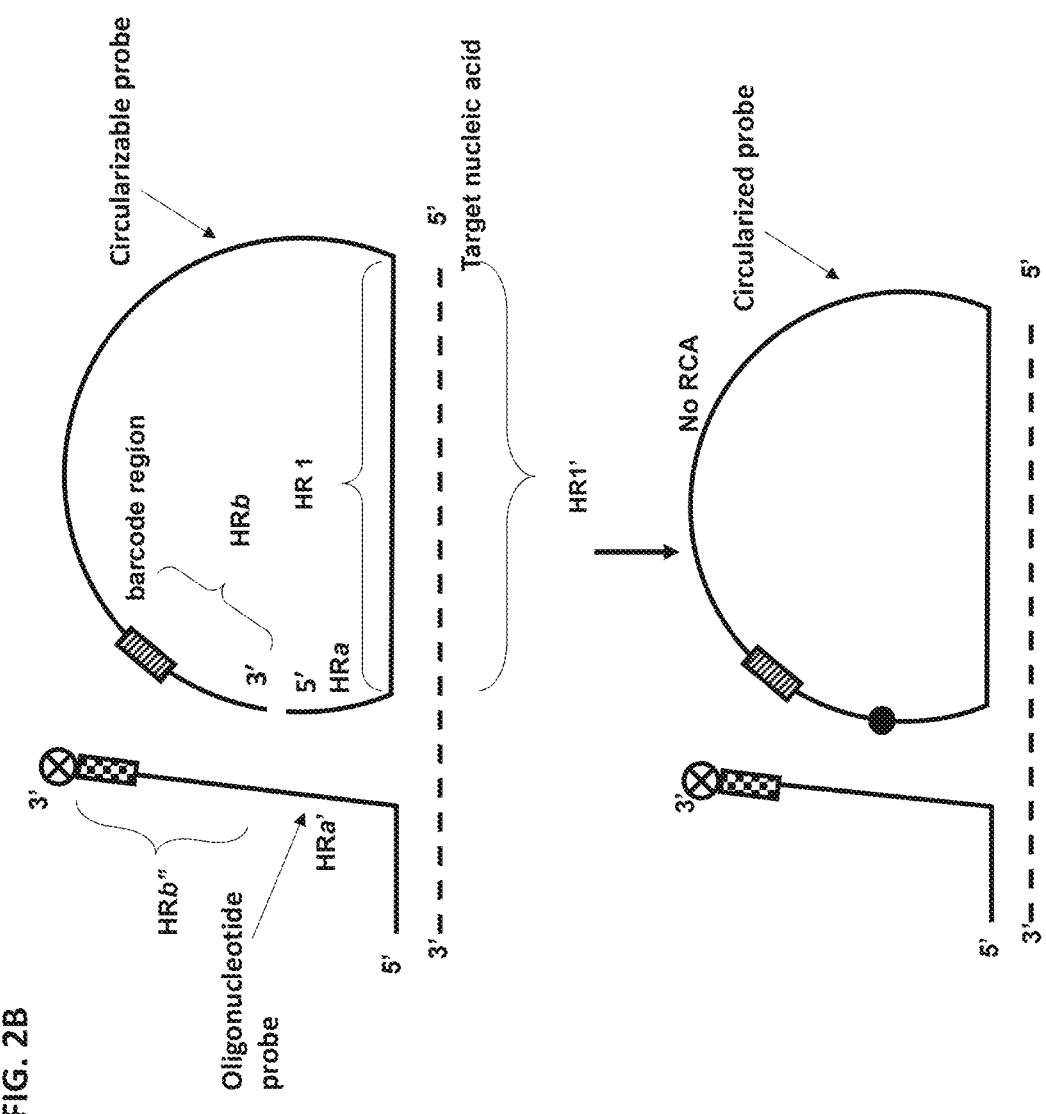

FIG. 2A and FIG. 2B depict exemplary design and methods for oligonucleotide probes with exemplary modifications that protect HRb' and/or HRb" from 3'→5' exonuclease degradation. In some aspects, the modification prevents priming by a polymerase on the 3' end. In FIG. 2A, the circularizable probe and oligonucleotide probe hybridize to the target nucleic acid, and HRa of the circularizable probe hybridizes to HRa' of the oligonucleotide probe. Optionally, HRb may comprise a 3' splint hybridization region (3' to the barcode region) that hybridizes to its complementary region in HRb' of the oligonucleotide probe. When the barcode region of HRb' is complementary to the barcode region of HRb, the oligonucleotide probe can be nicked at a location (e.g., at a specific sequence) with an enzyme that cleaves the oligonucleotide probe but not the circularized or circularizable probe (depending on whether circularization of the circularizable probe occurs before or after the nicking/cleaving), freeing the oligonucleotide probe from the modification that blocks primer extension. The 5' end of and the 3' end of the circularizable probe can be ligated using the oligonucleotide probe as a splint, and the circularizable probe can be circularized before or after the nicking/cleaving to remove the modification that blocks primer extension. RCA can be primed using the 3' end of the nicked/cleaved oligonucleotide probe (e.g., HRb' or a portion thereof, in particular, the barcode region in HRb' or a portion of the barcode region) as a primer. When the barcode regions in the oligonucleotide probe and the circularized probe are not complementary, the oligonucleotide probe may not be able to prime RCA of the circularized probe. In some aspects, as shown in FIG. 2B, if at least a portion of HRb and HRb" are not complementary, for example, the barcode region of HRb" is not complementary to the barcode region of HRb, RCA does not occur because the non-complementary barcode region of HRb" is not cleaved, and the modification prevents RCA from occurring. In addition, hybridization of the non-complementary HRb" sequence (e.g., the barcode region in HRb") to the circularized probe may not be sufficient to prime the amplification even if the modification does not block primer extension. In some cases, the oligonucleotide probe shown in FIG. 2B in nonspecifically bound to the target nucleic acid—in other words, the oligonucleotide probe may not comprise HR2 which is complementary to HR2' in the target nucleic acid. Such nonspecific hybridization may generate a false positive signal using conventional SNAIL, and a method disclosed herein can be used to eliminate the false positive signal since the oligonucleotide probe shown in FIG. 2B does not match the circularized probe and does not prime RCA.

In some embodiments, the one or more modifications protect the 3' sequences, for example the 3' end of HRb', from 3'→5' exonuclease degradation by a polymerase. In some embodiments, the one or more polymerases are employed in the provided methods, for example, for primer extension and/or amplification, e.g., RCA. In some embodiments, the polymerase comprises a modified recombinant Phi29-type polymerase. In some embodiments, Phi29 possesses a 3'→5' exonuclease (proofreading) activity acting preferentially on single-stranded DNA or RNA. In some embodiments, the polynucleotide (e.g., oligonucleotide probe or a separate primer) which functions as an RCA primer can be 3'-modified. In some embodiments, the polynucleotide can be 3' thiophosphate-protected, which protects the polynucleotide from 3'→5' exonuclease degradation by the polymerase while allowing priming by the polymerase. In some embodiments, the polynucleotide can comprise a 3'-tail of sufficient length in order to protect the sequence that functions as RCA primer from degradation by Phi29. In some embodiments, the 3'-end tail can be gradually digested until the remaining part can be converted to RCA primer and is extended along the circular template via the polymerase activity of Phi29.

Figure 3A:
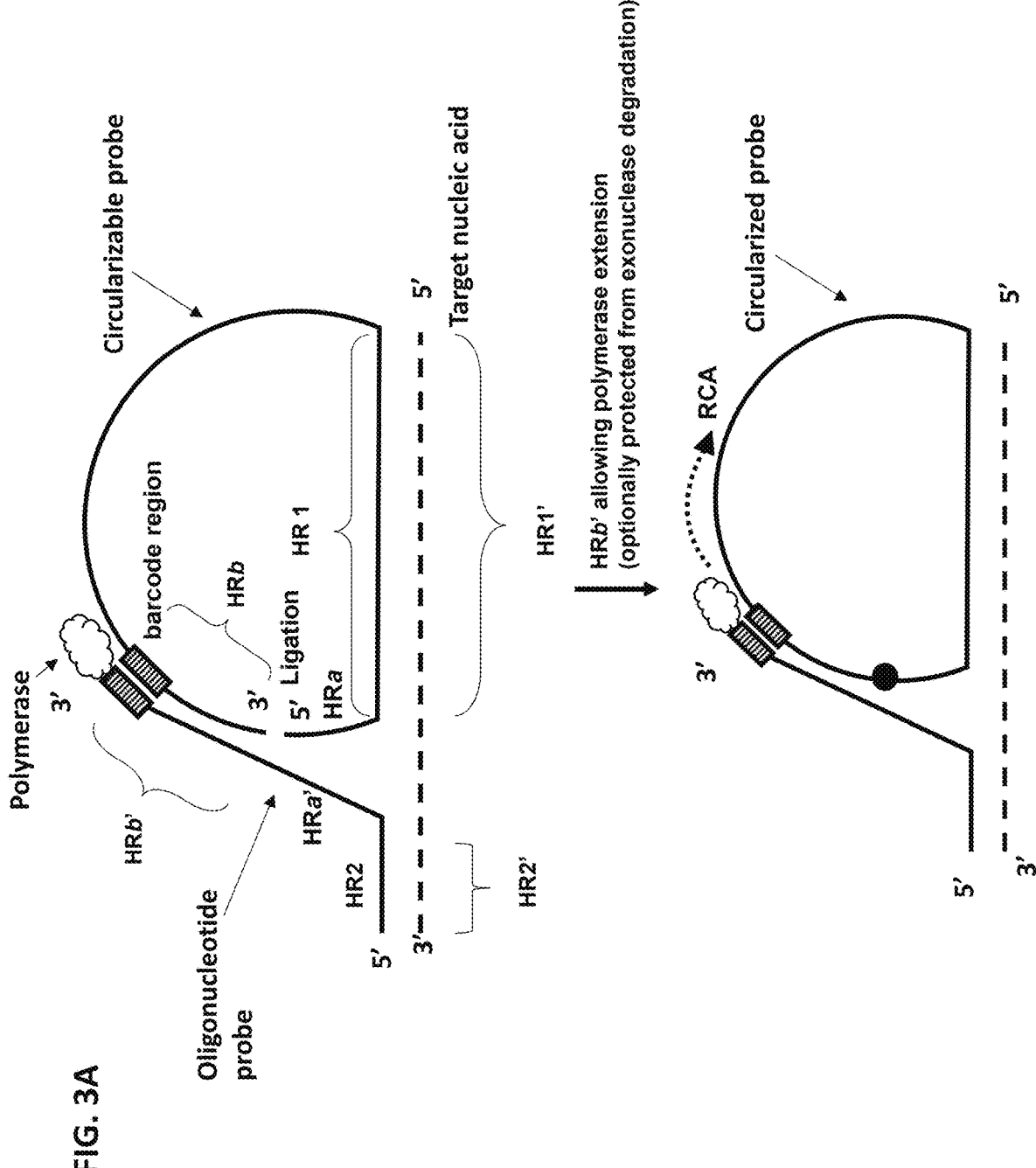
FIG. 3A and FIG. 3B depict exemplary design and methods for oligonucleotide probes that can be cleaved by an enzyme that cleaves a non-complementary HRb' sequence or a portion thereof of the oligonucleotide probe and/or HRb of the circularizable probe.
Figure 3B:
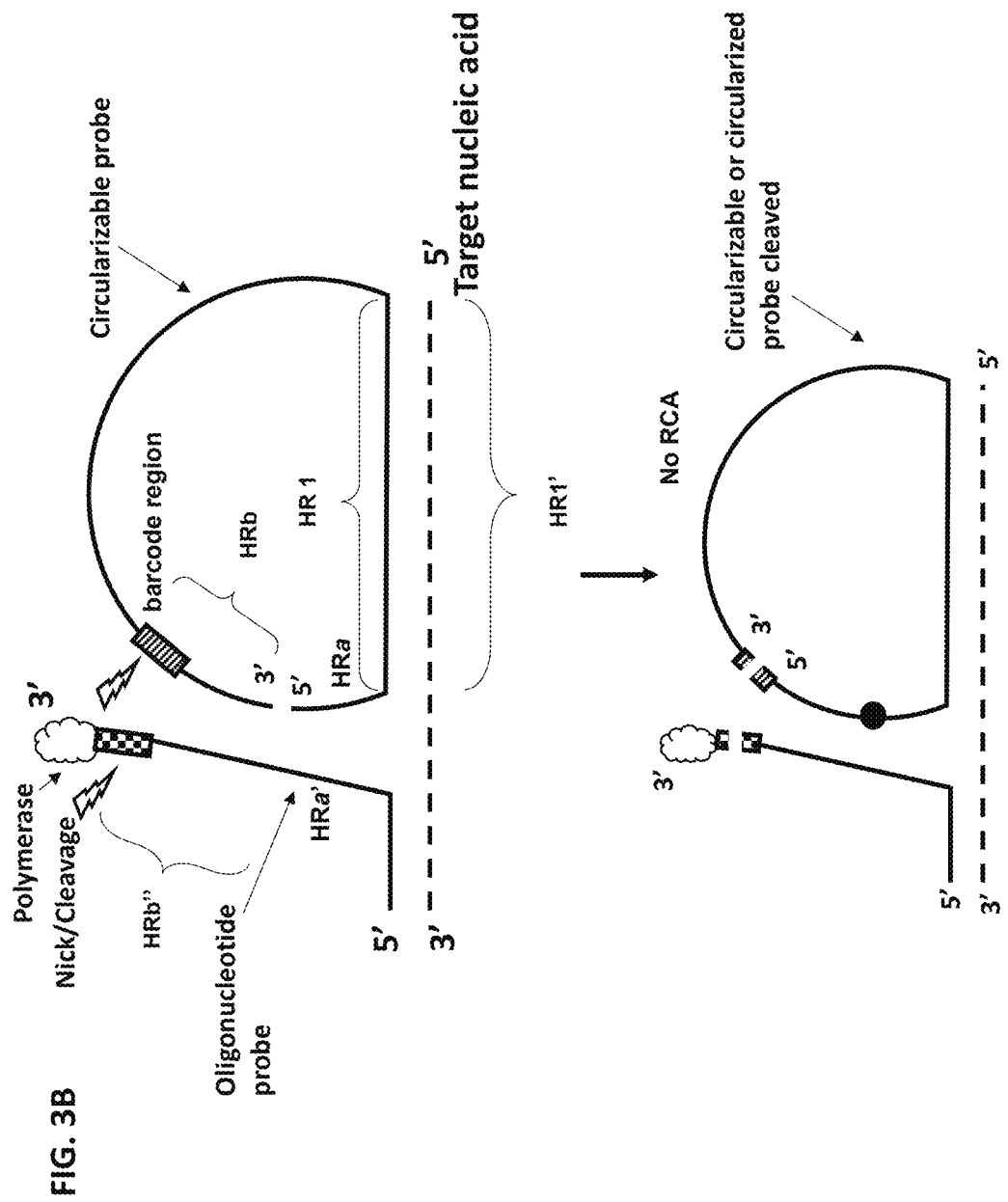

As shown in FIG. 3A, the circularizable probe and oligonucleotide probe hybridize to the target nucleic acid, and rolling circle amplification (RCA) can occur when a sequence (e.g., barcode) of HRb' is complementary to the barcode region of HRb. In some aspects, as shown in FIG. 3B, a barcode region of HRb" of the oligonucleotide probe is not complementary to the barcode region of HRb of the circularizable probe, and the enzyme can nick the oligonucleotide probe or the circularizable or circularized probe or both, and no RCA occurs. In some aspects, at least a portion of the barcode regions remains single-stranded and is cleaved, thereby preventing generation of the circularized probe and/or linearizing the circularized probe to prevent generation of the RCA product. In some cases, the oligonucleotide probe shown in FIG. 3B in nonspecifically bound to the target nucleic acid—in other words, the oligonucleotide probe may not comprise HR2 which is complementary to HR2' in the target nucleic acid. Such nonspecific hybridization may generate a false positive signal using conventional SNAIL, and a method disclosed herein can be used to eliminate the false positive signal since the oligonucleotide probe shown in FIG. 3B does not match the circularized probe. The oligonucleotide probe does not generate an RCA signal and/or the circularizable or circularized probe is cleaved.

In some embodiments, the one or more modifications that protect the 3' sequences, for example the 3' end of HRb', from 3'→5' exonuclease degradation by a polymerase while allowing priming by the polymerase. In some embodiments, the one or more modifications comprise a terminal nucleotide modification and/or an internal modification. In some embodiments, the one or more modifications can include, but are not limited to, a 3' thiophosphate protection, a phosphorothioate bond, a 2'-modified nucleoside, or an inverted deoxythymidine (inverted dT) base. In some embodiments, the one or more modifications can include, but are not limited to, a 2'-O-methyl (2'OMe) nucleosides, 2'-O-methoxyethyl (MOE) nucleosides, 2'-fluoro bases, 3'phosphorylation, phosphoramidite C3 Spacer, 3'-inverted dT, 5-methyl-substituted dT, Fluorescein dT, or deoxyuridine. In some embodiments, the one or more modifications can include 2' O-Methyl RNA.

In some embodiments, the oligonucleotide can comprise one or more modifications that block priming by a polymerase on the 3' end. In some embodiments, the one or more modifications that blocks priming by a polymerase is cleaved or removed by an enzyme or by other means, to permit priming of the amplification, e.g., RCA. In some aspects, the block is removed if a sequence of HRb' and the barcode region of HRb are complementary, e.g., the sequence of HRb' comprises a first complementary barcode region that is complementary to the barcode region of HRb or portion thereof.

In some embodiments, the one or more modifications comprise one or more uracil-containing residues and/or nuclease cleavage sites cleavable by an enzyme. In some aspects, the one or more modification comprises a uracil-containing residue and a portion of the oligonucleotide probe, such as a 3' portion of HRb', is cleaved by a uracil-specific excision reagent. In some aspects, the complementary barcode region of the oligonucleotide probe is cleaved by a uracil-DNA glycosylase (UDG) and/or an endonuclease. In some aspects, the endonuclease is Endonuclease VIII. In some aspects, the portion of HRb' that is cleaved off is no more than 16, no more than 14, no more than 12, no more than 10, no more than 8, no more than 6, or no more than 4 nucleotides in length. In some embodiments, a portion of the oligonucleotide probe, such as a 3' portion of HRb' comprises, one or more uracil-containing residues and/or nuclease cleavage sites cleavable by an enzyme, and if a sequence of HRb' and the barcode region of HRb are not complementary, e.g., the sequence of HRb' is a second complementary barcode region that is not complementary to the barcode region of HRb, the complementary barcode region of the circularizable probe is not cleaved by the enzyme.

In some aspects, the enzyme can nick the oligonucleotide probe, the circular probe, or both. In some aspects, the enzyme can be a Type II restriction enzyme. In some embodiments, Type II restriction enzymes include, but is not limited to, AvaII, HaeII, DdeI, AluI, Sau3 AI, AccII, TthHB8I and HapII.

In some embodiments, a probe disclosed herein (e.g., a circularizable probe) can comprise a 5' flap or a 3' flap, which may be recognized by a structure-specific cleavage enzyme, e.g., an enzyme capable of recognizing the junction between single-stranded 3' or 5' overhang and a DNA duplex and cleaving the single-stranded overhang. In some aspects, the branched three-strand structure which is the substrate for the structure-specific cleavage enzyme may be formed by 5' end of one probe part and the 3' end of another probe part when both have hybridized to the target nucleic acid molecule, as well as by the 5' and 3' ends of a one-part probe. Exemplary enzymes for such cleavage include Flap endonucleases (FENS), which are a class of enzymes having endonucleolytic activity and being capable of catalyzing the hydrolytic cleavage of the phosphodiester bond at the junction of single- and double-stranded DNA.

Figure 5A:
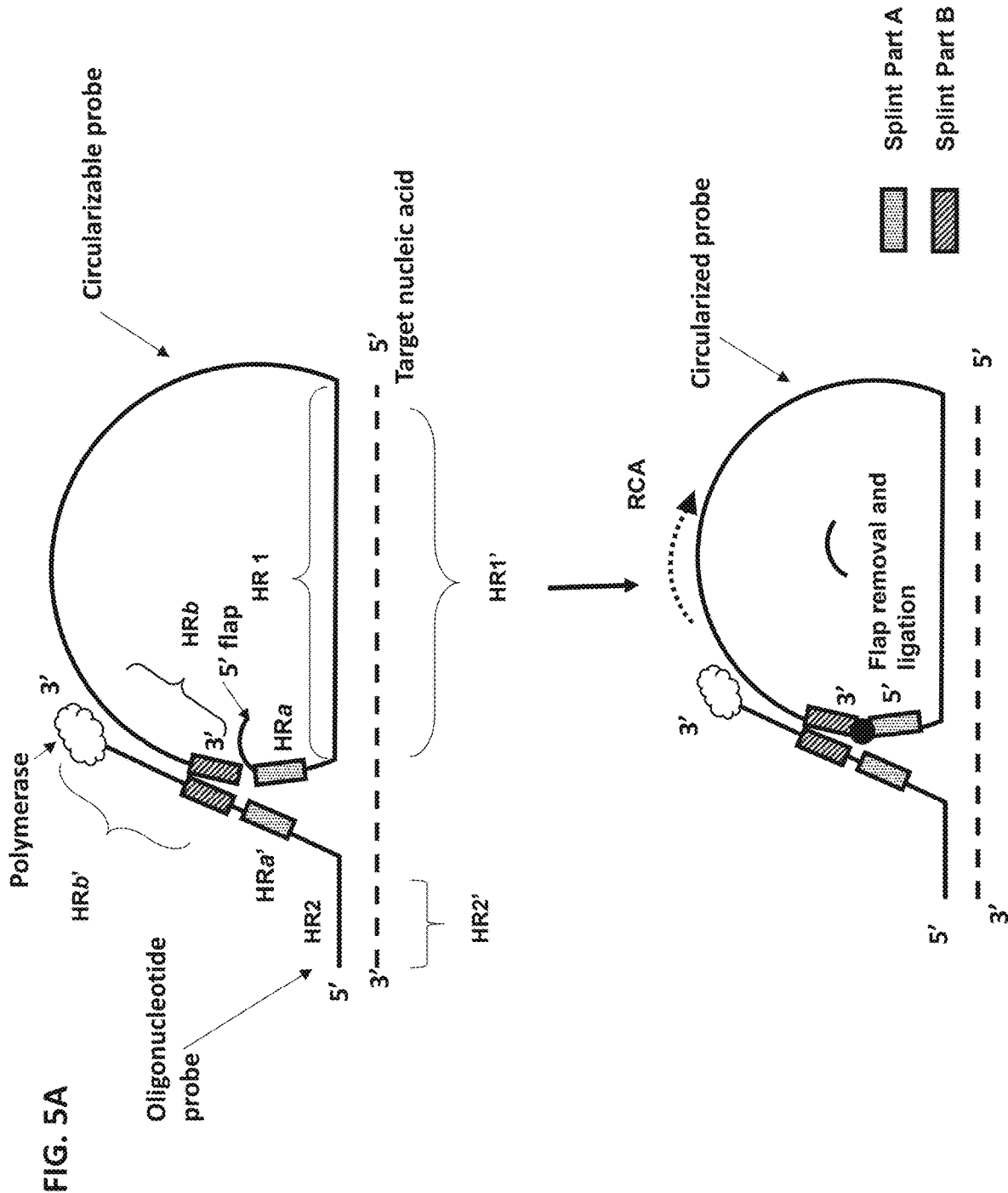
FIG. 5A and FIG. 5B depict exemplary design and method for analyzing a biological sample that employ an oligonucleotide probe as a splint to circularize and amplify a circularizable probe with a 5' flap.
Figure 5B:
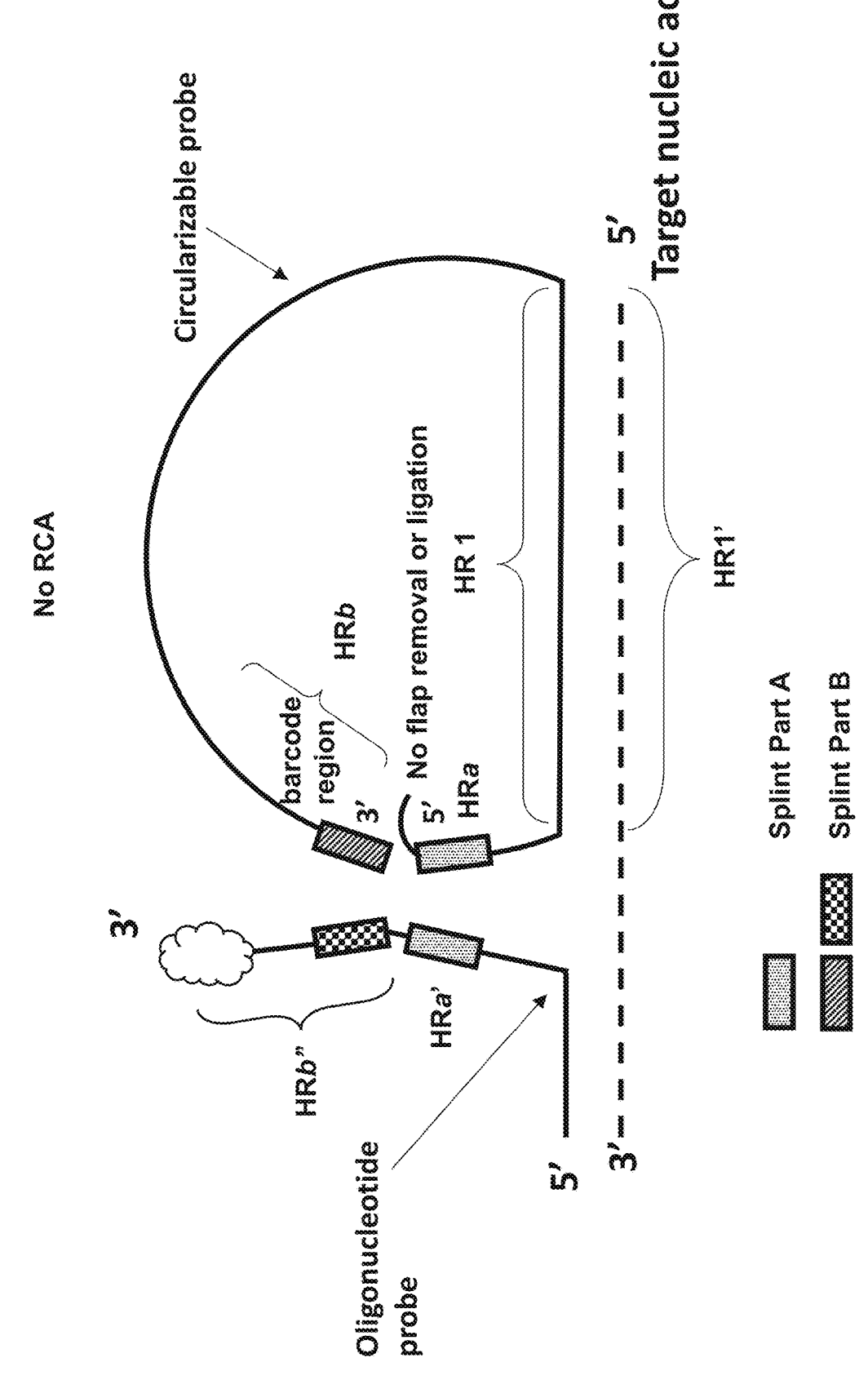

As shown in FIG. 5A, the circularizable probe comprises a sequence 5' to HRa that forms a 5' flap that does not hybridize to the oligonucleotide probe. When the circularizable probe and oligonucleotide probe hybridize to the target nucleic acid, and the barcode region in HRb is complementary to HRb' or a portion thereof, the 5' flap is removed by an endonuclease or a polymerase, and the circularizable probe is circularized by ligating HRa and HRb using the oligonucleotide probe as a splint. The oligonucleotide probe or a separate primer can be used to prime RCA of the circularized probe. In some aspects, as shown in FIG. 5B, when the barcode region in HRb is complementary to HRb" or a portion thereof, the 5' flap of the circularizable probe is not cleaved, the 5' flap prevents ligation of HRa and HRb and circularization, and no RCA occurs. In some cases, the oligonucleotide probe shown in FIG. 5B in nonspecifically bound to the target nucleic acid—in other words, the oligonucleotide probe may not comprise HR2 which is complementary to HR2' in the target nucleic acid. Such nonspecific hybridization may generate a false positive signal using conventional SNAIL, and a method disclosed herein can be used to eliminate the false positive signal since the oligonucleotide probe shown in FIG. 5B does not match the circularized probe. The circularizable probe cannot be ligated using the oligonucleotide probe as a splint. Splint Part A can be a common or universal region among pairs of oligonucleotide probes and circularizable probes targeting different analytes, such as different target nucleic acids. Splint Part B can be analyte-specific, for example, a gene-specific barcode region comprising one or more barcodes. FIG. 5A and FIG. 5B show Splint Part A is 5' to Splint Part B, but the locations of Splint Part A and Splint Part B may be switched, e.g., in the oligonucleotide probe, Splint Part A can be 3' to Splint Part B.

In some embodiment, cleavage of the additional sequence 3' or 5' to the hybridization regions is performed by a structure-specific cleavage enzyme, e.g. a Flap endonuclease. Exemplary Flap endonucleases are described in Ma et al. 2000. JB (275, 24693-24700 and in US 2020/0224244 and may include *P. furiosus* (Pfu), *A. fulgidus* (Afu), *M. jannaschii* (Mja) or *M. thermoautotrophicum* (Mth). In some embodiments, an enzyme capable of recognizing and degrading a single-stranded oligonucleotide having a free 5' end may be used to cleave an additional sequence (5' flap) from a structure, as described above. In some aspects, an enzyme having 5' nuclease activity may be used to cleave a 5' additional sequence. Such 5' nuclease activity may be 5' exonuclease and/or 5' endonuclease activity. A 5' nuclease enzyme is capable of recognizing a free 5' end of a single-stranded oligonucleotide and degrading said single-stranded oligonucleotide. A 5' exonuclease degrades a single-stranded oligonucleotide having a free 5' end by degrading the oligonucleotide into constituent mononucleotides from its 5' end. A 5' endonuclease activity may cleave the 5' flap sequence internally at one or more nucleotides. Further, a 5' nuclease activity may take place by the enzyme traversing the single-stranded oligonucleotide to a region of duplex once it has recognized the free 5' end, and cleaving the single-stranded region into larger constituent nucleotides (e.g. dinucleotides or trinucleotides), or cleaving the entire 5' single-stranded region, e.g. as described in Lyamichev et al. 1999. *PNAS* 96, 6143-6148 for Taq DNA polymerase and the 5' nuclease thereof. In some aspects, exemplary enzymes having 5' nuclease activity include Exonuclease VIII, or a native or recombinant DNA polymerase enzyme from *Thermus aquaticus* (Taq), *Thermus thermophilus* (Tth) or *Thermus flavus*, or the nuclease domain therefrom.

In some embodiments, the 5' flap of the circularizable probe is cleaved by an endonuclease or a polymerase, for example, when the barcode region is complementary to the second complementary barcode region, thereby generating a molecule without the 5' flap. In some embodiments, the endonuclease for cleaving the 5' flap is a flap endonuclease 1 (FEN1) and the polymerase is a *Thermus thermophilus* (Tth) polymerase.

In some embodiments, the 5' flap or the 3' flap is cleaved or removed from the 5' ends or 3' ends of the circularizable probe based on an invasion mechanism (see, e.g., Krzywkowski et al. Nucleic Acids Research 2017, 45 (18): e161; Krzywkowski et al. RNA 2019, 25 (1): 82-89). In some aspects, for a traditional invader configuration, the 3' terminal base displaces the first base in the flap from the invasive junction, and competes for hybridization to the position on the complementary nucleic acid (e.g., sequences on the oligonucleotide probe). In alternative aspects, the discriminatory base is localized in the 5' end, at a single base distance from the traditional invasive junction. In some aspects, an invader structure is formed if a matching terminal base hybridizes with a template. When the polymerase (e.g., *Thermus aquaticus* (Taq) polymerase) activates, the matching hybridized terminal base in the traditional hybridization configuration, the flap is displaced, the 5' phosphate is exposed and a discriminatory base (N') is positioned in the 3' terminal base. In alternative aspects, complementarity between the 5' arm and the complementary sequence allows for formation of an invader structure. After activation, phosphorylated discriminatory base (N') is localized on the 5' terminus. In some aspects, when a mismatching terminal base is annealed to the target, invader structure formation and activation of invasion are compromised. In some cases, a combination of an imperfect 3' arm invasion (traditional configuration) and a lack of 5' arm complementarity renders the probe non-functional. In some aspects, misaligned bases in the alternative approach can generate a single nucleotide gap or a 5' mismatch upon activation.

In some embodiments, the exonuclease activity can be controlled by catalytic cofactors. In some embodiments, due to the absence of one or more catalytic cofactors, the presence of one or more chelating agents for the catalytic cofactors, and/or the presence of one or more non-catalytic cofactors, the exonuclease activity of Phi29 may be effectively inhibited in the binding mixture or OFF buffer such that no 3' protective modification or 3'-tail is necessary. In some embodiments, the polynucleotide (e.g., an exogenously added primer or a target nucleic acid in the sample) can have a free 3' hydroxyl group available for nucleotide incorporation by Phi29. In some embodiments, when the sample is contacted with a primer extension reaction mixture comprising a catalytic di-cation (such as $Mg^{2+}$ and/or $Mn^{2+}$), a non-catalytic cation (such as $Ca^{2+}$, $Zn^{2+}$, $Co^{2+}$, $Ni^{2+}$, $Eu^{2+}$, $Sr^{2+}$, $Ba^{2+}$, $Fe^{2+}$, and/or $Eu^{2+}$) bound to Phi29 is displaced, thereby activating the 5'→3' polymerase activity and the 3'→5' exonuclease (proofreading) activity of Phi29.

Exemplary designs and methods provided herein include various embodiments as exemplified in the Examples. Further, additional examples include one that involves ligating HRa and HRb of the circularizable probe using the oligonucleotide probe as a splint, in which the circularizable probe comprises HRb, HR1, and HRa in the 5' to 3' direction, and the oligonucleotide probe comprises HR2, HRb', and HRa' in the 5' to 3' direction. In some of such embodiments, when the barcode region is not complementary to a second complementary barcode region, HRb does not hybridize to the oligonucleotide probe, thereby preventing ligation of HRa and HRb and circularization of the circularizable probe.

Figure 4A:
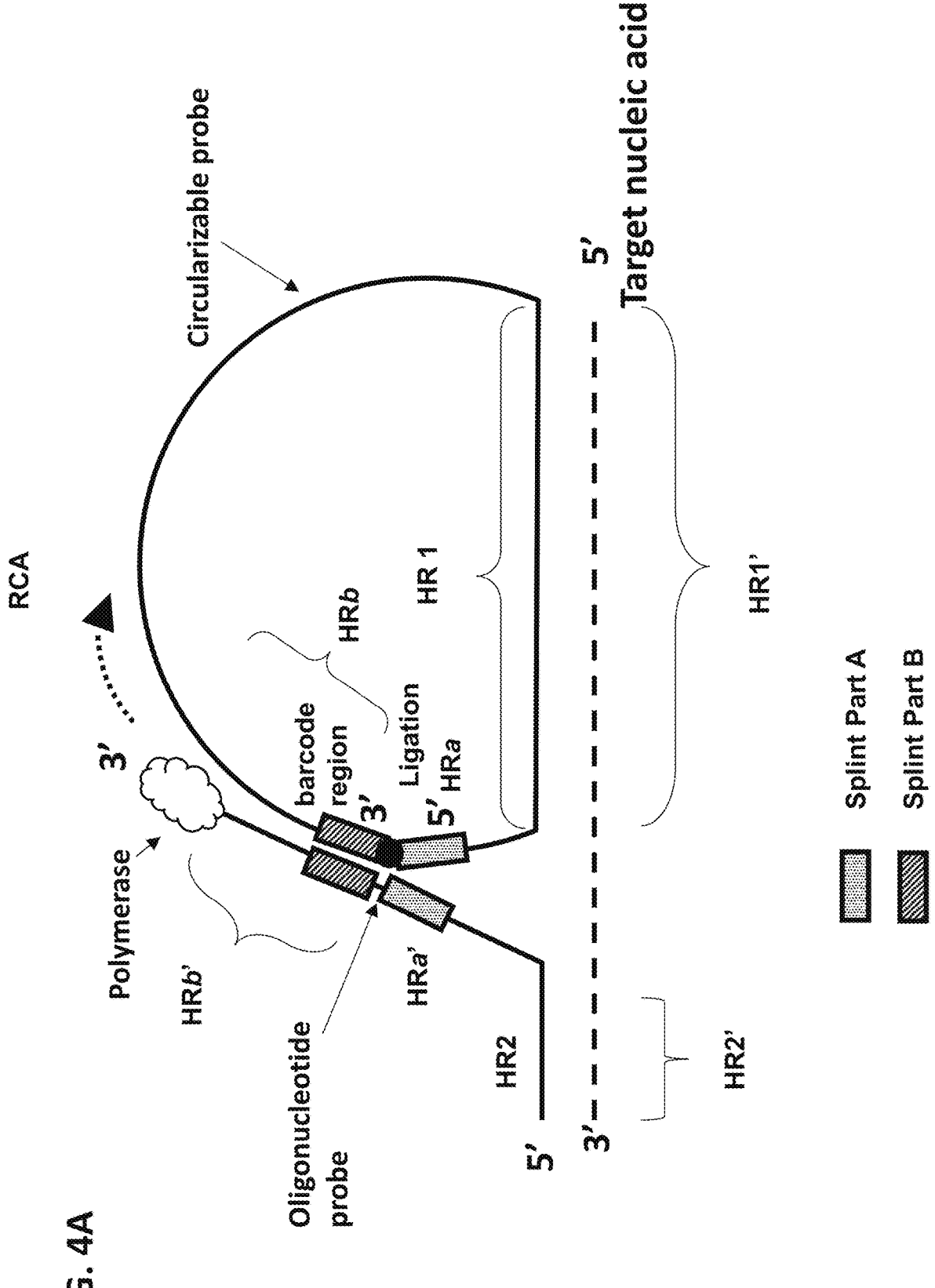
FIG. 4A and FIG. 4B depict exemplary design and method for analyzing a biological sample that employ an oligonucleotide probe as a splint to circularize and amplify a circularizable probe.
Figure 4B:
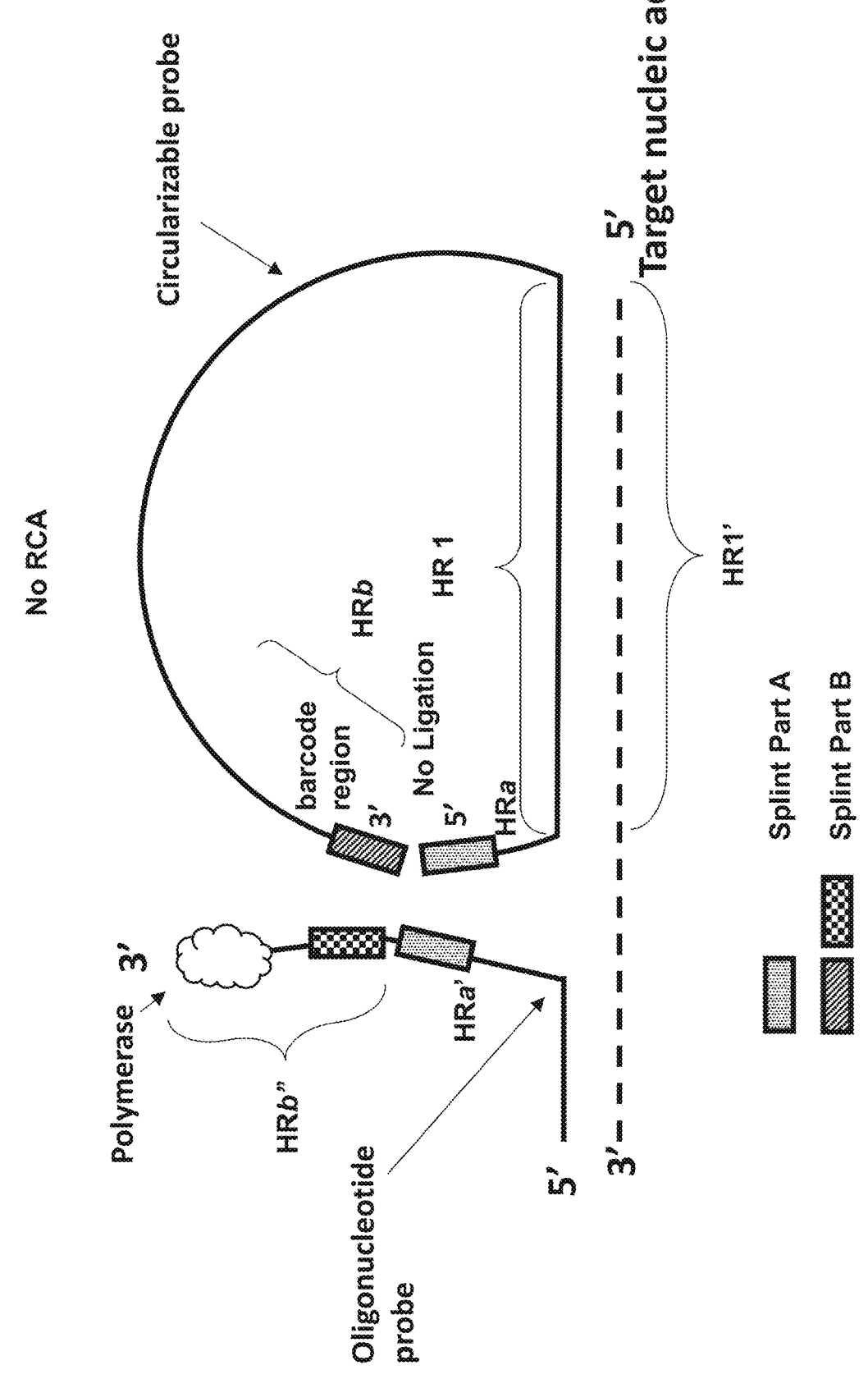

As depicted in FIG. 4A, the oligonucleotide probe comprises HRa' that is optionally a common sequence among oligonucleotide probes for different target nucleic acids, and a sequence (e.g., barcode) of HRb' can be complementary to the barcode region of HRb. The barcode region of HRb' may correspond to the target nucleic acid or a sequence thereof. The circularizable probe and oligonucleotide probe hybridize to the target nucleic acid, and HRa of the circularizable probe hybridizes to HRa' of the oligonucleotide probe, and the barcode region of HRb of the circularizable probe is complementary to a sequence of HRb' of the oligonucleotide probe. HRa and HRb are ligated using the oligonucleotide probe as a splint and the circularizable probe is circularized. RCA of the circularized probe can be primed by the oligonucleotide probe or a separate primer. In some aspects, as shown in FIG. 4B, a sequence (e.g., barcode) of HRb" is not complementary to the barcode region of HRb. In such instance, HRa and HRb are not ligated, the circularizable probe is not circularized, and no RCA occurs. In some cases, the oligonucleotide probe shown in FIG. 4B in nonspecifically bound to the target nucleic acid—in other words, the oligonucleotide probe may not comprise HR2 which is complementary to HR2' in the target nucleic acid. Such nonspecific hybridization may generate a false positive signal using conventional SNAIL, and a method disclosed herein can be used to eliminate the false positive signal since the oligonucleotide probe shown in FIG. 4B does not match the circularized probe. The circularizable probe cannot be ligated using the oligonucleotide probe as a splint. Splint Part A can be a common or universal region among pairs of oligonucleotide probes and circularizable probes targeting different analytes, such as different target nucleic acids. Splint Part B can be analyte-specific, for example, a genespecific barcode region comprising one or more barcodes. FIG. 4A and FIG. 4B show Splint Part A is 5' to Splint Part B, but the locations of Splint Part A and Splint Part B may be switched, e.g., in the oligonucleotide probe, Splint Part A can be 3' to Splint Part B.

In some instances, the oligonucleotide probe comprises hybridization region HR2, hybridization region HRa', and hybridization region HRb', and the circularizable probe comprises hybridization region HRa, hybridization region HR1, and hybridization region HRb comprising a barcode region corresponding to the target nucleic acid or a sequence thereof. In some instances, the circularizable probe comprises a barcode region at or near the one end of the circularizable probe and a common sequence present at or near the other end of the circularizable probe. In some examples, the common sequence is common among various circularizable probes. In some aspects, the common sequence can be useful for generically providing hybridization to bring a portion of the oligonucleotide probe in proximity to aid in the ligation of the ends of the circularizable probe. For example, the barcode region can be located at or near the 5' end of the circularizable probe (e.g., HRa) and the common sequence present at or near the 3' end of the circularizable probe (e.g., HRb). In some cases, the barcode region can be located at or near the 3' end of the circularizable probe (e.g., HRb) and the common sequence present at or near the 5' end of the circularizable probe (e.g., HRa). In some instances, the oligonucleotide probe can include a portion with a sequence that is complementary to a barcode region in the corresponding circularizable probe and a common sequence that is complementary to a common sequence present at or near the other end of the circularizable probe. The order of the sequence that is complementary to a barcode region in the corresponding circularizable probe and a common sequence that is complementary to a common sequence present at or near the other end of the circularizable probe in the oligonucleotide probe can be switched. For example, the oligonucleotide probe comprises HR2-sequence complementary to barcode region-common sequence in the 5' to 3' direction or HR2-common sequence-sequence complementary to barcode region in the 5' to 3' direction.

In some embodiments, the circularizable probe includes a barcode region corresponding to the target nucleic acid or a sequence thereof, and the oligonucleotide probe comprises a that is complementary to the barcode region of the circularizable probe. In some aspects, the circularizable additionally comprises a second barcode region. In some cases, the barcode region in HRb is a first barcode region and HRa comprises a second and separate barcode region. In some embodiments, the first and second barcode regions each independently comprises one or more barcodes. In some examples, the combination of the first and second barcode regions correspond to the target nucleic acid or sequence thereof. In some aspects, the circularizable probe comprises a single copy of the barcode region.

In some embodiments, the circularizable probe comprises a second barcode region that does not hybridize to the oligonucleotide probe. For example, the second barcode region is different from the barcode region of HRb. In some aspects, the second barcode region corresponds to the target nucleic acid or a sequence thereof. In some cases, detecting the RCA product comprises detecting the complement of the second barcode region in the RCA product. In some cases, the second barcode region is a different length from the barcode sequence in the barcode region of HRb.

(a) Hybridization and Ligation

In some instances, the hybridization of the circularizable probes and oligonucleotide probes to a target nucleic acid analyte and may lead to the generation of a rolling circle amplification (RCA) template. In some instances, the assay uses or generates a circular nucleic acid molecule which can be the RCA template. In some instances, the ligation product is formed from circularization of a circularizable probe using an oligonucleotide probe upon hybridization of both to a target sequence. In some instances, the ligation involves chemical ligation. In some instances, the ligation involves template dependent ligation. In some instances, the ligation involves template independent ligation. In some instances, the ligation involves enzymatic ligation.

In some instances, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some instances, the ligase is a T4 RNA ligase. In some instances, the ligase is a splintR ligase. In some instances, the ligase is a single stranded DNA ligase. In some instances, the ligase is a T4 DNA ligase. In some instances, the ligase is a ligase that has an DNA-splinted DNA ligase activity. In some instances, the ligase is a ligase that has an RNA-splinted DNA ligase activity.

In some instances, the ligation herein is a direct ligation. In some instances, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, e.g., separated by one or more intervening nucleotides or "gaps". In some instances, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo) nucleotide(s) which are complementary to a splint, circularizable probe, or target nucleic acid. The gap may be a gap of 1 to 60 nucleotides or a gap of 1 to 40 nucleotides or a gap of 3 to 40 nucleotides. In specific implementations, the gap may be a gap of about 1, 2, 3, 4, 5, 6, 7, 8, 9 or 10 or more nucleotides, of any integer (or range of integers) of nucleotides in between the indicated values. In some instances, the gap between said terminal regions may be filled by a gap oligonucleotide or by extending the 3' end of a polynucleotide. In some cases, ligation involves ligating the ends of the probe to at least one gap (oligo) nucleotide, such that the gap (oligo) nucleotide becomes incorporated into the resulting polynucleotide. In some instances, the ligation herein is preceded by gap filling. In other implementations, the ligation herein does not require gap filling.

In some instances, ligation of the polynucleotides produces polynucleotides with melting temperature higher than that of un-ligated polynucleotides. Thus, in some aspects, ligation stabilizes the hybridization complex containing the ligated polynucleotides prior to subsequent steps, comprising amplification and detection.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature (Tm) of the DNA strands. This selectively reduces the concentration of annealed mismatched substrates (expected to have a slightly lower Tm around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

In some instances, the ligation herein is a proximity ligation of ligating two (or more) nucleic acid sequences that are in proximity with each other, e.g., through enzymatic means (e.g., a ligase). In some instances, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference). A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

(b) Primer Extension and Amplification

In some instances, upon the hybridization of the circularizable probes and oligonucleotide probes to a target nucleic acid analyte and ligation to generate the circular probe, an extension or amplification product can be generated.

In some embodiments, the oligonucleotide probes described herein can be used as a primer for extension or amplification. A primer is generally a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence. A primer extension reaction generally refers to any method where two nucleic acid sequences become linked (e.g., hybridized) by an overlap of their respective terminal complementary nucleic acid sequences (e.g., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

In some instances, the disclosed methods may comprise the use of a rolling circle amplification (RCA) technique to amplify signal. Rolling circle amplification is an isothermal, DNA polymerase-mediated process in which long single-stranded DNA molecules are synthesized on a short circular single-stranded DNA template using a single DNA primer (Zhao, et al. (2008), "Rolling Circle Amplification: Applications in Nanotechnology and Biodetection with Functional Nucleic Acids", *Angew Chem Int Ed Engl.* 47 (34): 6330-6337; Ali, et al. (2014), "Rolling Circle Amplification: A Versatile Tool for Chemical Biology, Materials Science and Medicine", *Chem Soc Rev.* 43 (10): 3324-3341). The RCA product is a concatemer containing tens to hundreds of tandem repeats that are complementary to the circular template, and may be used to develop sensitive techniques for the detection of a variety of targets, including nucleic acids (DNA, RNA), small molecules, proteins, and cells (Ali, et al. (2014), ibid.). In some implementations, a primer that hybridizes to the circular probe or circularized probe is added and used as such for amplification. In some instances, the RCA comprises a linear RCA, a branched RCA, a dendritic RCA, or any combination thereof.

In some instances, the amplification is performed at a temperature between or between about 20° C. and about 60° C. In some instances, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some instances, upon addition of a DNA polymerase in the presence of appropriate dNTP precursors and other cofactors, a primer is elongated to produce multiple copies of the circular template. This amplification step can utilize isothermal amplification or non-isothermal amplification. In some instances, after the formation of the hybridization complex and association of the amplification probe, the hybridization complex is rolling-circle amplified to generate a cDNA nanoball (e.g., amplicon) containing multiple copies of the cDNA. Techniques for rolling circle amplification (RCA) are established in the field, such as linear RCA, a branched RCA, a dendritic RCA, or any combination thereof. (See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49 (11): 2540-2550; Schweitzer et al. Proc. Natl Acad. Sci. USA 97:101 13-1 19, 2000; Faruqi et al, BMC Genomics 2:4, 2000; Nallur et al, Nucl. Acids Res. 29: el 18, 2001; Dean et al. Genome Res. 1 1:1095-1099, 2001; Schweitzer et al, Nature Biotech. 20:359-365, 2002; U.S. Pat. Nos. 6,054, 274, 6,291,187, 6,323,009, 6,344,329 and 6,368,801). Exemplary polymerases for use in RCA comprise DNA polymerase such phi29 (q29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some instances, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some instances, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some instances, the RCA template may comprise the target analyte, or a part thereof, where the target analyte is a nucleic acid, or it may be provided or generated as a proxy, or a marker, for the analyte. In some instances, the RCA template may comprise a sequence of the probes and probe sets hybridized to an endogenous analyte and/or a labelling agent. In some instances, the amplification product can be generated as a proxy, or a marker, for the analyte. As noted above, many assays can be used for the detection of numerous different analytes, which use a RCA-based detection system, e.g., where the signal is provided by generating a RCP from a circular RCA template which is provided or generated in the assay, and the RCP is detected to detect the analyte. The RCP may thus be regarded as a reporter which is detected to detect the target analyte. However, the RCA template may also be regarded as a reporter for the target analyte; the RCP is generated based on the RCA template, and comprises complementary copies of the RCA template. The RCA template determines the signal which is detected, and is thus indicative of the target analyte. As will be described in more detail below, the RCA template may be a probe, or a part or component of a probe, or may be generated from a probe, or it may be a component of a detection assay (e.g., a reagent in a detection assay), which is used as a reporter for the assay, or a part of a reporter, or signal-generation system. The RCA template used to generate the RCP may thus be a circular (e.g. circularized) reporter nucleic acid molecule, namely from any RCA-based detection assay which uses or generates a circular nucleic acid molecule as a reporter for the assay. Since the RCA template generates the RCP reporter, it may be viewed as part of the reporter system for the assay.

In some instances, an assay may detect a product herein that includes a molecule or a complex generated in a series of reactions, e.g., hybridization, ligation, extension, replication, transcription/reverse transcription, and/or amplification (e.g., rolling circle amplification), in any suitable combination.

IV. Detection and Analysis

In some aspects, after formation of a hybridization complex comprising nucleic acid probes and/or probe sets described in Section III and further processing (e.g., ligation, rolling circle amplification, or any combination thereof), the method further includes detection of the probe or probe set hybridized to the target nucleic acid or any products generated therefrom or a derivative thereof. In any of the embodiments herein, the method can further comprise imaging the biological sample to detect a ligation product or a circularized probe or product thereof. In any of the embodiments herein, a sequence of the ligation product, rolling circle amplification product, or other generated product can be analyzed in situ in the biological sample. In any of the embodiments herein, the imaging can comprise detecting a signal associated with a fluorescently labeled probe that directly or indirectly binds to a rolling circle amplification product of the circularized probe. In any of the embodiments herein, the sequence of the sequence of the ligation product, rolling circle amplification product, or other generated product can be analyzed by sequential hybridization, sequencing by hybridization, sequencing by ligation, sequencing by synthesis, sequencing by binding, or a combination thereof.

Methods for binding and identifying a target nucleic acid that uses various probes or oligonucleotides have been described in, e.g., US2003/0013091, US2007/0166708, US2010/0015607, US2010/0261026, US2010/0262374, US2010/0112710, US2010/0047924, and US2014/0371088, each of which is incorporated herein by reference in its entirety. Detectably-labeled probes can be useful for detecting multiple target nucleic acids and be detected in one or more hybridization cycles (e.g., sequential hybridization assays, or sequencing by hybridization).

In some embodiments, the detecting can comprise binding an intermediate probe directly or indirectly to the primary probe or probe set, binding a detectably labeled probe directly or indirectly to a detection region of the intermediate probe, and detecting a signal associated with the detectably labeled probe. In some embodiments, the method comprises detecting a rolling circle amplification product (RCP) generated using a circular or circularized primary probe or probe set as a template. In some embodiments, the method comprises detecting a rolling circle amplification product (RCP) generated using a circular or circularized probe or probe that binds to a primary probe or probe set as a template. In some embodiments, detecting the RCP comprises binding an intermediate probe directly or indirectly to the RCP, binding a detectably labeled probe directly or indirectly to a detection region of the intermediate probe, and detecting a signal associated with the detectably labeled probe. In some embodiments, the method can comprise performing one or more wash steps to remove unbound and/or nonspecifically bound intermediate probe molecules from the primary probes or the products of the primary probes.

In some embodiments, the detecting can comprise: detecting signals associated with detectably labeled probes that are hybridized to barcode regions or complements thereof in the RCA product, and/or detecting signals associated with detectably labeled probes that are hybridized to intermediate probes which are in turn hybridized to the barcode regions or complements thereof. In some embodiments, the detectably labeled probes can be fluorescently labeled.

In any of the embodiments herein, a sequence associated with the target nucleic acid or the probe(s) can comprise one or more barcode sequences or complements thereof. In any of the embodiments herein, the sequence of the rolling circle amplification product can comprise one or more barcode sequences or complements thereof. In any of the embodiments herein, a ligated circular probe can comprise one or more barcode sequences or complements thereof. In any of the embodiments herein, the one or more barcode sequences can comprise a barcode sequence corresponding to the target nucleic acid. In any of the embodiments herein, the one or more barcode sequences can comprise a barcode sequence corresponding to the sequence of interest, such as variant(s) of a single nucleotide of interest.

In any of the embodiments herein, the detecting step can comprise contacting the biological sample with one or more detectably-labeled probes that directly or indirectly hybridize to the rolling circle amplification product, and dehybridizing the one or more detectably-labeled probes from the rolling circle amplification product. In any of the embodiments herein, the contacting and dehybridizing steps can be repeated with the one or more detectably-labeled probes and/or one or more other detectably-labeled probes that directly or indirectly hybridize to the rolling circle amplification product.

In any of the embodiments herein, the detecting step can comprise contacting the biological sample with one or more intermediate probes that directly or indirectly hybridize to the rolling circle amplification product, wherein the one or more intermediate probes are detectable using one or more detectably-labeled probes. In any of the embodiments herein, the detecting step can further comprise dehybridizing the one or more intermediate probes and/or the one or more detectably-labeled probes from the rolling circle amplification product. In any of the embodiments herein, the contacting and dehybridizing steps can be repeated with the one or more intermediate probes, the one or more detectably-labeled probes, one or more other intermediate probes, and/or one or more other detectably-labeled probes.

In any of the embodiments herein, detecting the barcode sequences or complements thereof can further comprise: contacting the test biological sample with the universal pool of detectably labeled probes and a second pool of intermediate probes, wherein the intermediate probes of the second pool of intermediate probes comprise hybridization regions complementary to the barcode sequences or complements thereof and reporter regions complementary to a detectably labeled probe of the universal pool of detectably labeled probes; and detecting complexes formed between the barcode sequences or complements thereof, the intermediate probes of the second pool of intermediate probes, and the detectably labeled probes.

In any of the embodiments herein, each barcode sequence or complement thereof can be assigned a sequence of signal codes that identifies the barcode sequence or complement thereof, and detecting the barcode sequences or complements thereof can comprise decoding the barcode sequences or complements thereof by detecting the corresponding sequences of signal codes detected from sequential hybridization, detection, and removal of sequential pools of intermediate probes and the universal pool of detectably labeled probes.

In some instances, the present disclosure relates to methods and compositions for encoding and detecting analytes in a temporally sequential manner for in situ analysis of an analyte in a biological sample, e.g., a target nucleic acid in a cell in an intact tissue. In some aspects, provided herein is a method for detecting the detectably-labeled probes, thereby generating a signal signature. In some instances, the signal signature corresponds to an analyte of the plurality of analytes. In some instances, the methods described herein are based, in part, on the development of a multiplexed biological assay and readout, in which a sample is first contacted with a plurality of nucleic acid probes comprising one or more probe types (e.g., labelling agent, circularizable probe, circular probe, etc.), allowing the probes to directly or indirectly bind target analytes, which may then be optically detected (e.g., by detectably-labeled probes) in a temporally-sequential manner. In some instances, the probes or probe sets comprising various probe types may be applied to a sample simultaneously. In some instances, the probes or probe sets comprising various probe types may be applied to a sample sequentially. In some aspects, the method comprises sequential hybridization of detectably-labeled probes to create a spatiotemporal signal signature or code that identifies the analyte.

In some instances, after hybridization of a detectably-labeled probes (e.g., fluorescently labeled oligonucleotide) that detects a sequence (e.g., barcode sequence on a secondary probe or a primary probe (e.g., circularizable probe)), and optionally washing away the unbound molecules of the detectably-labeled probe, the sample is imaged and the detection oligonucleotide or detectable label is inactivated and/or removed. In some instances, removal of the signal associated with the hybridization between rounds can be performed by washing, heating, stripping, enzymatic digestion, photo-bleaching, displacement (e.g., displacement of detectably-labeled probes with another reagent or nucleic acid sequence), cleavage, quenching, chemical degradation, bleaching, oxidation, or any combinations thereof.

In some examples, removal of a probe (e.g., unhybridizing the entire probe), signal modifications (e.g., quenching, masking, photo-bleaching, signal enhancement (e.g., via FRET), signal amplification, etc.), signal removal (e.g., cleaving off or permanently inactivating a detectable label) can be performed. Inactivation may be caused by removal of the detectable label (e.g., from the sample, or from the probe, etc.), and/or by chemically altering the detectable label in some fashion, e.g., by photobleaching the detectable label, bleaching or chemically altering the structure of the detectable label, e.g., by reduction, etc.). In some instances, the fluorescently labeled oligonucleotide and/or the intermediate probe hybridized to the fluorescently labeled oligonucleotide (e.g., bridge probe) can be removed. In some instances, a fluorescent detectable label may be inactivated by chemical or optical techniques such as oxidation, photobleaching, chemically bleaching, stringent washing or enzymatic digestion or reaction by exposure to an enzyme, dissociating the detectable label from other components (e.g., a probe), chemical reaction of the detectable label (e.g., to a reactant able to alter the structure of the detectable label) or the like. For instance, bleaching may occur by exposure to oxygen, reducing agents, or the detectable label could be chemically cleaved from the nucleic acid probe and washed away via fluid flow.

In some instances, removal of a signal comprises displacement of probes with another reagent (e.g., probe) or nucleic acid sequence. For example, a given probe (e.g., detectably-labeled probes and/or the intermediate probe hybridized to the fluorescently labeled oligonucleotide (e.g., bridge probe)) may be displaced by a subsequent probe that hybridizes to an overlapping region shared between the binding sites of the probes. In some cases, a displacement reaction can be very efficient, and thus allows for probes to be switched quickly between cycles, without the need for chemical stripping (or any of the damage to the sample that is associated therewith). In some instances, a sequence for hybridizing the subsequent or displacer probe (e.g. a toehold sequence) may be common across a plurality of probes capable of hybridizing to a given binding site. In some aspects, a single displacement probe can be used to simultaneously displace detection probes bound to an equivalent barcode position from all of the RCPs within a given sample simultaneously (with the displacement mediated by the subsequent detection probes). This may further increase efficiency and reduce the cost of the method, as fewer different probes are required.

After a signal is inactivated and/or removed, then the sample is re-hybridized in a subsequent round with a subsequent fluorescently labeled oligonucleotide, and the oligonucleotide can be labeled with the same color or a different color as the fluorescently labeled oligonucleotide of the previous cycle. In some instances, as the positions of the analytes, probes, and/or products thereof can be fixed (e.g., via fixing and/or crosslinking) in a sample, the fluorescent spot corresponding to an analyte, probe, or product thereof remains in place during multiple rounds of hybridization and can be aligned to read out a string of signals associated with each target analyte.

In some embodiments, the detection may be spatial, e.g., in two or three dimensions. In some embodiments, the detection may be quantitative, e.g., the amount or concentration of a primary nucleic acid probe (and of a target nucleic acid) may be determined. In some embodiments, the primary probes, secondary probes, higher order probes, and/or detectably labeled probes may comprise any of a variety of entities able to hybridize a nucleic acid, e.g., DNA, RNA, LNA, and/or PNA, etc., depending on the application.

In some embodiments, disclosed herein is a multiplexed assay where multiple targets (e.g., nucleic acids such as genes or RNA transcripts, or protein targets) are probed with multiple primary probes (e.g., circularizable probes), and optionally multiple secondary probes hybridizing to the primary barcodes (or complementary sequences thereof) are all hybridized at once, followed by sequential secondary barcode detection and decoding of the signals. In some embodiments, detection of barcodes or subsequences of the barcode can occur in a cyclic manner.

In some embodiments, a method for analyzing a region of interest in a target nucleic acid is a multiplexed assay where multiple probes (e.g., circularizable probes) are used to detect multiple regions of interest simultaneously (e.g., variations at the same location of a target nucleic acid and/or SNPs in various locations). In some embodiments, one or more detections of one or more regions of interest may occur simultaneously. In some embodiments, one or more detections of one or more regions of interest may occur sequentially. In some embodiments, multiple circularizable probes of the same design are used to detect one or more regions of interest, using different barcodes associated with each region of interest. In some embodiments, multiple circularizable probes of different design are used to detect one or more regions of interest, using different barcodes (e.g., each barcode associated with a target nucleic acid or sequence thereof). In some embodiments, the one or more regions of interest are localized on the same molecule (e.g., RNA or DNA). In alternative embodiments, the one or more single nucleotides of interest are localized on different molecules.

In some aspects, the provided methods involve analyzing, e.g., detecting or determining, one or more sequences present in the polynucleotides (e.g., circularizable probes) and/or in a product or derivative thereof, such as in an amplified circularizable probe. In some embodiments, the analysis comprises determining the sequence of all or a portion of the amplification product. In some embodiments, the analysis comprises detecting a sequence present in the amplification product. In some embodiments, the sequence of all or a portion of the amplification product is indicative of the identity of a region of interest in a target nucleic acid. In other embodiments, the provided methods involve analyzing, e.g., detecting or determining, one or more sequences present in the polynucleotide probes (e.g., a barcode sequence present in a circularizable probe or product thereof).

In some embodiments, a method disclosed herein may also comprise one or more signal amplification components. In some embodiments, the present disclosure relates to the detection of nucleic acids sequences in situ using probe hybridization and generation of amplified signals associated with the probes, wherein background signal is reduced and sensitivity is increased. In some embodiments, the RCA product generated using a method disclosed herein can be detected in with a method that comprises signal amplification.

In some embodiments, the detection or determination comprises hybridizing to the amplification product a detection oligonucleotide labeled with a fluorophore, an isotope, a mass tag, or a combination thereof. In some embodiments, the detection or determination comprises imaging the amplification product. In some embodiments, the target nucleic acid is an mRNA in a tissue sample, and the detection or determination is performed when the target nucleic acid and/or the amplification product is in situ in the tissue sample.

In some aspects, the provided methods comprise imaging the amplification product (e.g., amplicon) and/or one or more portions of the polynucleotides, for example, via binding of the detection probe and detecting the detectable label. In some embodiments, the detection probe comprises a detectable label that can be measured and quantitated. The terms "label" and "detectable label" comprise a directly or indirectly detectable moiety that is associated with (e.g., conjugated to) a molecule to be detected, e.g., a detectable probe, comprising, but not limited to, fluorophores, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like.

The term "fluorophore" comprises a substance or a portion thereof that is capable of exhibiting fluorescence in the detectable range. Particular examples of labels that may be used in accordance with the provided embodiments comprise, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, Renilla luciferase, NADPH, beta-galactosidase, horseradish peroxidase, glucose oxidase, alkaline phosphatase, chloramphenical acetyl transferase, and urease.

Fluorescence detection in tissue samples can often be hindered by the presence of strong background fluorescence. "Autofluorescence" is the general term used to distinguish background fluorescence (that can arise from a variety of sources, including aldehyde fixation, extracellular matrix components, red blood cells, lipofuscin, and the like) from the desired immunofluorescence from the fluorescently labeled antibodies or probes. Tissue autofluorescence can lead to difficulties in distinguishing the signals due to fluorescent antibodies or probes from the general background. In some embodiments, a method disclosed herein utilizes one or more agents to reduce tissue autofluorescence, for example, Autofluorescence Eliminator (Sigma/EMD Millipore), TrueBlack Lipofuscin Autofluorescence Quencher (Biotium), MaxBlock Autofluorescence Reducing Reagent Kit (Max Vision Biosciences), and/or a very intense black dye (e.g., Sudan Black, or comparable dark chromophore).

In some embodiments, a detectable probe containing a detectable label can be used to detect one or more polynucleotide(s) and/or amplification products (e.g., amplicon) described herein. In some embodiments, the methods involve incubating the detectable probe containing the detectable label with the sample, washing unbound detectable probe, and detecting the label, e.g., by imaging.

Examples of detectable labels comprise but are not limited to various radioactive moieties, enzymes, prosthetic groups, fluorescent markers, luminescent markers, bioluminescent markers, metal particles, protein-protein binding pairs and protein-antibody binding pairs. Examples of fluorescent proteins comprise, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride and phycoerythrin.

Examples of bioluminescent markers comprise, but are not limited to, luciferase (e.g., bacterial, firefly and click beetle), luciferin, aequorin and the like. Examples of enzyme systems having visually detectable signals comprise, but are not limited to, galactosidases, glucorimidases, phosphatases, peroxidases and cholinesterases. Identifiable markers also comprise radioactive compounds such as $^{125}I$, $^{35}S$, $^{14}C$, or $^{3}H$. Identifiable markers are commercially available from a variety of sources.

Examples of fluorescent labels and nucleotides and/or polynucleotides conjugated to such fluorescent labels comprise those described in, for example, Hoagland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). In some embodiments, exemplary techniques and methods methodologies applicable to the provided embodiments comprise those described in, for example, U.S. Pat. Nos. 4,757,141, 5,151,507 and 5,091,519. In some embodiments, one or more fluorescent dyes are used as labels for labeled target sequences, for example, as described in U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthine dyes); and U.S. Pat. No. 5,688,648 (energy transfer dyes). Labelling can also be carried out with quantum dots, as described in U.S. Pat. Nos. 6,322,901, 6,576,291, 6,423,551, 6,251,303, 6,319,426, 6,426,513, 6,444,143, 5,990,479, 6,207,392, US 2002/0045045 and US 2003/0017264. As used herein, the term "fluorescent label" comprises a signaling moiety that conveys information through the fluorescent absorption and/or emission properties of one or more molecules. Exemplary fluorescent properties comprise fluorescence intensity, fluorescence lifetime, emission spectrum characteristics and energy transfer.

Examples of commercially available fluorescent nucleotide analogues readily incorporated into nucleotide and/or polynucleotide sequences comprise, but are not limited to, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHOD AMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHOD AMINE GREEN™-5-UTP, ALEXA FLUOR™ 488-5-UTP, and ALEXA FLUOR™ 546-14-UTP (Molecular Probes, Inc. Eugene, Oreg.). Methods are known for custom synthesis of nucleotides having other fluorophores (See, Henegariu et al. (2000) Nature Biotechnol. 18:345).

Other fluorophores available for post-synthetic attachment comprise, but are not limited to, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red (available from Molecular Probes, Inc., Eugene, Oreg.), Cy2, Cy3.5, Cy5.5, and Cy7 (Amersham Biosciences, Piscataway, N.J.). FRET tandem fluorophores may also be used, comprising, but not limited to, PerCP-Cy5.5, PE-Cy5, PE-Cy5.5, PE-Cy7, PE-Texas Red, APC-Cy7, PE-Alexa dyes (610, 647, 680), and APC-Alexa dyes.

In some cases, metallic silver or gold particles may be used to enhance signal from fluorescently labeled nucleotide and/or polynucleotide sequences (Lakowicz et al. (2003) Bio Techniques 34:62).

Biotin, or a derivative thereof, may also be used as a label on a nucleotide and/or a polynucleotide sequence, and subsequently bound by a detectably labeled avidin/streptavidin derivative (e.g., phycoerythrin-conjugated streptavidin), or a detectably labeled anti-biotin antibody. Digoxigenin may be incorporated as a label and subsequently bound by a detectably labeled anti-digoxigenin antibody (e.g., fluoresceinated anti-digoxigenin). An aminoallyl-dUTP residue may be incorporated into a polynucleotide sequence and subsequently coupled to an N-hydroxy succinimide (NHS) derivatized fluorescent dye. In general, any member of a conjugate pair may be incorporated into a detection polynucleotide provided that a detectably labeled conjugate partner can be bound to permit detection. As used herein, the term antibody refers to an antibody molecule of any class, or any sub-fragment thereof, such as a Fab.

Other suitable labels for a polynucleotide sequence may comprise fluorescein (FAM), digoxigenin, dinitrophenol (DNP), dansyl, biotin, bromodeoxyuridine (BrdU), hexahistidine (6×His), and phosphor-amino acids (e.g., P-tyr, P-ser, P-thr). In some embodiments the following hapten/antibody pairs are used for detection, in which each of the antibodies is derivatized with a detectable label: biotin/a-biotin, digoxigenin/a-digoxigenin, dinitrophenol (DNP)/a-DNP, 5-Carboxyfluorescein (FAM)/a-FAM.

In some embodiments, a nucleotide and/or an polynucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, and PCT publication WO 91/17160. Many different hapten-capture agent pairs are available for use. Exemplary haptens comprise, but are not limited to, biotin, des-biotin and other derivatives, dinitrophenol, dansyl, fluorescein, Cy5, and digoxigenin. For biotin, a capture agent may be avidin, streptavidin, or antibodies. Antibodies may be used as capture agents for the other haptens (many dye-antibody pairs being commercially available, e.g., Molecular Probes, Eugene, Oreg.).

In some aspects, the detecting involves using detection methods such as flow cytometry; sequencing; probe binding and electrochemical detection; pH alteration; catalysis induced by enzymes bound to DNA tags; quantum entanglement; Raman spectroscopy; terahertz wave technology; and/or scanning electron microscopy. In some aspects, the flow cytometry is mass cytometry or fluorescence-activated flow cytometry. In some aspects, the detecting comprises performing microscopy, scanning mass spectrometry or other imaging techniques described herein. In such aspects, the detecting comprises determining a signal, e.g., a fluorescent signal.

In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detection probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detection probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity-so long exposures are often required. As only one point in the sample is illuminated at a time, 2D or 3D imaging requires scanning over a regular raster (e.g., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

In some embodiments, sequencing can be performed in situ. In situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (e.g., nucleotide sequence) of the incorporated nucleotides or labeled primer extension products can be determined, and consequently, the nucleotide sequence of the corresponding template nucleic acid. Aspects of in situ sequencing are described, for example, in Mitra et al., (2003) *Anal. Biochem.* 320, 55-65, and Lee et al., (2014) *Science,* 343 (6177), 1360-1363. In addition, examples of methods and systems for performing in situ sequencing are described in US 2016/0024555, US 2019/0194709, and in U.S. Pat. Nos. 10,138,509, 10,494,662 and 10,179,932. Exemplary techniques for in situ sequencing comprise, but are not limited to, STARmap (described for example in Wang et al., (2018) *Science,* 361 (6499) 5691), MERFISH (described for example in Moffitt, (2016) *Methods in Enzymology,* 572, 1-49), hybridization-based in situ sequencing (HybISS) (described for example in Gyllborg et al., Nucleic Acids Res (2020) 48 (19): e112, and FISSEQ (described for example in US 2019/0032121). In some cases, sequencing can be performed after the analytes are released from the biological sample.

In some embodiments, sequencing can be performed by sequencing-by-synthesis (SBS). In some embodiments, a sequencing primer is complementary to sequences at or near the one or more barcode(s). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, US 2011/005986, US 2005/0100900, U.S. Pat. No. 9,217,178, US 2009/0118128, US 2012/0270305, US 2013/0260372, and US 2013/0079232.

In some embodiments, sequencing can be performed by sequential fluorescence hybridization (e.g., sequencing by hybridization). Sequential fluorescence hybridization can involve sequential hybridization of detection probes comprising an oligonucleotide and a detectable label.

In some embodiments, sequencing can be performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. *Science* (2005), 309:1728-1732, and in U.S. Pat. Nos. 5,599,675; 5,750,341; 6,969,488; 6,172,218; and 6,306,597.

In some embodiments, the barcodes of the probes (e.g., the circularizable probe) or complements or products thereof are targeted by detectably labeled detection oligonucleotides, such as fluorescently labeled oligonucleotides. In some embodiments, one or more decoding schemes are used to decode the signals, such as fluorescence, for sequence determination.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004).

In some embodiments, real-time monitoring of DNA polymerase activity can be used during sequencing. For example, nucleotide incorporations can be detected through fluorescence resonance energy transfer (FRET), as described for example in Levene et al., *Science* (2003), 299, 682-686, Lundquist et al., *Opt. Lett.* (2008), 33, 1026-1028, and Korlach et al., *Proc. Natl. Acad. Sci. USA* (2008), 105, 1176-1181.

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

In some embodiments, the analysis and/or sequence determination involves washing to remove unbound polynucleotides, thereafter revealing a fluorescent product for imaging.

V. Compositions and Kits

Also provided herein are kits, for example comprising one or more oligonucleotides disclosed herein (e.g., circularizable probes and oligonucleotide probes), and reagents for performing the methods provided herein, for example reagents required for one or more steps comprising hybridization, ligation, amplification, detection, sequencing, and/or sample preparation as described herein. In some embodiments, the kit further comprises a target nucleic acid. In some embodiments, any or all of the polynucleotides are DNA molecules. In some embodiments, the target nucleic acid is a messenger RNA molecule.

The various components of the kit may be present in separate containers or certain compatible components may be pre-combined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection and/or sequencing, such as barcode detection probes or detectable labels. In some embodiments, the kits optionally contain other components, for example nucleic acid primers, enzymes and reagents, buffers, nucleotides, modified nucleotides, reagents for additional assays.

In some aspects, the provided embodiments can be applied in an in situ method of analyzing nucleic acid sequences, such as an in situ transcriptomic analysis or in situ sequencing, for example from intact tissues or samples in which the spatial information has been preserved. In some aspects, the embodiments can be applied in an imaging or detection method for multiplexed nucleic acid analysis. In some aspects, the provided embodiments can be used to identify or detect regions of interest in target nucleic acids.

In some aspects, the embodiments can be applied in investigative and/or diagnostic applications, for example, for characterization or assessment of particular cell or a tissue from a subject. Applications of the provided method can comprise biomedical research and clinical diagnostics. For example, in biomedical research, applications comprise, but are not limited to, spatially resolved gene expression analysis for biological investigation or drug screening. In clinical diagnostics, applications comprise, but are not limited to, detecting gene markers such as disease, immune responses, bacterial or viral DNA/RNA for patient samples.

VI. Terminology

Specific terminology is used throughout this disclosure to explain various aspects of the apparatus, systems, methods, and compositions that are described.

Having described some illustrative embodiments of the present disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the present disclosure. In particular, although many of the examples presented herein involve specific combinations of method acts or system elements, it should be understood that those acts and those elements may be combined in other ways to accomplish the same objectives.

As used herein, the singular forms "a," "an," and "the" include plural referents unless the context clearly dictates otherwise. For example, "a" or "an" means "at least one" or "one or more."

The term "about" as used herein refers to the usual error range for the respective value readily known to the skilled person in this technical field. Reference to "about" a value or parameter herein includes (and describes) embodiments that are directed to that value or parameter per se.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

(i) Barcode

A "barcode" is a label, or identifier, that conveys or is capable of conveying information (e.g., information about an analyte in a sample, a bead, and/or a probe). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those established in the field. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties that are established in the field. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are established in the field.

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (e.g., can be oligoribonucleotides) and/or deoxyribonucleotide monomers (e.g., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(vi) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence.

(vii) Primer Extension

A "primer extension" refers to any method where two nucleic acid sequences become linked (e.g., hybridized) by an overlap of their respective terminal complementary nucleic acid sequences (for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(viii) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence can be used as a template for single-strand synthesis of a corresponding cDNA molecule.

(ix) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus*.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g. DNA polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments, the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oN™ DNA ligase, available from New England Biolabs, Ipswich, MA), and Ampligase™ (available from Epicentre Biotechnologies, Madison, WI). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™, ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™, ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (also known as quantitative PCR or qPCR), using techniques established in the field, such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(xi) Label, Detectable Label, and Optical Label

The terms "detectable label," "optical label," and "label" are used interchangeably herein to refer to a directly or indirectly detectable moiety that is associated with (e.g., conjugated to) a molecule to be detected, e.g., a probe for in situ assay, a probe or analyte. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature or to a probe associated with a feature. For example, detectably labeled features can include a fluorescent, a colorimetric, or a chemiluminescent label attached to a bead (see, for example, Rajeswari et al., J. Microbiol Methods 139:22-28, 2017, and Forcucci et al., J. Biomed Opt. 10:105010, 2015, the entire contents of each of which are incorporated herein by reference).

In some embodiments, a plurality of detectable labels can be attached to a feature, probe, or composition to be detected. For example, detectable labels can be incorporated during nucleic acid polymerization or amplification (e.g., Cy5®-labeled nucleotides, such as Cy5®-dCTP). Any suitable detectable label can be used. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DIA (4-Di-16-ASP), DiD (DilC18 (5)), DIDS, Dil (DilC18 (3)), DiO (DiOC18 (3)), DiR (DilC18 (7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, Lys-oSensor™ Blue (pH 5), LysoSensor™ Green (pH 5), Lys-oSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phy-coerythrin), PE-Cy5, PE-Cy7, PE-Texas Red, PerCP (Peri-dinin chlorphyll protein), PerCP-Cy5.5 (TruRed), PharRed (APC-Cy7), C-phycocyanin, R-phycocyanin, R-phyco-erythrin (PE), PI (Propidium Iodide), PKH26, PKH67, POPO™-1/PO-PRO™-1, POPO™-3/PO-PRO™-3, Pro-pidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rho-damine 110, Rhodamine 123, 5-ROX (carboxy-X-rhod-amine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, Spec-trumGreen® #1, SpectrumGreen® #2, SpectrumOrange®, SpectrumRed®, SYTOR 11, SYTOR 13, SYTOR 17, SYTOR 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiaz-ole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66W, YFP (Yellow Fluorescent Protein), YOYOR-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yel-low, MAX, TET, TEX615, ATTO 488, ATTO 532, ATTO 550, ATTO 565, ATTO Rho101, ATTO 590, ATTO 633, ATTO 647$^N$, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcy-cler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horse-radish peroxidase (HRP), soybean peroxidase (SP), alkaline phosphatase, and luciferase. These protein moieties can catalyze chemiluminescent reactions given the appropriate substrates (e.g., an oxidizing reagent plus a chemilumines-cent compound. A number of compound families are known to provide chemiluminescence under a variety of conditions. Non-limiting examples of chemiluminescent compound families include 2,3-dihydro-1,4-phthalazinedione luminol, 5-amino-6, 7,8-trimethoxy- and the dimethylamino[ca]benz analog. These compounds can luminesce in the presence of alkaline hydrogen peroxide or calcium hypochlorite and base. Other examples of chemiluminescent compound fami-lies include, e.g., 2,4,5-triphenylimidazoles, para-dimethyl-amino and -methoxy substituents, oxalates such as oxalyl active esters, p-nitrophenyl, N-alkyl acridinum esters, luciferins, lucigenins, or acridinium esters. In some embodi-ments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

EXAMPLES

The following example is included for illustrative pur-poses only and is not intended to limit the scope of the present disclosure.

Example 1: Use of a Circularizable Probe, an Oligonucleotide Probe and RCA to Detect a Target Nucleic Acid This example describes an exemplary use of a circular-izable probe and a oligonucleotide probe for analyzing a biological sample. The circularizable probe and the oligo-nucleotide probe comprises hybridization regions that can hybridize to each other (e.g., based on sequence comple-mentarity) or to portions of the target nucleic acids. The circularizable probe includes a barcode region correspond-ing to the target nucleic acid or a sequence thereof, and the oligonucleotide probe comprises sequences that can be used as a splint to ligate the circularizable probe and permit rolling circle amplification (RCA) of the circularized probe, when sequences of the oligonucleotide probe is complemen-tary to the barcode region. If the sequences are not comple-mentary, the ligation and/or RCA does not proceed, thereby increasing the specificity of binding and amplification, and reducing non-specific baseline ligation and amplification.

A tissue sample is obtained and cryosectioned onto a glass slide for processing. The tissue is fixed by incubating in paraformaldehyde (PFA). One or more washes is performed and the tissue is then permeabilized. To prepare for probe hybridization, a wash buffer is added to the tissue section.

A probe set mixture is incubated with the thin tissue section sample and hybridization buffer for hybridization of the probe sets to target nucleic acid (e.g., mRNAs) in the sample. In some cases, various probes can be added to the sample together or provided separately. In this example, the circularizable probe comprises hybridization region HRa, hybridization region HR1 and hybridization region HRb that comprises a 3' splint hybridization region and a barcode region corresponding to the target nucleic acid or a sequence thereof. The oligonucleotide probe comprises hybridization region HR2, hybridization region HRa', and hybridization region HRb', that comprises a region complementary to the 3' splint hybridization region of HRb. The target nucleic acid comprises hybridization region HR1' and hybridization region HR2', and HR1 hybridizes to HR1', and HR2 hybrid-izes to HR2'. In some aspects, the oligonucleotide probe comprises a modification that protect the HRb' from 3'→5' exonuclease degradation. In some aspects, the HRb' com-prises one or more modifications that protect the sequence of HRb' from 3'→5' exonuclease degradation by a polymerase while allowing priming by the polymerase. In some examples, the one or more modifications comprise a termi-nal nucleotide modification and/or an internal nucleotide modification, for example, a 3' thiophosphate protection, a phosphorothioate bond, a 2'-modified nucleoside, or an inverted deoxythymidine base.

In some cases, before an amplification step and optionally before the ligation step, probe(s) that do not specifically hybridize to target nucleic acids in the sample can be disassociated from the target nucleic acids in the sample. The disassociation can comprise performing a stringent wash, e.g., a wash at a melting temperature that allows probes that are specifically hybridized to the target nucleic acid(s) to remain hybridized while probes comprising one or more mismatches are disassociated. In some embodiments, a blocking strand is hybridized to the probe or the target nucleic acid and partially blocks hybridization of a probe that does not hybridize to the target nucleic acid (e.g., the hybridization regions of the target nucleic acid), thus making it easier to disassociate the probe. In some cases, the blocking strand is incubated with the probe or the sample prior to or simultaneously with incubating the probe set mixture with the sample.

An exemplary probe set mixture comprises one or more circularizable probe and one or more oligonucleotide probe as depicted in FIG. 1A and FIG. 1B.

In some cases, when the circularizable probe and oligonucleotide probe hybridize to the target nucleic acid, and a sequence of HRb' is complementary to the barcode region of HRb (e.g., a first complementary barcode region that is complementary to the barcode region of HRb or portion thereof), ligation and rolling circle amplification (RCA) can occur (e.g., as depicted in FIG. 1A). The 5' end and the 3' end of the circularizable probe is ligated using the oligonucleotide probe as a splint, and the circularizable probe is circularized. In an example, HRb of the oligonucleotide probe can prime RCA of the circularized probe.

In some cases, at least a portion of HRb and HRb" are not complementary, for example, a sequence of HRb" comprises a second complementary barcode region that is not complementary to the barcode region of HRb, and RCA does not occur because the non-complementary HRb" sequence cannot prime the amplification (e.g., as depicted in FIG. 1B). In some aspects, the second complementary barcode region corresponds to a nucleic acid that is different from the target nucleic acid corresponding to the first barcode sequence, or sequence thereof.

The oligonucleotide probe or a separate primer can be used as a primer for amplification of the circularized probe. The sample is then incubated with a rolling-circle amplification (RCA) mixture containing a Phi29 DNA polymerase and dNTPs for RCA of the circularized probes. Fluorescently labeled oligonucleotides complementary to a portion of the RCA product, a barcode contained therein, or a secondary probe attached thereto are incubated with the sample. Multiple cycles of contacting the sample with probes and sequence determination (e.g., using in situ sequencing based on sequencing-by-ligation or sequencing-by-hybridization) can be performed. Fluorescent images can be obtained in each cycle, and one or more wash steps can be performed in a cycle or between cycles.

Example 2: Use of Oligonucleotide Probes with Exemplary Modification

This example describes exemplary design and methods for oligonucleotide probes with exemplary modifications, together with circularizable probes. The oligonucleotide probe can comprise a modification, for example at or near the 5' end, that selectively permits ligation and/or RCA of the circularizable probe when the sequences of a hybridization region of the oligonucleotide probe is complementary to sequences of the circularizable probe, for example, the barcode region. In some aspects, the modification prevents or blocks priming by a polymerase on the 3' end. If the sequences are not complementary, the ligation and/or RCA does not proceed, thereby increasing the specificity of binding and amplification, and reducing non-specific baseline ligation and amplification. Examples of modifications include one or more uracil-containing residues and/or nuclease cleavage sites cleavable by an enzyme.

An exemplary probe set mixture comprises one or more circularizable probe and one or more oligonucleotide probe as depicted in FIG. 2A and FIG. 2B.

A probe set mixture comprising a circularizable probe and an oligonucleotide probe are incubated with a thin tissue section sample and hybridization buffer for hybridization of the probe sets to target nucleic acid (e.g., mRNAs) in the sample, generally as described in Example 1. In this example, the circularizable probe comprises in the 5' to 3' direction: hybridization region HRa, hybridization region HR1 and hybridization region HRb that comprises a 3' splint hybridization region and a barcode region corresponding to the target nucleic acid or a sequence thereof. The oligonucleotide probe comprises in the 5' to 3' direction: hybridization region HR2, hybridization region HRa', and hybridization region HRb' that comprises a region complementary to the 3' splint hybridization region of HRb. In some examples, HRa hybridizes to HRa', and the 3' splint hybridization region of HRb hybridizes to its complementary region in HRb'. The target nucleic acid comprises hybridization region HR1' and hybridization region HR2', and HR1 hybridizes to HR1', and HR2 hybridizes to HR2'.

In some examples, as depicted in FIG. 2A, the circularizable probe and oligonucleotide probe hybridize to the target nucleic acid, and HRa of the circularizable probe hybridizes to HRa' of the oligonucleotide probe and the 3' splint hybridization region of HRb of the circularizable probe hybridizes to its complementary region in HRb' of the oligonucleotide probe. The 5' end and the 3' end of the circularizable probe is ligated using the oligonucleotide probe as a splint, and the circularizable probe is circularized. When HRb' is complementary to the barcode region of HRb, the oligonucleotide probe is nicked at a specific location with an enzyme that cleaves the oligonucleotide probe but not the circular probe, freeing the 3' end of the oligonucleotide probe from the modification, and RCA can be primed using the 3' end of the oligonucleotide probe as a primer.

For example, the HRb' comprises one or more modifications that block priming by a polymerase, and when the first complementary barcode region is complementary to the barcode region in HRb, then HRb' is cleaved to remove the one or more modifications, and the portion of the oligonucleotide probe that remains hybridized to the circularized probe primes RCA of the circularized probe. In some aspects, a portion of HRb' that remains hybridized to the barcode region primes RCA of the circularized probe. For example, the oligonucleotide probe contains one or more uracil residues, and HRb' is cleaved by a uracil-specific excision reagent. Exemplary enzymes that can be used to cleave include a uracil-DNA glycosylase (UDG) or an endonuclease, such as Endonuclease VIII.

In some examples, as shown in FIG. 2B, when at least a portion of HRb and HRb" are not complementary, for example, a sequence of HRb" comprises a second complementary barcode region that is not complementary to the barcode region of HRb, RCA does not occur because the non-complementary sequence of the oligonucleotide probe is not cleaved. The modification prevents RCA from occurring, for example, as the second complementary barcode region or portion thereof is not capable of priming RCA of the circularized probe. For example, when the second complementary barcode region is not complementary to the barcode region, the one or more modifications are not removed, and HRb" or portion thereof is not capable of priming RCA of the circularized probe. In some cases, HRb"

comprises one or more uracil-containing residues and/or nuclease cleavage sites cleavable by an enzyme, and the second complementary barcode region is not cleaved by the enzyme.

Generated RCA products can be detected and analyzed, generally as described in Example 1.

Example 3: Use of Oligonucleotide Probes that can be Cleaved by an Enzyme

This example describes exemplary design and methods for oligonucleotide probes with different exemplary modifications, together with circularizable probes. The oligonucleotide probe can comprise a modification, for example at or near the 5' end, that selectively permits ligation and/or RCA of the circularizable probe when the sequences of a hybridization region of the oligonucleotide probe is complementary to sequences of the circularizable probe, for example, the barcode region. Exemplary modifications include modifications that can be cleaved by an enzyme that cleaves a non-complementary HRb' sequence or a portion thereof of the oligonucleotide probe and/or the HRb of the circularizable probe. If the sequences are not complementary, the circularizable probe is cleaved or nicked, and ligation and/or RCA does not proceed. In some cases, the oligonucleotide probe is also cleaved or nicked. The provided examples can increase the specificity of binding and amplification, and reduce non-specific baseline ligation and amplification.

An exemplary probe set mixture comprises one or more circularizable probe and one or more oligonucleotide probe as depicted in FIG. 3A and FIG. 3B.

A probe set mixture comprising a circularizable probe and an oligonucleotide probe, similar to the probes described in Example 2, are incubated with a thin tissue section sample and hybridization buffer for hybridization of the probe sets to target nucleic acid (e.g., mRNAs) in the sample, generally as described in Example 1.

In some examples, as depicted in FIG. 3A, rolling circle amplification (RCA) can occur when the circularizable probe and oligonucleotide probe hybridize to the target nucleic acid, and a sequence of HRb' is complementary to the barcode region of HRb (e.g., a first complementary barcode region that is complementary to the barcode region of HRb or portion thereof). After hybridization, ligation, amplification and detection of the bound probes can be performed, generally as described in Example 1. In some examples, as shown in FIG. 3B, a second complementary barcode region of HRb" of the oligonucleotide probe is not complementary to the barcode region of HRb of the circularizable probe, and an enzyme can nick the oligonucleotide probe or the circularizable probe or both, and no RCA occurs. In some aspects, at least a portion of the barcode region remains single-stranded and is cleaved, thereby preventing generation of the circularized probe and/or linearizing the circularized probe to prevent generation of the RCA product. In some cases, the barcode region is cleaved by a Type II restriction enzyme, such as AvaII, HaeII, DdeI, AluI, Sau3AI, AccII, TthHB8I and HapII. In some examples, at least a portion of the second complementary barcode region remains single-stranded and is cleaved. In some cases, the second complementary barcode region is cleaved by a Type II restriction enzyme, such as AvaII, HaeII, DdeI, AluI, Sau3 AI, AccII, TthHB8I and HapII.

Generated RCA products can be detected and analyzed, generally as described in Example 1.

Example 4: Use of Oligonucleotide Probes as a Splint to Circularize and Amplify the Circularizable Probe This example describes depict exemplary design and method for analyzing a biological sample that employ an oligonucleotide probe as a splint to circularize and amplify the circularizable probe. The oligonucleotide probe comprises sequences that can be employed as a splint to ligate the 5' and 3' ends of the circularizable probe. For example, the oligonucleotide probe can include a portion with a sequence that is complementary to a barcode region present at one end of the circularizable probe, adjacent to or near a common sequence that is complementary to a common sequence present at or near the other end of the circularizable probe. The splint can selectively permit ligation and/or RCA of the circularizable probe when the sequences of a hybridization region of the oligonucleotide probe is complementary to sequences of the circularizable probe, for example, the barcode region. In such cases, the two ends of the circularization probe (one comprising a barcode region that corresponds to a target nucleic acid and the other comprising a common sequence) can be ligated. If the sequences are not complementary, the circularizable probe cannot be ligated, and RCA does not proceed. The provided examples can increase the specificity of binding and amplification, and reduce non-specific baseline ligation and amplification.

An exemplary probe set mixture comprises one or more circularizable probe and one or more oligonucleotide probe as depicted in FIG. 4A and FIG. 4B.

A probe set mixture comprising a circularizable probe and an oligonucleotide probe, are incubated with a thin tissue section sample and hybridization buffer for hybridization of the probe sets to target nucleic acid (e.g., mRNAs) in the sample, generally as described in Example 1. In this example, the oligonucleotide probe comprises hybridization region HR2, hybridization region HRa', and hybridization region HRb', and the circularizable probe comprises hybridization region HRa, hybridization region HR1, and hybridization region HRb comprising a barcode region corresponding to the target nucleic acid or a sequence thereof. In some examples, HRa hybridizes to HRa'. In some examples, HRa is not specific to the target nucleic acid or sequence thereof, for example, is a common sequence among various circularizable probes targeting different analytes (e.g., different nucleic acids such as RNA species). In some cases, HRa comprises a second barcode region, and the second barcode region or the first and second barcode region together correspond to the target nucleic acid or sequence thereof. The target nucleic acid comprises hybridization region HR1' and hybridization region HR2', and HR1 hybridizes to HR1', and HR2 hybridizes to HR2'. In certain examples, the circularizable probe comprises HRa, HR1, and HRb in the 5' to 3' direction; the oligonucleotide probe comprises HR2, HRa', and HRb' in the 5' to 3' direction, and the target nucleic acid comprises HR1' and HR2' in the 5' to 3' direction. In other examples, the circularizable probe comprises HRa, HR1, and HRb in the 3' to 5' direction, the oligonucleotide probe comprises HR2, HRa', and HRb' in the 3' to 5' direction, and the target nucleic acid comprises HR1' and HR2' in the 3' to 5' direction.

In some cases, as depicted in in FIG. 4A, the oligonucleotide probe comprises HRa' that is a common sequence, and a sequence of HRb' that is complementary to the barcode region of HRb. In some examples, barcode region is at the 3' end of HRb, or first at the 3' end of the circularizable probe. The barcode region corresponds to the target nucleic acid or a sequence thereof. In some cases, the circularizable probe comprises a sequence 5' to the barcode region, and the sequence 5' to the barcode region hybridizes to the oligonucleotide probe. The circularizable probe and oligonucleotide probe hybridize to the target nucleic acid, and HRa of the circularizable probe hybridizes to HRa' of the oligonucleotide probe. HRa and HRb are ligated using the oligonucleotide probe as a splint, and the circularizable probe is circularized. RCA of the circularized probe is primed by the oligonucleotide probe or a separate primer. In other cases, as shown in FIG. 4B, the sequence of HRb" is or comprises a second complementary barcode region that is not complementary to the barcode region of HRb. In such instances, HRa and HRb are not ligated, the probe is not circularized, and no RCA occurs. In some cases, the second complementary barcode region corresponds to a nucleic acid different from the target nucleic acid or sequence thereof.

Generated RCA products can be detected and analyzed, generally as described in Example 1.

Example 5: Use of Oligonucleotide Probes with Circular Probes with a Flap

This example describes depict exemplary design and method for analyzing a biological sample that employ a circularizable probe with a flap, at the 3' end or 5' end of the probe molecule, and an oligonucleotide probe that can serve as a splint to circularize and amplify the circularizable probe. For example, the circularizable probe contains a 5' flap, a sequence 5' to the barcode region, that does not hybridize to the oligonucleotide probe. The presence of the splint on the oligonucleotide probe can selectively permit removal of the flap and ligation of the circularizable probe when the barcode region and the sequences of a hybridization region of the oligonucleotide probe are complementary. In such cases, the flap is removed, and the two ends of the circularization probe is ligated. If the sequences are not complementary, the circularizable probe cannot be ligated, and RCA does not proceed. The provided examples can increase the specificity of binding and amplification, and reduce non-specific baseline ligation and amplification.

An exemplary probe set mixture comprises one or more circularizable probe and one or more oligonucleotide probe as depicted in FIG. 5A and FIG. 5B.

A probe set mixture comprising a circularizable probe and an oligonucleotide probe, are incubated with a thin tissue section sample and hybridization buffer for hybridization of the probe sets to target nucleic acid (e.g., mRNAs) in the sample, generally as described in Example 1. In this example, the oligonucleotide probe comprises hybridization region HR2, hybridization region HRa', and hybridization region HRb', and the circularizable probe comprises a flap, hybridization region HRa, hybridization region HR1, and hybridization region HRb comprising a barcode region corresponding to the target nucleic acid or a sequence thereof. In some examples, HRa hybridizes to HRa'. The target nucleic acid comprises hybridization region HR1' and hybridization region HR2', and HR1 hybridizes to HR1', and HR2 hybridizes to HR2'. In some cases, the oligonucleotide probe is DNA and the circularizable probe does not comprise a ribonucleotide at the 3' end.

In certain examples, the flap is a 5' flap. For example, the 5' flap is a sequence present 5' of the HRa that does not hybridize to the oligonucleotide probe. In some cases, the flap is a 3' flap. For example, the circularizable probe comprises a sequence 3' to the barcode region. In some cases, the sequence 3' to the barcode region hybridizes to the oligonucleotide probe and is no more than 5 nucleotides in length. In other cases, the sequence 3' to the barcode region forms a 3' flap that does not hybridize to the oligonucleotide probe.

In some cases, as shown in FIG. 5A, the circularizable probe and oligonucleotide probe hybridize to the target nucleic acid, and when the barcode region is complementary to HRb' or a portion thereof (e.g., first complementary barcode region of the probe oligonucleotide), the flap (5' flap in FIG. 5A) is removed by an endonuclease or a polymerase, and the circularizable probe is circularized by ligating HRa and HRb using the oligonucleotide probe as a splint. In some examples, the endonuclease is a flap endonuclease 1 (FEN1) and the polymerase is a *Thermus thermophilus* (Tth) polymerase. The oligonucleotide probe or a portion thereof, or a separate primer is used to prime RCA of the circularized probe. In some cases, as shown in FIG. 5B, when the barcode region on the circularizable probe is not complementary to the second complementary barcode region on the oligonucleotide probe, the flap (5' flap in FIG. 5B) of the circularizable probe is not cleaved, the flap prevents ligation of HRa and HRb and circularization, and no RCA occurs. In some cases, the second complementary barcode region corresponds to a nucleic acid different from the target nucleic acid or sequence thereof.

Generated RCA products can be detected and analyzed, generally as described in Example 1.

The present disclosure is not intended to be limited in scope to the particular disclosed embodiments, which are provided, for example, to illustrate various aspects of the present disclosure. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for analyzing a biological sample, the method comprising:
   a) contacting the biological sample comprising a target nucleic acid comprising hybridization region HR1' and hybridization region HR2', with:
      (i) a circularizable probe comprising hybridization region HR1 and hybridization region HRb, wherein HR1 hybridizes to HR1', and wherein HRb comprises a barcode region, and
      (ii) an oligonucleotide probe comprising hybridization region HR2 and hybridization region HRb', wherein HR2 hybridizes to HR2' and wherein HRb' hybridizes to HRb, and the oligonucleotide probe comprises one or more modifications;
   b) ligating the ends of the circularizable probe using the oligonucleotide probe as a splint to generate a circularized probe;
   c) using the oligonucleotide probe or a primer to prime rolling circle amplification (RCA) of the circularized probe to generate an RCA product; and
   d) detecting the RCA product, thereby detecting the target nucleic acid in the biological sample.

2. The method of claim 1, wherein the circularizable probe further comprises hybridization region HRa, and the oligonucleotide probe further comprises hybridization region HRa' which hybridizes to HRa.

3. The method of claim 1, wherein:

HRb' comprises a barcode region complementary to the barcode region of HRb, in step a), the biological sample is contacted with another oligonucleotide probe comprising hybridization region HRb", wherein HRb" comprises a barcode region that is not complementary to the barcode region of HRb, and in step c), HRb" or a portion thereof is not configured to prime RCA of a circularized probe generated by ligation using the another oligonucleotide probe as a splint.

4. The method of claim 1, wherein the one or more modifications protect the oligonucleotide probe from 3'→5' exonuclease degradation, and wherein:

(i) the one or more modifications allow primer extension by a polymerase, and the method does not comprise contacting the biological sample with an enzyme capable of removing the one or more modifications; or (ii) the one or more modifications block primer extension by a polymerase, and the method further comprises contacting the biological sample with an agent capable of removing the one or more modifications.

5. The method of claim 1, wherein the one or more modifications comprise a terminal modification.

6. The method of claim 1, wherein the biological sample is contacted with another oligonucleotide probe comprising HRa' and hybridization region HRb" in the 5' to 3' direction, wherein HRb" comprises (i) a region complementary to a non-barcode region of HRb and (ii) a barcode region that is not complementary to the barcode region of HRb.

7. The method of claim 1, wherein HRb' comprises one or more uracil-containing residues and/or nuclease cleavage sites cleavable by an enzyme or a uracil-specific excision reagent.

8. The method of claim 6, wherein:

the barcode region in HRb" remains single-stranded and is cleaved by the enzyme, and/or the barcode region of HRb remains single-stranded and is cleaved by the enzyme.

9. The method of claim 6, wherein the barcode region in HRb" corresponds to another target nucleic acid distinct from the target nucleic acid.

10. A method for analyzing a biological sample, the method comprising:

a) contacting the biological sample comprising a target nucleic acid comprising in the 5' to 3' direction: hybridization region HR1' and hybridization region HR2', with:

(i) a plurality of circularizable probes, wherein a circularizable probe of the plurality of circularizable probes comprises hybridization region HRa, hybridization region HR1, and hybridization region HRb, wherein HRb comprises a barcode region, and (ii) a plurality of oligonucleotide probes, wherein an oligonucleotide probe of the plurality of oligonucleotide probes comprises hybridization region HR2, hybridization region HRa', and hybridization region HRb', wherein HRb' or a portion thereof is complementary to the barcode region of HRb; and wherein:

HRa hybridizes to HRa', HR1 hybridizes to HR1', and HR2 hybridizes to HR2';

b) ligating HRa and HRb using the oligonucleotide probe as a splint, wherein the circularizable probe is circularized to generate a circularized probe;

c) using the oligonucleotide probe or a portion thereof or a primer to prime rolling circle amplification (RCA) of the circularized probe to generate an RCA product; and d) detecting the RCA product, thereby detecting the target nucleic acid in the biological sample.

11. The method of claim 10, wherein:

the circularizable probe comprises HRa, HR1, and HRb in the 5' to 3' direction, the oligonucleotide probe comprises HR2, HRa', and HRb' in the 5' to 3' direction, and the target nucleic acid comprises HR1' and HR2' in the 5' to 3' direction.

12. The method of claim 1, wherein the barcode region is at the 3' end of the circularizable probe.

13. The method of claim 11, wherein:

the plurality of oligonucleotide probes comprises another oligonucleotide probe comprising HRa' and hybridization region HRb", wherein HRb" comprises (i) a region complementary to a non-barcode region of HRb and (ii) a barcode region that is not complementary to the barcode region of HRb; and the barcode region in HRb" is not hybridized to the barcode region of HRb.

14. The method of claim 10, wherein the circularizable probe comprises a sequence 5' to HRa, and the sequence 5' to HRa forms a 5' flap that does not hybridize to the oligonucleotide probe.

15. The method of claim 14, comprising cleaving the 5' flap of the circularizable probe using an enzyme.

16. A method, comprising:

a) contacting a biological sample comprising a target nucleic acid comprising in the 5' to 3' direction: hybridization region HR1' and hybridization region HR2', with:

(i) a plurality of circularizable probes, wherein a circularizable probe of the plurality of circularizable probes comprises, in the 5' to 3' direction: a 5' flap, hybridization region HRa, hybridization region HR1, and hybridization region HRb, wherein HRb comprises a barcode region, and (ii) a plurality of oligonucleotide probes, wherein an oligonucleotide probe of the plurality of oligonucleotide probes comprises in the 5' to 3' direction: hybridization region HR2, hybridization region HRa', and hybridization region HRb', wherein HRb' or a portion thereof is complementary to the barcode region of HRb; and wherein:

HRa hybridizes to HRa', HR1 hybridizes to HR1', and HR2 hybridizes to HR2';

b) cleaving the 5' flap of the circularizable probe by an enzyme;

c) ligating HRa and HRb using the oligonucleotide probe as a splint, wherein the circularizable probe is circularized to generate a circularized probe;

d) using the oligonucleotide probe or a portion thereof to prime rolling circle amplification (RCA) of the circularized probe to generate an RCA product; and e) detecting the RCA product, thereby detecting the target nucleic acid in the biological sample.

17. The method of claim 16, wherein the enzyme is a flap endonuclease 1 (FEN1) and a *Thermus thermophilus* (Tth) polymerase is used in d) to generate the RCA product.

18. The method of claim 10, wherein:

the barcode region in HRb is a first barcode region and HRa comprises a second barcode region, wherein the first and second barcode regions each independently comprises one or more barcodes, optionally wherein: (i) the first barcode region corresponds to the target nucleic acid or sequence thereof; (ii) the second barcode region corresponds to the target nucleic acid or sequence thereof; or (iii) the combination of the first and second barcode regions correspond to the target nucleic acid or sequence thereof.

19. The method of claim 1, wherein the RCA product is generated and detected in situ in the biological sample.

20. The method of claim 10, wherein the RCA product is generated and detected in situ in the biological sample.

\*    \*    \*    \*    \*